(12) United States Patent
Hansen et al.

(10) Patent No.: US 10,815,481 B2
(45) Date of Patent: Oct. 27, 2020

(54) CHIRAL LIBRARY SCREEN

(71) Applicant: Roche Innovation Center Copenhagen A/S, Horsholm (DK)

(72) Inventors: Henrik Frydenlund Hansen, Horsholm (DK); Troels Koch, Horsholm (DK); Sabine Sewing, Basel (CH); Nanna Albaek, Horsholm (DK); Peter Hagedorn, Horsholm (DK); Jacob Ravn, Horsholm (DK); Christoph Rosenbohm, Hørsholm (DK); Annie Moisan, Basel (CH); Marcel Gubler, Basel (CH)

(73) Assignee: Roche Innovation Center Copenhagen A/S, Basel (CH)

( * ) Notice: Subject to any disclaimer, the term of this patent is extended or adjusted under 35 U.S.C. 154(b) by 0 days.

(21) Appl. No.: 15/536,152

(22) PCT Filed: Dec. 16, 2015

(86) PCT No.: PCT/EP2015/079915
§ 371 (c)(1),
(2) Date: Jun. 15, 2017

(87) PCT Pub. No.: WO2016/096938
PCT Pub. Date: Jun. 23, 2016

(65) Prior Publication Data
US 2017/0335323 A1 Nov. 23, 2017

(30) Foreign Application Priority Data

| Dec. 16, 2014 | (EP) | 1198167 |
|---|---|---|
| Aug. 25, 2015 | (EP) | 15182401 |
| Oct. 22, 2015 | (EP) | 15191074 |
| Oct. 22, 2015 | (EP) | 15191075 |
| Oct. 22, 2015 | (EP) | 15191076 |
| Nov. 18, 2015 | (EP) | 15195198 |
| Nov. 18, 2015 | (EP) | 15195202 |
| Nov. 18, 2015 | (WO) | PCT/EP2015/076967 |
| Nov. 18, 2015 | (WO) | PCT/EP2015/076971 |

(51) Int. Cl.
*C12N 15/113* (2010.01)
*C12N 15/11* (2006.01)
*G01N 33/50* (2006.01)

(52) U.S. Cl.
CPC .......... *C12N 15/113* (2013.01); *C12N 15/111* (2013.01); *G01N 33/5014* (2013.01); *G01N 33/5088* (2013.01); *C12N 2310/11* (2013.01); *C12N 2310/315* (2013.01); *C12N 2310/3231* (2013.01); *C12N 2310/341* (2013.01); *C12N 2310/345* (2013.01); *C12N 2310/346* (2013.01); *C12N 2320/53* (2013.01); *C12N 2330/31* (2013.01)

(58) Field of Classification Search
None
See application file for complete search history.

(56) References Cited

U.S. PATENT DOCUMENTS

| 4,914,210 A | 4/1990 | Levenson et al. |
|---|---|---|
| 4,962,029 A | 10/1990 | Levenson et al. |
| 7,087,229 B2 | 8/2006 | Zhao et al. |
| 7,399,845 B2 | 7/2008 | Seth et al. |
| 2004/0096848 A1* | 5/2004 | Thrue .................... A61K 31/70 435/6.14 |
| 2010/0249219 A1 | 9/2010 | Hedtjarn et al. |
| 2015/0211006 A1* | 7/2015 | Butler .................. C12Q 1/6876 514/44 A |
| 2018/0216108 A1* | 8/2018 | Vargeese ................. A61P 25/28 |

FOREIGN PATENT DOCUMENTS

| EP | 1222309 | 7/2002 |
|---|---|---|
| EP | 1984381 | 10/2008 |
| JP | 2014/221817 | 9/2019 |
| WO | WO 96/39154 | 12/1996 |
| WO | WO 2004/046160 | 6/2004 |
| WO | WO 2005/023995 | 3/2005 |
| WO | WO 2007/031091 | 3/2007 |
| WO | WO 2007/134181 | 11/2007 |
| WO | WO 2007/146511 | 12/2007 |
| WO | WO 2008/034122 | 3/2008 |
| WO | WO 2008/034123 | 3/2008 |
| WO | WO2008/049085 A1 | 4/2008 |
| WO | WO 2008/113832 | 9/2008 |
| WO | WO 2008/150729 | 12/2008 |
| WO | WO 2008/154401 | 12/2008 |
| WO | WO 2009/006478 | 1/2009 |
| WO | WO 2009/067647 | 5/2009 |
| WO | WO 2009/090182 | 7/2009 |
| WO | WO 2009/100320 | 8/2009 |
| WO | WO 2009/124238 | 10/2009 |
| WO | WO2009/124295 A2 | 10/2009 |
| WO | WO 2010/036698 | 4/2010 |
| WO | WO 2011/005761 | 1/2011 |
| WO | WO 2011/017521 | 2/2011 |
| WO | WO 2011/085102 | 7/2011 |
| WO | WO 2011/115818 | 9/2011 |
| WO | WO 2013/012758 | 1/2013 |
| WO | WO 2014/010250 | 1/2014 |

(Continued)

OTHER PUBLICATIONS

Swayze et al (Nucleic Acids Research, 2007, vol. 35, No. 2 687-700) (Year: 2007).*

(Continued)

*Primary Examiner* — Richard A Schnizer
(74) *Attorney, Agent, or Firm* — Fish & Richardson P.C.

(57) ABSTRACT

The invention relates to a method of identifying stereodefined phosphorothioate oligonucleotide variants with reduced toxicity by creating and screening libraries of stereodefined chiral phosphorothioate variants for compounds with reduced toxicity, either in vitro or in vivo.

Figure 1:
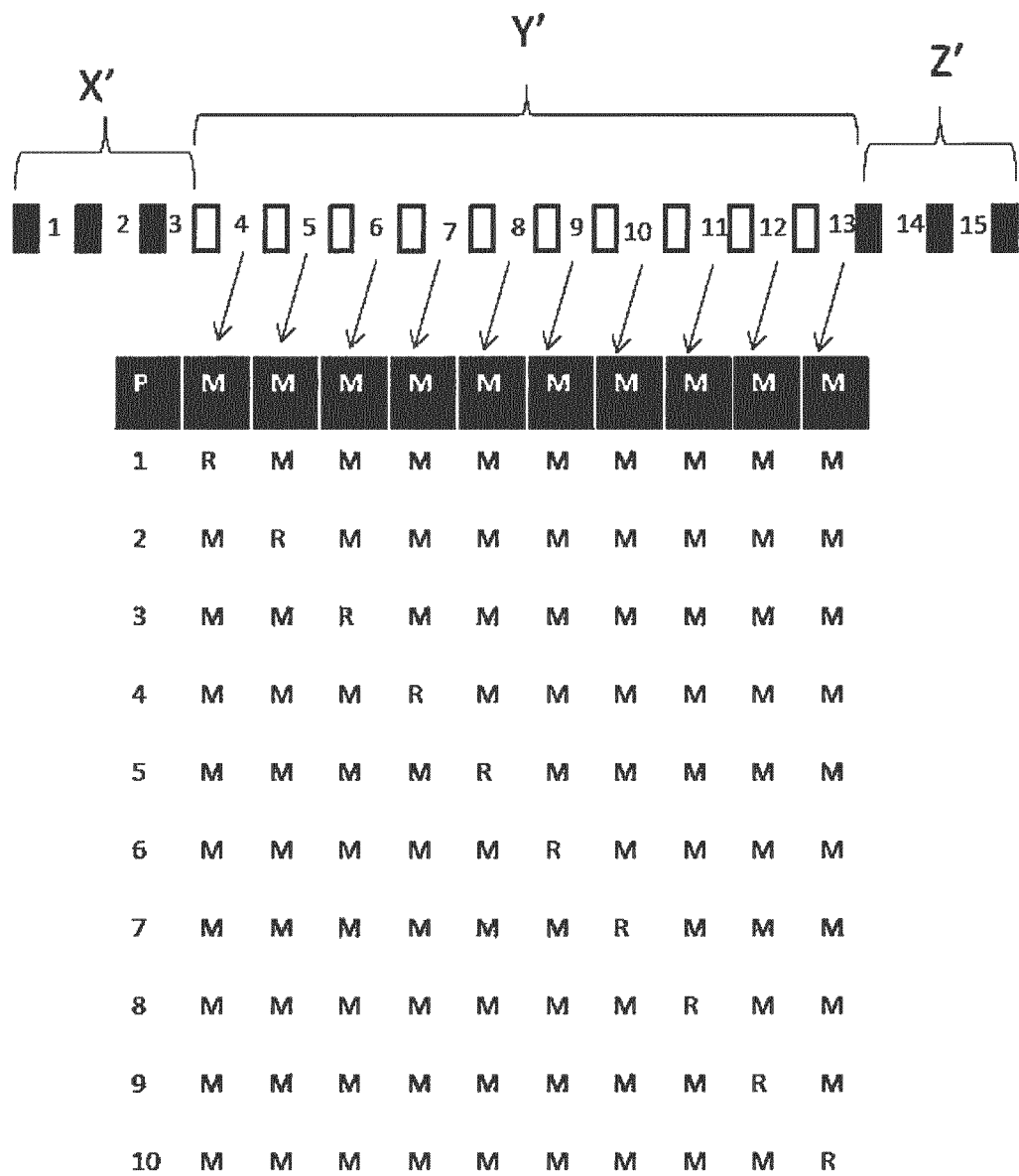

14 Claims, 7 Drawing Sheets
Specification includes a Sequence Listing.

(56) References Cited

FOREIGN PATENT DOCUMENTS

| WO | WO 2014/012081 | 1/2014 |
| WO | WO 2014/076195 | 5/2014 |
| WO | WO 2014/118267 | 8/2014 |
| WO | WO 2015/107425 | 7/2015 |
| WO | WO 2014/010718 | 6/2016 |

OTHER PUBLICATIONS

Soldatow et al (Toxicol. Res. 2:23-39, 2013) (Year: 2013).*
Gagnon et al (10th Annual Meeting of the Oligonucleotide Therapeutics Society, San Diego, CA, Oct. 12-15, 2014, Session Summaries. (Year: 2014).*
International Search Report and Written Opinion for International Application No. PCT/EP2015/079915 dated Apr. 1, 2016, 10 pages.
Wan et al., "Synthesis, biophysical properties and biological activity of second generation antisense oligonucleotides containing chiral phosphorothioate linkages," Nucleic Acids Research, Dec. 16, 2014, 42(22):13456-13468; Epub Nov. 14, 2014.
Christensen, "Intercalating nucleic acids containing insertions of 1-O-(1-pyrenylmethyl)glycerol: stabilisation of dsDNA and discrimination of DNA over RNA," Nucl. Acids. Res., 2002 30(22):4918-4925.
Freier & Altmann, "The ups and downs of nucleic acid duplex stability: structure-stability studies on chemically-modified DNA:RNA duplexes," Nucl. Acid Res., 1997, 25(22):4429-4443.
Fluiter et al., "Filling the gap in LNA antisense oligo gapmers: the effects of unlocked nucleic acid (UNA) and 4'-C-hydroxymethyl-DNA modifications on RNase H recruitment and efficacy of an LNA gapmer," Mol. Biosyst., 2009, 5(8):838-843.
Hagedorn et al., "Hepatotoxic potential of therapeutic oligonucleotides can be predicted from their sequence and modification pattern," Nucleic Acid Therapeutics 2013, 23(5):302-310.
Levin et al., "Basic Principles of the Pharmacokinetics of Antisense Oligonucleotide Drugs. In Antisense Drug Technology: Principles, Strategies, and Applications," Second Edition, Crooke, ST. Boca Raton, FL, CRC Press, Chapter 7, 183-215, 2008.
Manoharan et al., "Novel functionalization of the sugar moiety of nucleic acids for multiple labeling in the minor groove," Tetrahedron Letters, 1991, 32(49):7171-7174.
Oka et al., "Solid-Phase Synthesis of Stereoregular Oligodeoxyribonucleoside Phosphorothioates Using Bicyclic Oxazaphospholidine Derivatives as Monomer Units," J. Am. Chem. Soc. 2008, 130(47):16031-16037.
Karwowski et al. "Stereocontrolled synthesis of LNA dinucleoside phosphorothioate by the oxathiaphospholane approach," Bioorganic & Med. Chem. Letts., 2001, 11(8):1001-1003.
Koziolkiewicz et al., "Stereodifferentiation—the effect of P chirality of oligo (nucleoside phosphorothioates) on the activity of bacterial RNase H," Nucleic Acids Research, 1995, 23(24):5000-5005.
Krieg et al. "P-Chirality-Dependent Immune Activation by Phosphorothioate CpG Oligodeoxynucleotides," Oligonucleotides, 2004, 13(6):491-499.
Seth at al., "Synthesis and biophysical evaluation of 2',4'-constrained 2'O-methoxyethyl and 2',4'- constrained 2'O-ethyl nucleic acid analogues," J. Org. Chem, 2010, 75(5):1569-1581.
Seth et al., "Short antisense oligonucleotides with novel 2'-4' conformationaly restricted nucleoside analogues show improved potency without increased toxcity in animals," J. Med. Chem., 2009, 52(1):10-13.
Stec et al. "Deoxyribonucleoside 3'-O-(2-Thio- and 2-Oxo-"spiro"-4,4-pentamethylene-1,3,2-oxathiaphospholane)s: Monomers for Stereocontrolled Synthesis of Oligo(deoxyribonucleoside phosphorothioate)s and Chimeric PS/PO Oligonucleotides," J. Am. Chem. Soc., 1998, 120(29):7156-7167.
Uhlmann, "Recent advances in the medical chemistry of antisense oligonucleotides," Curr. Opinion in Drug Development, 2000, 3(2):293-213.
Vester et al., "Chemically modified oligonucleotides with efficient RNase H response," Bioorg. Med. Chem. Lett., 2008, 18(7):2296-2300.
Corradini et al., "Chirality as a tool in nucleic acid recognition: principles and relevance in biotechnology and in medicinal chemistry," Chirality, 2007, May 5, 2017, 19(4):269-294.
Iannitti et al., "Phosphorothioate Oligonucleotides: Effectiveness and Toxicity," Curr Drug Targ., 2014, 15:663-673.
Wave Life Sciences Poster, "Therapeutic Implications of Controlling P-Chiralty in Phosphorioate Oligonucleotides," TIDES, May 3-6 2014, San Diego, 1 pg.

* cited by examiner a) Content in liver b) Content in kidney c) Content in spleen

| LNAs | | Compound | | | | | control LNAs | |
|---|---|---|---|---|---|---|---|---|
| Readout | c [µM] | #56 | #57 | #58 | #59 | #60 | - | + |
| LDH % control | 1 | 160 | 173 | 91 | 174 | 85 | | |
| | 3 | 184 | 198 | 93 | 217 | 98 | | |
| | 10 | 210 | 223 | 112 | 256 | 112 | 114 | 256 |
| | 30 | 246 | 225 | 116 | 257 | 112 | | |
| ATP % control | 1 | 71 | 59 | 87 | 64 | 81 | | |
| | 3 | 59 | 45 | 83 | 53 | 71 | | |
| | 10 | 50 | 40 | 78 | 44 | 69 | 101 | 28 |
| | 30 | 43 | 32 | 75 | 37 | 64 | | |

Severity: no tox → tox

SEQUENCE LISTING

<160> NUMBER OF SEQ ID NOS: 20

<210> SEQ ID NO 1
<211> LENGTH: 16
<212> TYPE: DNA
<213> ORGANISM: artificial
<220> FEATURE:
<223> OTHER INFORMATION: Oligonucleotide sequence

<400> SEQUENCE: 1
actgctttcc actctg                                                       16

<210> SEQ ID NO 2
<211> LENGTH: 14
<212> TYPE: DNA
<213> ORGANISM: Artificial
<220> FEATURE:
<223> OTHER INFORMATION: Oligonucleotide sequence

<400> SEQUENCE: 2
tcatggctgc agct                                                         14

<210> SEQ ID NO 3
<211> LENGTH: 13
<212> TYPE: DNA
<213> ORGANISM: Artificial
<220> FEATURE:
<223> OTHER INFORMATION: Oligonucleotide sequence

<400> SEQUENCE: 3
gcattggtat tca                                                          13

<210> SEQ ID NO 4
<211> LENGTH: 16
<212> TYPE: DNA
<213> ORGANISM: Artificial
<220> FEATURE:
<223> OTHER INFORMATION: Oligonucleotide sequence

<400> SEQUENCE: 4
cacattcctt gctctg                                                       16

<210> SEQ ID NO 5
<211> LENGTH: 13
<212> TYPE: DNA
<213> ORGANISM: artificial
<220> FEATURE:
<223> OTHER INFORMATION: Oligonucleotide sequence

```
<400> SEQUENCE: 5
gcaagcatcc tgt                                                          13

<210> SEQ ID NO 6
<211> LENGTH: 20
<212> TYPE: RNA
<213> ORGANISM: artificial
<220> FEATURE:
<223> OTHER INFORMATION: RNA substrate

<400> SEQUENCE: 6
ugagaauacc aaugcuaagu                                                   20

<210> SEQ ID NO 7
<211> LENGTH: 20
<212> TYPE: RNA
<213> ORGANISM: artificial
<220> FEATURE:
<223> OTHER INFORMATION: RNA substrate

<400> SEQUENCE: 7
caggaauacc aaugcagaga                                                   20

<210> SEQ ID NO 8
<211> LENGTH: 20
<212> TYPE: RNA
<213> ORGANISM: artificial
<220> FEATURE:
<223> OTHER INFORMATION: RNA substrate

<400> SEQUENCE: 8
aguggauacc aaugcugcag                                                   20

<210> SEQ ID NO 9
<211> LENGTH: 20
<212> TYPE: RNA
<213> ORGANISM: artificial
<220> FEATURE:
<223> OTHER INFORMATION: RNA substrate

<400> SEQUENCE: 9
uuuggauacc aaugcauagg                                                   20

<210> SEQ ID NO 10
<211> LENGTH: 20
<212> TYPE: RNA
<213> ORGANISM: artificial
<220> FEATURE:
<223> OTHER INFORMATION: RNA substrate

<400> SEQUENCE: 10
ucugaguacc aaugccauga                                                   20

<210> SEQ ID NO 11
<211> LENGTH: 20
<212> TYPE: RNA
<213> ORGANISM: artificial
<220> FEATURE:
<223> OTHER INFORMATION: RNA substrate

<400> SEQUENCE: 11
gcugaaugcc aaugcugagu                                                   20
```

```
<210> SEQ ID NO 12
<211> LENGTH: 20
<212> TYPE: RNA
<213> ORGANISM: artificial
<220> FEATURE:
<223> OTHER INFORMATION: RNA substrate

<400> SEQUENCE: 12
ucugaauacc gaugcuuuaa                                                   20

<210> SEQ ID NO 13
<211> LENGTH: 20
<212> TYPE: RNA
<213> ORGANISM: artificial
<220> FEATURE:
<223> OTHER INFORMATION: RNA substrate

<400> SEQUENCE: 13
ucugaauacc agugcuuuaa                                                   20

<210> SEQ ID NO 14
<211> LENGTH: 21
<212> TYPE: RNA
<213> ORGANISM: artificial
<220> FEATURE:
<223> OTHER INFORMATION: RNA substrate

<400> SEQUENCE: 14
cuuguaauac caaugcuaua a                                                 21

<210> SEQ ID NO 15
<211> LENGTH: 20
<212> TYPE: RNA
<213> ORGANISM: artificial
<220> FEATURE:
<223> OTHER INFORMATION: RNA substrate

<400> SEQUENCE: 15
aaagaauacc aauguucucu                                                   20

<210> SEQ ID NO 16
<211> LENGTH: 20
<212> TYPE: RNA
<213> ORGANISM: artificial
<220> FEATURE:
<223> OTHER INFORMATION: RNA substrate

<400> SEQUENCE: 16
uaugaauacc auugcuuau                                                    20

<210> SEQ ID NO 17
<211> LENGTH: 20
<212> TYPE: RNA
<213> ORGANISM: artificial
<220> FEATURE:
<223> OTHER INFORMATION: RNA substrate

<400> SEQUENCE: 17
ccgaaugcca augcagaguu                                                   20

<210> SEQ ID NO 18
<211> LENGTH: 21
<212> TYPE: RNA
<213> ORGANISM: artificial
<220> FEATURE:
<223> OTHER INFORMATION: RNA substrate
```

```
<400> SEQUENCE: 18
gaugaaauac caauguuaac u                                      21

<210> SEQ ID NO 19
<211> LENGTH: 21
<212> TYPE: RNA
<213> ORGANISM: artificial
<220> FEATURE:
<223> OTHER INFORMATION: RNA substrate

<400> SEQUENCE: 19
cugaauacca augcugaacu u                                      21

<210> SEQ ID NO 20
<211> LENGTH: 20
<212> TYPE: RNA
<213> ORGANISM: artificial
<220> FEATURE:
<223> OTHER INFORMATION: RNA substrate

<400> SEQUENCE: 20
acagaauacc aaugcacaga                                        20
```

CHIRAL LIBRARY SCREEN

CLAIM OF PRIORITY

This application is a national stage application under 35 U.S.C. § 371 of PCT Application Nos. PCT/EP2015/079915, filed Dec. 16, 2015; PCT/EP2015/076971 filed Nov. 18, 2015 and PCT/EP2015/076967, filed Nov. 18, 2015, which claims priority to EP14198167.0, filed Dec. 16, 2014; EP15182401.8, filed Aug. 25, 2015; EP15191074.2, filed Oct. 22, 2015; EP15191075.9, filed Oct. 22, 2015, EP15191076.7, filed Oct. 22, 2015; EP15195198.5, filed Nov. 18, 2015; EP15195202.5, filed Oct. 18, 2015 each of these applications are hereby incorporated by reference in their entirety.

FIELD OF INVENTION

The invention relates to a method of identifying stereo-defined phosphorthioate oligonucleotide variants with reduced toxicity by creating and screening libraries of stereodefined chiral phosphorothioate variants for compounds with reduced toxicity, either in vitro or in vivo.

BACKGROUND

Koziolkiewicz et al. (NAR 1995 24; 5000-5005) discloses 15mer DNA phosphorothioate oligonucleotides where the phosphorothioate linkages are either [all-Rp] configuration, or [all-Sp] configuration, or a random mixture of diastereomers. The [all-Rp] was found to be "more susceptible to" RNAaseH dependent degradation compared to the hybrids or [all-Sp] oligonucleotides, and was found to have a higher duplex thermal stability. It is suggested that for practical application, the [all-Rp] oligos should be protected by [Sp] phosphorothioates at their 3' end.

Stec et al. (J. Am. Chem. Soc. 1998, 120; 7156-7167) reports on new monomers of 5'-DMT-deoxyribnucleoside 3'-O-(2-thio-"spiro"-4,4-pentamethylene-1,2,3-oxathiaphospholane) for use in stereocontrolled synthesis of PS-oligos via the oxathiaphospholane approach.

Karwowski et al. (Bioorganic & Med. Chem. Letts. 2001 11; 1001-1003) uses the oxathiaphospholane approach for the stereocontrolled synthesis of LNA dinucleoside phosphorothioates. The R stereoisomer dinucleotide was readily hydrolysed by snake venom phosphodiesterase.

Krieg et al. (Oligonucleotides 13; 491-499) investigated whether the immune stimulation by CpG PS-oligos depend on the chirality of their P-chirality. CpG PS Rp oligos showed much higher MAPK activation and induction of IκB degradation as compared to Sp oligos. There was no evidence for differential uptake of the different stereoisomer oligonucleotides. The Rp oligonucleotides had a shorter duration (less than 48 hours), probably due to rapid degradation. For immune stimulation, CpG oligos with Rp chirality are suggested for rapid short term use, and the Sp oligos for longer term effect.

Levin et al. Chapter 7 Antisense Drug Technology 2008; 183-215 reviews phosphorothioate chirality, confirming that the chirality of phosphorothioates DNA oligonucleotides greatly effects their pharmacokinetics, not least due to the exonuclease resistance of the Sp stereoisomer. The PK effects of phosphorothioate chirality are reported to be less significant in second generation ASOs due to the 2' modifications at the 3' and 5' termini which prevents exonuclease degradation, but it is likely that individual molecules which have Rp terminal residues may be more susceptible to exonucleases 4 i.e. for longer half-lives, the molecules with Sp residues at the termini are likely to have longer half-life.

Wave Life Sciences Poster (TIDES, May 3-6 2014, San Diego): Based on the calculation of 524,288 possible different stereoisomers within mipomersen they illustrate 7 stereoisomers which differ markedly with respect to $T_m$, RNAseH recruitment, lipophilicity, metabolic stability, efficacy in vivo, and specific activity.

Wan et al, Nucleic Acids Research, Nov. 14, 2014 (advanced publication), discloses 31 antisense oligonucleotides where the chirality of the gap region was controlled using the DNA-oxazaphospholine approach (Oka et al., J. Am. Chem. Soc. 2008; 16031-16037.), and concluded that controlling PS chirality in the gap region of gapmers provides no significant benefits for therapeutic applications relative to the mixture of stereo-random PS ASOs. Wan et al. further refers to the added complexity and costs associated with the synthesis and characterization of chiral PS ASOs as minimizing their utility.

Swayze et al., 2007, NAR 35(2): 687-700 reports that LNA antisense compounds improve potency but cause significant hepatotoxicity in animals. WO 2008/049085 reports on LNA mixed wing gapmers which comprise 2'-O-MOE in the LNA flanking regions, which apparently reduce the toxicity of certain LNA compounds, but significantly reduce the potency.

WO2014/012081 and WO2014/010250 provide chiral reagents for synthesis of oligonucleotides.

WO2015/107425 reports on the chiral designs of chirally defined oligonucleotides, and reports that certain chirally defined compounds can alter the RNaseH cleavage pattern.

SUMMARY OF INVENTION

The invention provides for a method of reducing the toxicity of an antisense oligonucleotide sequence (parent oligonucleotide), comprising the steps of a. Creating a library of stereodefined oligonucleotide variants (child oligonucleotides), retaining the core nucleobase sequence of the parent oligonucleotide.

b. Screening the library created in step a. for their in vitro or in vivo toxicity in a cell, c. Identify one or more stereodefined variants present in the library which has a reduced toxicity in the cell as compared to the parent oligonucleotide.

wherein, optionally the method is repeated (reiterative screening), for example so that the one or more stereodefined variants identified by the method is used as a parent oligonucleotide in the next round of the screening method. The term stereodefined is interchangeable with the term stereospecified herein.

The invention provides for a method of reducing the toxicity of a phosphorothioate oligonucleotide (parent) sequence, comprising the steps of:

a. Providing a stereo undefined phosphorothioate oligonucleotide (the parent) which has a toxicity phenotype in vivo or in vitro b. Creating a library of stereodefined phosphorothioate oligonucleotides (the children), retaining the core nucleobase sequence of the parent gapmer oligonucleotide c. Screening the library created in step b. in an in vivo or in vitro toxicity assay to d. Identify one or more stereodefined phosphorothioate oligonucleotides which have a reduced toxicity as compared to the stereo undefined phosphorothioate oligonucleotide In some embodiments, the method of the invention may be used reiteratively.

The methods of the invention may further comprise an additional subsequent step of manufacturing the one or more stereodefined phosphorothioate oligonucleotides which have a reduced toxicity. In some embodiments, the subsequent manufacture is in a scale of more than 1 g, such as more than 10 g. In some embodiments, the synthesis of the oligonucleotides for in vivo or in vitro screening steps (b) is performed at a scale of less than 1 g, such as less than 0.5 g, such as less than 0.1 g.

The child oligonucleotides (i.e. members of the library of step b) or the reduced toxicity child oligonucleotides identified by the method, are stereodefined variants of the parent oligonucleotide, i.e. they comprise of at least one stereodefined phosphorothioate internucleoside linkage which differs from parent.

In the method of the invention, each member of the library created in step b) comprises at least one stereodefined phosphorothioate internucleoside linkage which differs from parent.

In some embodiments, the method further comprises the step of determining the in vitro or in vivo potency of either the library of stereodefined oligonucleotide variants, or of the one or more stereodefined compounds present in the library identified in step c) or d).

In some embodiments, the method of the invention provides for a stereodefined phosphorothioate LNA oligonucleotide, comprising at least one stereoselective phosphorothioate linkage between a LNA nucleoside and a subsequent (3') nucleoside. Such an LNA oligonucleotide may for example be an LNA gapmer as described herein. The term stereodefined is used unchangeably with stereospecified herein). A stereodefined phosphorothioate linkage may also be referred to as a stereoselective or stereospecific phosphorothioate linkage.

In some embodiments the oligonucleotide of the invention is 10-20 nucleotides in length, such as 10-16 nucleotides in length.

Oligonucleotides which comprise at least one LNA nucleoside may be referred to as an LNA oligonucleotide or LNA oligomer herein.

The invention provides for a stereodefined phosphorothioate oligonucleotide which has a reduced toxicity in vivo or in vitro as compared to a non-stereodefined phosphorothioate oligonucleotide with the same nucleobase sequence and chemical modifications (other than the stereodefined phosphorothioate linkage(s)). In some embodiments, the non-stereodefined phosphorothioate oligonucleotide/stereodefined oligonucleotide may be a gapmer, such as a LNA-gapmer. For the comparison of toxicity, the stereodefined phosphorothioate oligonucleotide retains the pattern of modified and unmodified nucleosides present in the parent oligonucleotide.

The invention further provides a conjugate comprising the oligomer as described herein, which comprises at least one non-nucleotide or non-polynucleotide moiety ("conjugated moiety") covalently attached to the oligomer of the invention.

The invention provides for pharmaceutical compositions comprising an oligomer or conjugate as described herein, and a pharmaceutically acceptable solvent (such as water or saline water), diluent, carrier, salt or adjuvant.

Pharmaceutical and other compositions comprising an oligomer as described herein, are also provided. Further provided are methods of down-regulating the expression of a target nucleic acid, e.g. an RNA, such as a mRNA or microRNA in cells or tissues comprising contacting said cells or tissues, in vitro or in vivo, with an effective amount of one or more of the oligomers, conjugates or compositions as described herein.

Also disclosed are methods of treating an animal (a non-human animal or a human) suspected of having, or susceptible to, a disease or condition, associated with expression, or over-expression of a RNA by administering to the non-human animal or human a therapeutically or prophylactically effective amount of one or more of the oligomers, conjugates or pharmaceutical compositions as described herein.

The invention provides for methods of inhibiting (e.g., by down-regulating) the expression of a target nucleic acid in a cell or a tissue, the method comprising the step of contacting the cell or tissue, in vitro or in vivo, with an effective amount of one or more oligomers, conjugates, or pharmaceutical compositions thereof, to affect down-regulation of expression of a target nucleic acid.

In some embodiments, the LNA oligonucleotide as described herein, comprises at least one stereoselective phosphorothioate linkage between a LNA nucleoside and a subsequent (3') nucleoside.

In some embodiments, the LNA oligonucleotide as described herein, comprises at least one stereodefined phosphorothioate nucleotide pair wherein the internucleoside linkage between the nucleosides of the stereodefined phosphorothioate nucleotide pair is either in the Rp configuration or in the Rs configuration, and wherein at least one of the nucleosides of the stereodefined phosphorothioate nucleotide pair is a LNA nucleotide. In some embodiments, the other nucleoside of the stereodefined phosphorothioate nucleotide pair is other than DNA, such as nucleoside analogue, such as a further LNA nucleoside or a 2' substituted nucleoside. The invention also provides for the use of a stereospecified phosphorothioate internucleoside linkage in an oligonucleotide, wherein the oligonucleotide has a reduced toxicity as compared to an identical oligonucleotide which does not comprise the stereospecified phosphorothioate internucleotide linkage.

The invention also provides for the use of a stereocontrolling (also referred to as stereospecific) phosphorothioate monomer (e.g. phosphoramidite) for the synthesis for a reduced toxicity oligonucleotide (a stereodefined phosphorothioate oligonucleotide).

The invention also provides in vitro toxicity assays which have been found to be predictive for in vivo toxicity of oligonucleotides, such as LNA oligonucleotides. Suitable hepatotoxicity or nephrotoxicity assays are provided. It will be recognised that the use of such assays is not limited to stereodefined oligonucleotides, but in a separate aspect of the invention is applicable to oligonucleotides in general, such as antisense oligonucleotides, including LNA oligonucleotides (e.g. beta-D-oxy LNA or (S)cET for example), and oligonucleotides comprising 2'-substituted nucleosides, gapmer oligonucleotides, such as the oligonucleotide described herein.

The invention provides for the use of an in vitro primary hepatocyte assay to determine the (e.g. likely) hepatotoxicity of an oligonucleotide such as a LNA oligonucleotide.

The invention provides a method for predicting the (e.g. likely) in vivo hepatotoxicity of an oligonucleotide, such as a LNA oligonucleotide, said method comprising the steps of administering the oligonucleotide to a population of primary hepatocyte cells in vitro, such as a mouse or rat primary hepatocyte cells (which may be obtained by liver perfusion by example), or a human primary hepatocyte cell, incubating the cells in the presence of the oligonucleotide, e.g. for a period of between 1-7 days, such as 2-4 days, such as 3 days, and subsequently measuring at least one biomarker of in vitro cellular toxicity, such as those described herein, e.g. by measuring the amount of Lactate dehydrogenase (LDH) released into the culture media, and/or determination of cellular ATP levels. Suitably a reduction in cellular ATP levels is indicative of a hepatotoxic oligonucleotide, and elevation of LDH released into the culture media is indicative of a hepatotoxic oligonucleotide.

The invention provides for the use of an in vitro assay to determine the (e.g. likely) hepatotoxicity of an oligonucleotide such as a LNA oligonucleotide.

The invention provides for the use of an in vitro assay to determine the (e.g. likely) nephrotoxicity of an oligonucleotide such as a LNA oligonucleotide. Suitably, mammalian renal cortex epithelial cells may be used, such as human renal cortex epithelial cells, which may optionally be immortalised, e.g. hTERT1 such as RPTEC/TERT1 may be used (available from ATCC, e.g. (ATCC® CRL-4031™) or RPTEC-TERT1 (Evercyte GmbH, Austria).

The invention provides a method for predicting the (e.g. likely) in vivo nephrotoxicity of an oligonucleotide, such as a LNA oligonucleotide, said method comprising the steps of administering the oligonucleotide to a population of mammalian renal cortex epithelial cells in vitro, such as a human or rat primary proximal tubule epithelial cells, such as RPTEC-TERT1, incubating the cells in the presence of the oligonucleotide, e.g. for a period of between 1-21 days, such as 2-16 days, such as 4-12 days, such as 6-10 days, such as 9 days, and subsequently measuring at least one marker of in vitro cellular toxicity, such as those described herein, e.g. by determination of cellular ATP levels. Suitably a reduction in cellular ATP levels is indicative of a nephrotoxic oligonucleotide.

Suitably oligonucleotides are administered to the cell culture, e.g. in PBS, to achieve a final concentration of 1-100 µM, such as 5-50 µM, such as 10 or 30 µM.

It will be recognised that, in some embodiments, the methods for predicting the in vivo toxicity (e.g. nephrotoxicity or hepatotoxicity), may be used to identified stereodefined variants of a parent oligonucleotide which has reduced in vitro or in vivo toxicity.

FIGURES

FIG. 1: A schematic view of some LNA oligonucleotide of the invention. The figure shows a 3-10-3 gapmer oligonucleotide with 15 internucleoside phosphorothioate linkages. The internucleoside linkages in the wing regions X' and Y' may be as described herein, for example may be randomly Rp or Sp phosphorothioate linkages. The table part of FIG. 1 provides a parent compound (P) where all the internucleoside linkages of the gap region Y' are also randomly incorporated Rp or Sp phosphorothioate linkages (M), and in compounds 1-10, one of the phosphorothioate linkages is stereodefined as a Rp phosphorothioate internucleoside linkage (R).

Figure 2:
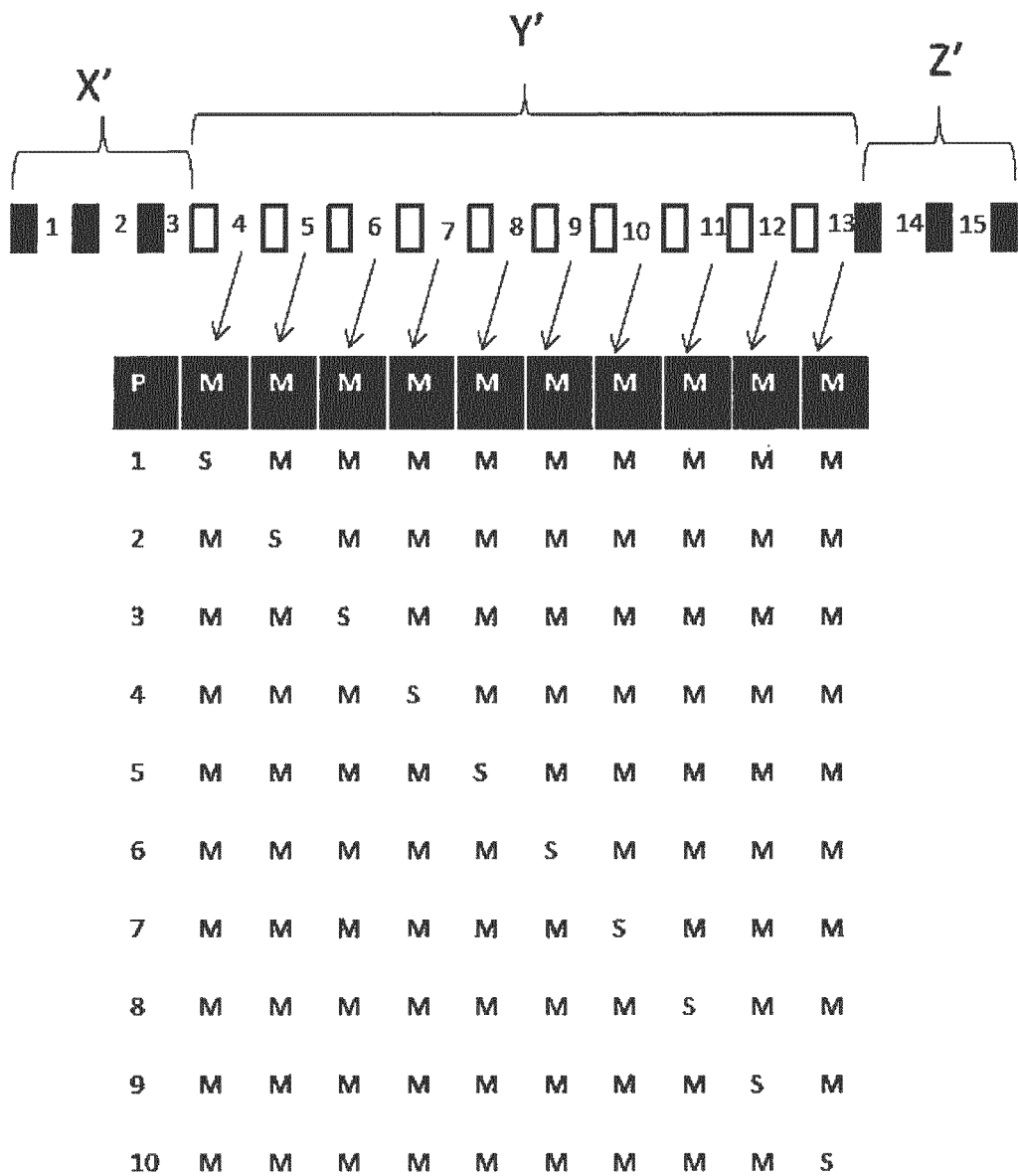

FIG. 2: As per FIG. 1, except in compounds 1-10, one of the phosphorothioate linkages is stereodefined as a Sp phosphorothioate internucleoside linkage (S).

Figure 3:
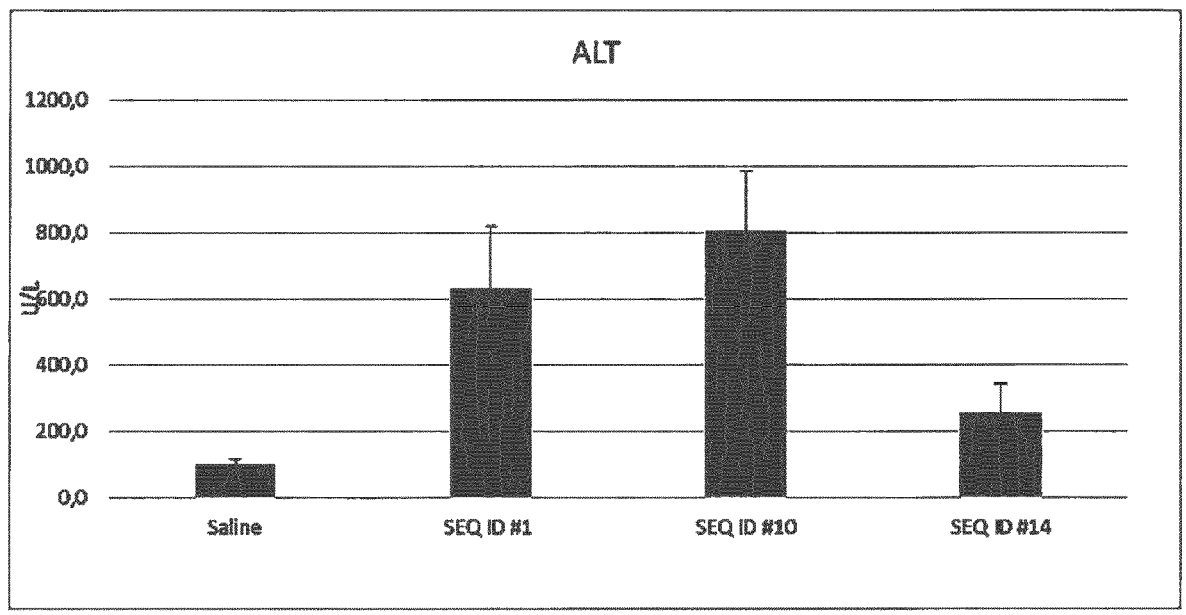

FIG. 3: The hepatotoxic potential (ALT) for LNA oligonucleotides where 3 phosphorothioate internucleoside linkages are fixed in either S (Comp #10) or R (Comp #14) configuration was compared to the ALT for parent mixture of diastereoisomers (Comp #1) with all internucleoside linkages as mixtures of R and S configuration.

Figure 4:
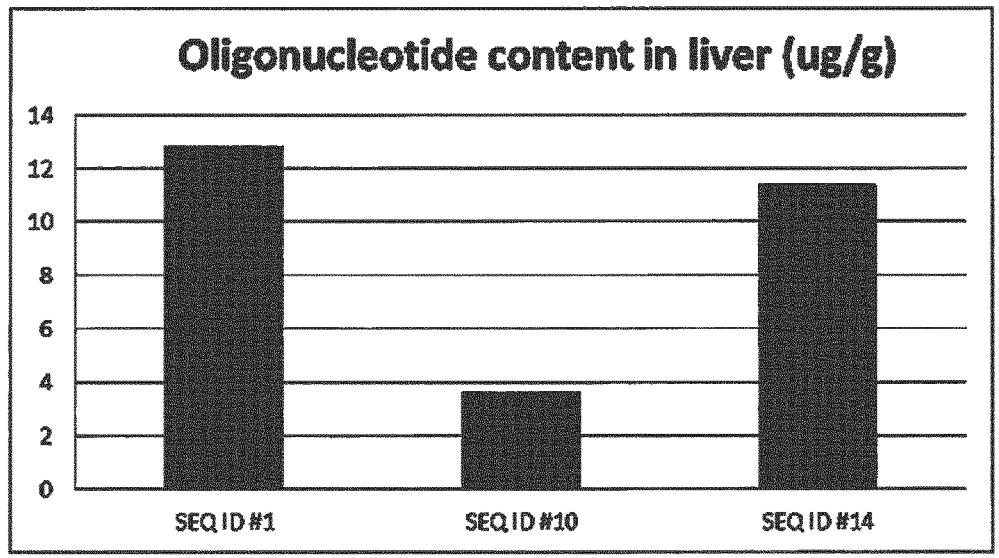
Figure 4:
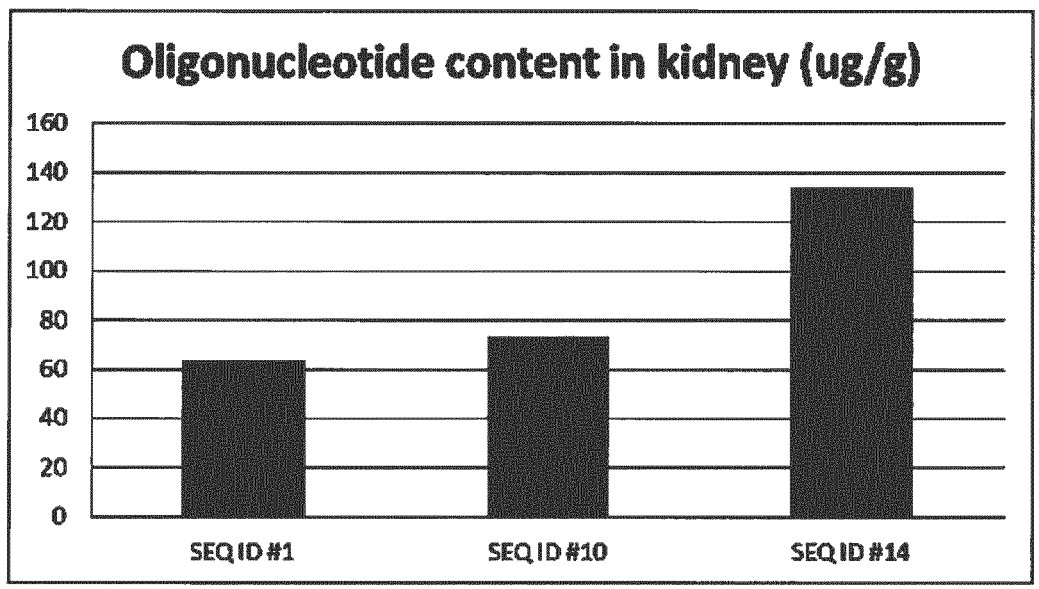
Figure 4:
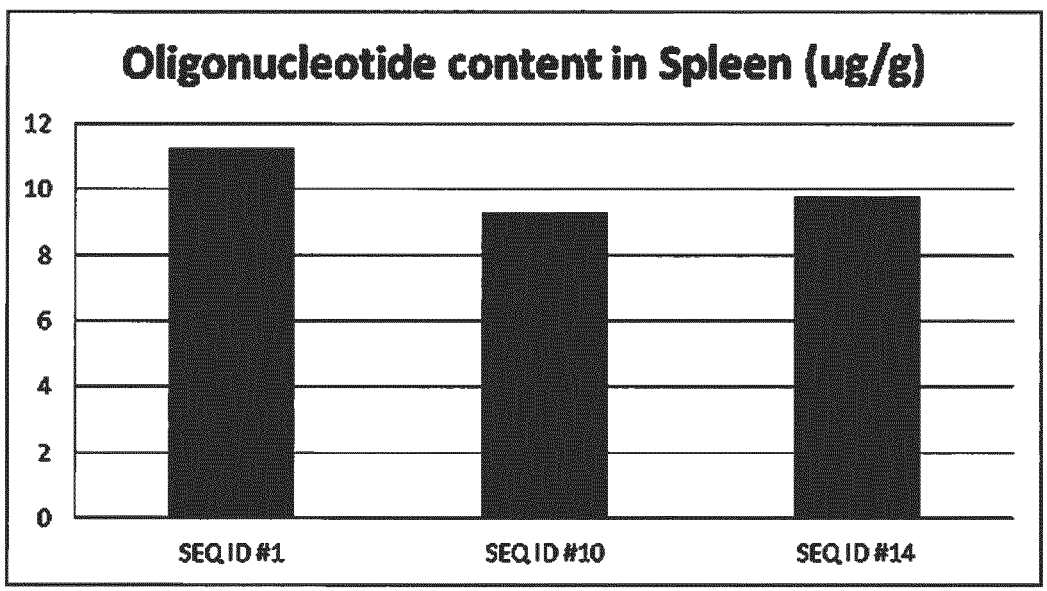

FIG. 4: Oligonucleotide content in liver, kidney, and spleen

Figure 5:
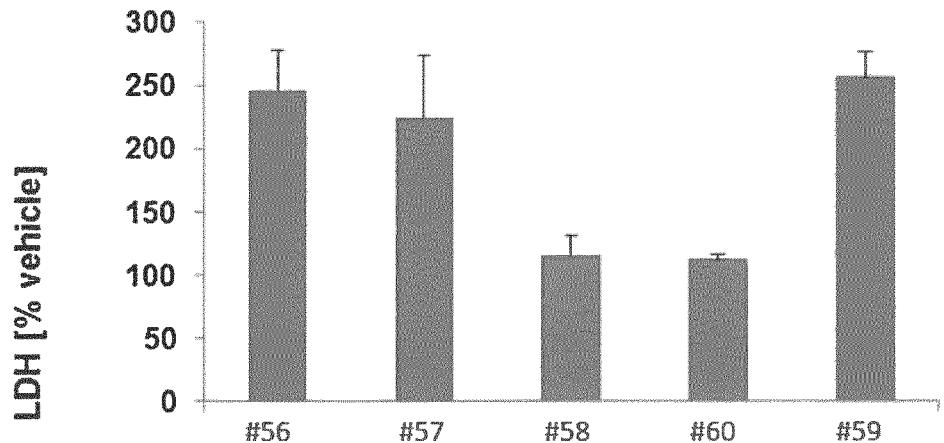
Figure 5:
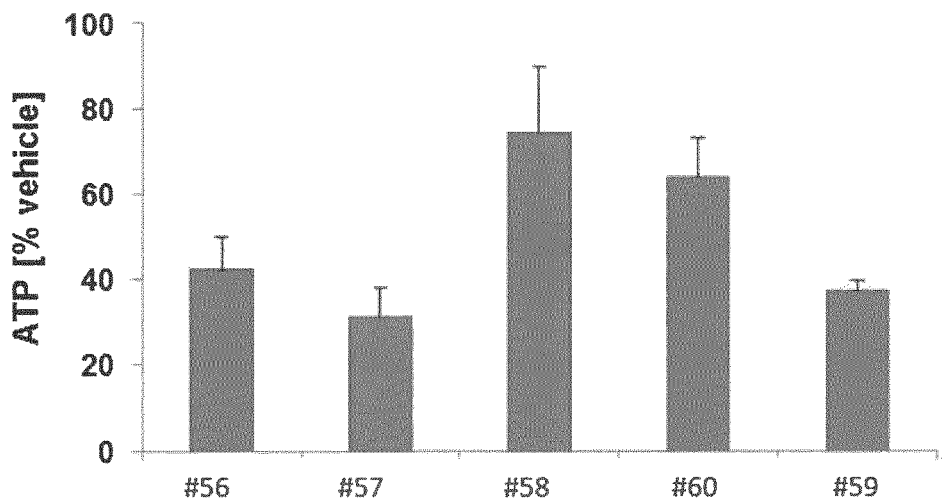
Figure 5:
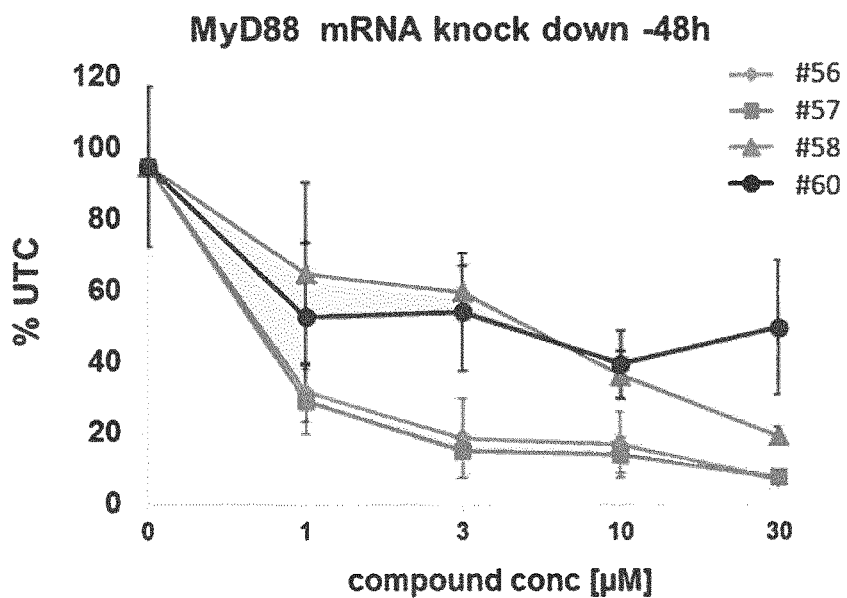

FIG. 5: Changes in LDH levels in the supernatants and intracellular ATP levels of cells treated for 3 days with the respective LNAs. Target knockdown (Myd88) was evaluated after 48 hours.

Figure 6:
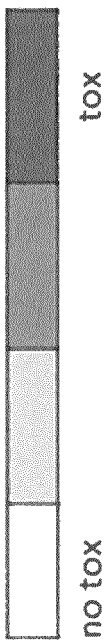

FIG. 6: In vitro toxicity screening in primary hepatocytes: Changes in LDH levels in the supernatants and intracellular ATP levels of cells treated for 3 days with the respective LNAs. Data are mean values and expressed as % vehicle control (n=4 experiments in triplicates for #56 and n=2 experiments in triplicates for all other LNAs).

Figure 7:
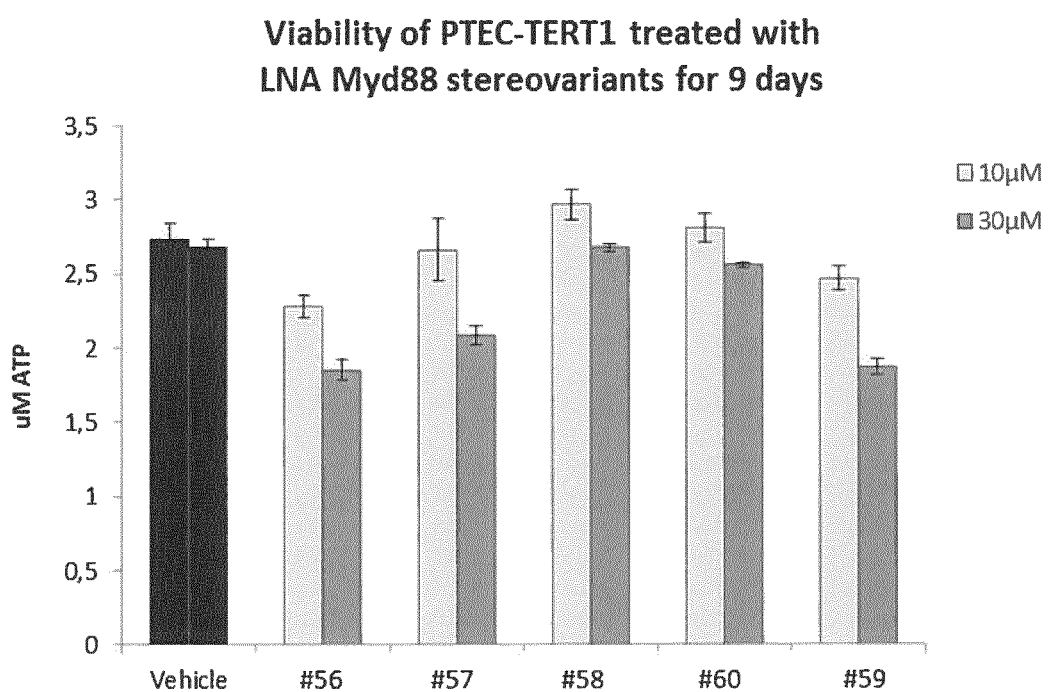

FIG. 7: In vitro toxicity screening in kidney proximal tubule cells: Viability of PTEC-TERT1 treated with LNA Myd88 stereovariants at 10 µM and 30 µM as measured after 9 days (cellular ATP).

DETAILED DESCRIPTION OF INVENTION

The method of the present invention provides stereospecified oligomeric compounds (also referred herein as oligomers or oligonucleotides) for use in modulating, such as inhibiting a target nucleic acid in a cell. The oligomers may be antisense gapmer oligonucleotides. The oligomers identified or manufactured using the methods of the invention have reduced in vitro or in vivo toxicity, such as reduced nephrotoxicity or reduced hepatotoxicity.

In the context of the present invention the term "stereodefined" refers to oligonucleotides where at least one phosphorothioate internucleoside linkage present in the oligonucleotide has defined stereochemistry, i.e. either Rp or Sp. In some embodiments the all of the phosphorothioate internucleoside linkages in a stereodefined oligonucleotide may be stereodefined, i.e. each phosphorothioate internucleoside linkage is independently selected from the group consisting of Rp and Sp phosphorothioate internucleoside linkages.

Typically, oligonucleotide phosphorothioates are synthesised as a random mixture of Rp and Sp phosphorothioate linkages (also referred to as a racemic mixture). In the present invention, gapmer phosphorothioate oligonucleotides are provided where at least one of the phosphorothioate linkages of the gap region oligonucleotide is stereodefined, i.e. is either Rp or Sp in at least 75%, such as at least 80%, or at least 85%, or at least 90% or at least 95%, or at least 97%, such as at least 98%, such as at least 99%, or (essentially) all of the oligonucleotide molecules present in the oligonucleotide sample. Such oligonucleotides may be referred as being stereodefined, stereoselective or stereospecified: They comprise at least one phosphorothioate linkage which is stereospecific. The terms stereodefined and stereospecified/stereoselective may be used interchangeably herein. The terms stereodefined, stereoselective and stereospecified may be used to describe a phosphorothioate internucleoside linkage (Rp or Sp), or may be used to described a oligonucleotide which comprises such a phosphorothioate internucleoside linkage. It is recognised that a stereodefined oligonucleotide may comprise a small amount of the alternative stereoisomer at any one position, for example Wan et al reports a 98% stereoselectivity for the gapmers reported in NAR, November 2014.

Advantages

In Vivo & In Vitro Optimisation

The present invention provides a method for optimising oligonucleotides, such as oligonucleotides identified by gene-walk for in vivo (e.g. pharmacological) utility. In particular the methods of the present invention may be used to reduce the in vitro or in vivo toxicity of an oligonucleotide (sequence), and in the synthesis and manufacture of oligomers with reduced toxicity, and optionally other enhanced beneficial properties, such as target specificity, mismatch discrimination, serum protein binding, biodistribution, RNaseH recruitment, potency, and cellular uptake.

Reduced Toxicity

The invention provides a method of reducing the toxicity of an antisense oligonucleotide sequence (parent oligonucleotide), comprising the steps of
  a. Creating a library of stereodefined oligonucleotide variants (child oligonucleotides), retaining the core nucleobase sequence of the parent oligonucleotide,
  b. Screening the library created in step a. for their in vitro or in vivo toxicity in a cell,
  c. Identify one or more stereodefined variants present in the library which has a reduced toxicity in the cell as compared to the parent oligonucleotide.

In some embodiments, the toxicity (step b) is determined in vivo. In some embodiments the toxicity is determined in vitro. In some embodiments the parent oligonucleotide is an oligonucleotide which has been determined to be hepatotoxic, either in vitro or in vivo. The child oligonucleotide(s) identified by the method of the invention have a reduced toxicity as compared to the parent oligonucleotide, for example a reduced hepatotoxicity.

In some embodiments the reduced toxicity is reduced hepatotoxicity. Hepatotoxicity of an oligonucleotide may be assess in vivo, for example in a mouse. In vivo hepatotoxicity assays are typically based on determination of blood serum markers for liver damage, such as ALT, AST or GGT. Levels of more than three times upper limit of normal are considered to be indicative of in vivo toxicity. In vivo toxicity may be evaluated in mice using, for example, a single 30 mg/kg dose of oligonucleotide, with toxicity evaluation 7 days later (7 day in vivo toxicity assay).

Suitable markers for cellular toxicity include elevated LDH, or a decrease in cellular ATP, and these markers may be used to determine cellular toxicity in vitro, for example using primary cells or cell cultures. For determination of hepatotoxicity, mouse or rat hepatocytes may be used, including primary hepatocytes. Suitable markers for toxicity in hepatocytes include elevated LDH, or a decrease in cellular ATP. Primary primate such as human hepatocytes may be used if available. In mammalian hepatocytes, such as mouse, an elevation of LDH is indicative of toxicity. A reduction of cellular ATP is indicative of toxicity, such as hepatotoxicity. In some embodiments the oligonucleotides of the invention have a reduced in vitro hepatotoxicity, as determined in primary mouse hepatocyte cells, e.g. using the assay provided in Example 8.

In some embodiments the reduced toxicity is reduced nephrotoxicity. Nephrotoxicity may be assessed in vivo, by the use of kidney damage markers including a rise in blood serum creatinine levels, or elevation of kim-1 (kidney injury marker-1) mRNA and/or protein. Suitably mice or rodents may be used.

In vitro kidney injury assays may be used to measure nephrotoxicity, and may include the elevation of kim-1 mRNA/protein, or changes in cellular ATP (decrease). In some embodiments, PTEC-TERT1 cells may be used to determine nephrotoxicity in vitro, for example by measuring cellular ATP levels. In some embodiments the oligonucleotides of the invention have a reduced in vitro nephrotoxicity, as determined in PTEC-TERT1 cells, e.g. using the assay provided in Example 9.

Other in vitro toxicity assays which may be used to assess toxicity include caspase assays, and cell viability assays, e.g. MTS assays. In some embodiments the reduced toxicity oligonucleotide of the invention comprises at least one stereodefined Rp internucleotide linkage, such as at least 2, 3, or 4 stereodefined Rp internucleotide linkage. The examples illustrate compounds which comprise stereodefined Rp internucleotide linkages that have a reduced hepatotoxicity in vitro and in vivo. In some embodiments, the at least one stereodefined Rp internucleotide linkage is present within the gap-region of a LNA gapmer. In some embodiments the reduced toxicity oligonucleotide of the invention comprises at least one stereodefined Sp internucleotide linkage, such as at least 2, 3, or 4 stereodefined Sp internucleotide linkage. The examples illustrate compounds which have a reduced nephrotoxicity which comprise at least one stereodefined Sp internucleoside linkage. In some embodiments, the at least one stereodefined Sp internucleotide linkage is present within the gap-region of a LNA gapmer.

The invention provides for the use of a stereocontrolled (may also be referred to as stereospecific, or stereospecifying) phosphoramidite monomer for the synthesis for a reduced toxicity oligonucleotide, e.g. reduced hepatotoxicity or reduced nephrotoxicity oligonucleotide. In some embodiments the stereocontrolled phosphoramidite monomer is a LNA stereocontrolled phosphoramidite monomer. In some embodiments the stereocontrolled phosphoramidite monomer is a DNA stereocontrolled phosphoramidite monomer. In some embodiments the stereocontrolled phosphoramidite monomer is a 2'modified stereocontrolled phosphoramidite monomer, such as a 2'methoxyethyl stereocontrolled phosphoramidite RNA monomer. Stereocontrolled phosphoramidite monomers may, in some embodiments, be oxazaphospholine monomers, such as DNA-oxazaphospholine LNA-oxazaphospholine monomers.

The monomers of the present invention may be used to reduce hepatotoxicity of LNA oligonucleotides in vitro or in vivo.

LNA hepatotoxicity may be determined using a model mouse system, see for example EP 1 984 381. The monomers of the present invention may be used to reduce nephrotoxicity of LNA oligonucleotides. LNA nephrotoxicity may be determined using a model rat system, and is often determined by the use of the Kim-1 biomarker (see e.g. WO 2014118267). The monomers of the present invention may be used to reduce the immunogenicity of an LNA oligomer in vivo. According to EP 1 984 381, LNAs with a 4'-CH$_2$—O-2' radicals are particularly toxic.

The oligonucleotides of the invention may have improved nuclease resistance, biostability, target affinity, RNaseH activity, and/or lipophilicity. As such the invention provides methods for both enhancing the activity of the oligomer in vivo and improvement of the pharmacological and/or toxicological profile of the oligomer.

In some embodiments, the LNA oligonucleotide has reduced toxicity as compared to an equivalent non stereoselective LNA oligonucleotide, e.g. reduced in vivo hepatotoxicity, for example as measured using the assay provided in example 6, or reduced in vitro hepatotoxicity, for example as measured using the assay provided in example 8, or reduced nephrotoxicity, for example as measured using the assay provided in example 9. Reduced toxicity may also be assessed using other methods known in the art, for example caspase assays and primary hepatocyte toxicity assays (e.g. example 8).

RNaseH Recruitment

As illustrated in the examples, in some embodiments, the stereodefined oligonucleotides of the invention have an enhanced RNaseH recruitment activity as compared to an otherwise non-stereodefined oligonucleotide (the parent oligonucleotide). Indeed, the present inventors were surprised to find that in general, the introduction of stereodefined phosphorothioate internucleoside linkages into a RNaseH recruiting LNA oligonucleotide, e.g. a LNA gapmer oligonucleotide, resulted in an enhanced RNaseH recruitment activity, up to 30× that of the parent (non-stereodefined). The invention therefore provides for the use of a stereocontrolled (also referred to as stereospecific) phosphoramidite monomer for the synthesis for an oligonucleotide with enhanced RNaseH recruitment activity as compared to an otherwise identical non-stereodefined oligonucleotide.

The invention may further comprise a method for enhancing the RNaseH recruitment activity of an antisense oligonucleotide sequence (parent oligonucleotide) for a RNA target, comprising the steps of:
a. Creating a library of stereodefined oligonucleotide variants (child oligonucleotides), retaining the core nucleobase sequence of the parent oligonucleotide
b. Screening the library created in step a. for their in vitro RNaseH recruitment activity against a RNA target,
c. Identify one or more stereodefined variants present in the library which has an enhanced RNaseH recruitment activity as compared to the parent oligonucleotide.
d. Optionally manufacturing at least one of the stereodefined variants identified in step c.

It will be recognised that this method may be combined with the method of reducing the toxicity of an oligonucleotide according to the invention.

The invention provides for an LNA oligonucleotide which has an enhanced RNaseH recruitment activity as compared to an otherwise identical non-stereodefined LNA oligonucleotide (or a parent oligonucleotide). The LNA oligonucleotide which has an enhanced RNaseH recruitment activity may further have a reduced in vitro or in vivo toxicity, such as reduced hepatotoxicity or reduced nephrotoxicity.

An otherwise identical non-stereodefined LNA oligonucleotide (e.g. a parent oligonucleotide) is a non-stereodefined phosphorothioate oligonucleotide with the same nucleobase sequence and chemical modifications, other than the stereodefined phosphorothioate linkage(s). It will be recognised that a non-stereodefined LNA oligonucleotide may comprise stereodefined centres in parts of the compound other than the phosphorothioate internucleotide linkages, e.g. within the nucleosides.

The use of chirally defined phosphorothioate linkages in LNA oligonucleotides surprisingly results in an increase in RNaseH activity. This may be seen when the gap-region comprises both stereodefined Rp and Sp internucleoside linkages. In some embodiments, the gap-region of the oligonucleotide of the invention comprises at least 2 Rp and at least 2 Sp stereodefined internucleoside linkages. In some embodiments the proportion of Rp vs. Sp stereodefined internucleoside linkages within gap region thereof (including internucleoside linkages adjacent to the wing regions), is between about 0.25 and about 0.75. In some embodiments, the gap-region of the oligonucleotide of the invention comprises at least 2 consecutive internucleoside linkages which are either stereodefined Rp or Sp internucleoside linkages. In some embodiments, the gap-region of the oligonucleotide of the invention comprises at least 3 consecutive internucleoside linkages which are either stereodefined Rp or Sp internucleoside linkages.

In some embodiments, the LNA oligonucleotide has an enhanced human RNaseH recruitment activity as compared to an equivalent non stereoselective LNA oligonucleotide, for example using the RNaseH recruitment assays provided in example 7. In some embodiments, the increase in RNaseH activity is at least 2×, such as at least 5×, such as at least 10× the RNaseH activity of the equivalent non stereoselective LNA oligonucleotide (e.g. parent oligonucleotide) Example 7 provides a suitable RNaseH assay which may be used to assess RNaseH activity (also referred to as RNaseH recruitment).

It has been found that a marked improvement in activity of RNaseH activity is found with LNA gapmer compounds where the gap region comprises both Rp and Sp internucleoside linkages, and in some embodiments, the gap region may comprise at least two Rp internucleoside linkages and at least two Sp internucleoside linkages, such as at least three Rp internucleoside linkages and/or at least three Sp internucleoside linkages.

It has been found that a marked improvement in activity of RNaseH activity is found with LNA gapmer compounds where the internucleoside linkages of the gap region are stereodefined. In some embodiments, therefore, there is at least one stereoselective phosphorothioate LNA oligonucleotide, comprising at least one stereoselective phosphorothioate linkage between a LNA nucleoside and a subsequent (3') nucleoside. In some embodiments at least one of the internucleotide linkages within region X' and/or Z' is is a Rp internucleoside linkage. In some embodiments, the 5' most internucleoside linkage in the oligomer or in region X' is a Sp internucleoside linkage. In some embodiments the flanking regions X' and Z' comprise at least one Sp internucleoside linkage and at least one Rp internucleoside linkage. In some embodiments the 3' internucleoside linkage of the oligomer or of region Z' is a Sp internucleoside linkage.

In some embodiments, the stereodefined oligonucleotide of the invention has improved potency as compared to an otherwise non-stereodefined oligonucleotide or parent oligonucleotide.

Specificity and Mismatch Discrimination

As illustrated in the examples, in some embodiments, the stereodefined oligonucleotides of the invention may have an enhanced mismatch discrimination (or enhanced target specificity) as compared to an otherwise non-stereodefined oligonucleotide (or parent oligonucleotide). Indeed, the present inventors were surprised to find that the introduction of stereodefined phosphorothioate internucleoside linkages into a RNaseH recruiting LNA oligonucleotide, e.g. a LNA gapmer oligonucleotide, may result in an enhanced mismatch discrimination (or target specificity). The invention therefore provides for the use of a stereocontrolling phosphorothioate monomer for the synthesis for an oligonucleotide with enhanced mismatch discrimination (or target specificity) as compared to an otherwise identical non-stereodefined oligonucleotide.

The invention may therefore further comprise a method of enhancing the mismatch discrimination (or target specificity) of an antisense oligonucleotide sequence (parent oligonucleotide) for a RNA target in a cell, comprising the steps of
a. Creating a library of stereodefined oligonucleotide variants (child oligonucleotides), retaining the core nucleobase sequence of the parent oligonucleotide
b. Screening the library created in step a. for their activity against the RNA target and their activity for at least one other RNA present,
c. Identify one or more stereodefined variants present in the library which has a reduced activity against the at least one other RNA as compared to parent oligonucleotide.

It will be recognised that this method may be combined with the method of reducing the toxicity of an oligonucleotide according to the invention.

The reduced activity against the at least one other RNA may be determined as a ratio of activity of the intended target/unintended target (at least one other RNA). This method may also be combined with the method for enhancing the RNaseH recruitment activity of an antisense oligonucleotide sequence (parent oligonucleotide) for a RNA target, to identify oligonucleotides of the invention which have both enhanced RNaseH recruitment activity and enhanced mismatch discrimination (i.e. enhanced targeted specificity), and reduced in vitro or in vivo toxicity.

The invention provides for an LNA oligonucleotide which has an enhanced mismatch discrimination (or enhanced target specificity) as compared to an otherwise identical non-stereodefined LNA oligonucleotide (or a parent oligonucleotide). The LNA oligonucleotide which has an enhanced mismatch discrimination (or enhanced target specificity) may further have a reduced in vitro or in vivo toxicity, such as reduced hepatotoxicity or reduced nephrotoxicity, and optionally an enhanced RNaseH recruitment activity.

The invention provides for an LNA oligonucleotide which has reduced in vivo or in vitro toxicity, and an enhanced RNaseH recruitment activity and an enhanced mismatch discrimination (or enhanced target specificity) as compared to an otherwise identical non-stereodefined LNA oligonucleotide (or a parent oligonucleotide).

The invention therefore provides for the use of a stereocontrolling/stereocontrolled (can also be referred to as a stereodefined or stereospecific) phosphoramidite monomer for the synthesis for an oligonucleotide with reduced toxicity, enhanced mismatch discrimination (or target specificity) and enhanced RNAseH recruitment activity as compared to an otherwise identical non-stereodefined oligonucleotide.

In some embodiments the stereocontrolling phosphoramidite monomer is a LNA stereocontrolling (stereospecific) phosphoramidite monomer. In some embodiments the stereocontrolling phosphoramidite monomer is a DNA stereocontrolling phosphoramidite monomer. In some embodiments the stereocontrolling (stereospecific) phosphoramidite monomer is a 2'modified stereocontrolling (stereospecific) phosphoramidite monomer, such as a 2'methoxyethyl stereocontrolling (stereospecific) phosphoramidite RNA monomer. stereocontrolling (stereospecific) phosphoramidite monomers may, in some embodiments, be oxazapholine monomers, such as DNA-oxazapholine LNA-oxazapholine monomers. In some embodiments, the stereocontrolling (stereospecific) phosphoramidite monomers may comprise a nucleobase selected from the group consisting of A, T, U, C, 5-methyl-C or G nucleobase.

Biodistribution

The invention provides a method of altering the biodistribution of an antisense oligonucleotide sequence (parent oligonucleotide), comprising the steps of
  a. Creating a library of stereodefined oligonucleotide variants (child oligonucleotides), retaining the core nucleobase sequence of the parent oligonucleotide,
  b. Screening the library created in step a. for their biodistribution
  c. Identify one or more stereodefined variants present in the library which has an altered (such as preferred) biodistribution as compared to the parent oligonucleotide.
  d. Optionally manufacturing the one or more stereodefined variants identified in step c.

The above method may be used in conjunction with the method of reducing the toxicity s disclosed herein.

It is recognized that in some embodiments, the parent oligonucleotide may be a mixture of different stereoisomeric forms, and as such the method of the invention may comprise a method of identifying individual stereodefined oligonucleotides, or individual stereoisomers (child oligonucleotides) which have one reduced toxicity, and optionally one or more other improved property, such as enhanced specificity, altered biodistribution, enhanced potency as compared to the patent oligonucleotide.

In some embodiments the compounds of the invention, or identified by the methods of the invention, have an enhanced biodistribution to the liver.

In some embodiments the compounds of the invention, or identified by the methods of the invention, have an enhanced liver/kidney biodistribution ratio.

In some embodiments the compounds of the invention, or identified by the methods of the invention, have an enhanced kidney/liver biodistribution ratio.

In some embodiments the compounds of the invention, or identified by the methods of the invention, have an enhanced biodistribution to the kidney.

In some embodiments the compounds of the invention, or identified by the methods of the invention, have an enhanced cellular uptake in hepatocytes.

In some embodiments the compounds of the invention, or identified by the methods of the invention, have an enhanced cellular uptake in kidney cells.

When referring to compounds with enhanced functional characteristics, the enhancement may be made with regards the parent oligonucleotide, such as an otherwise identical non-stereodefined oligonucleotide.

Whilst biodistribution studies are typically performed in vivo, they may also be performed in in vitro systems, by example by comparing the cellular uptake in different cell types, for examples in in vitro hepatocytes (e.g. primary hepatocytes) or renal cells (e.g. renal epithelial cells, such as PTEC-TERT1 cells).

Oligonucleotides

The term "oligomer" or "oligonucleotide" or "oligomeric compound" in the context of the present invention, refers to a molecule formed by covalent linkage of two or more nucleotides (i.e. an oligonucleotide). Herein, a single nucleotide (unit) may also be referred to as a monomer or unit. In some embodiments, the terms "nucleoside", "nucleotide", "unit" and "monomer" are used interchangeably. It will be recognized that when referring to a sequence of nucleotides or monomers, what is referred to is the sequence of bases, such as A, T, G, C or U. The term oligonucleotide is used interchangeably with the term oligomeric compound and oligomer herein.

In some embodiments the oligonucleotide is 10-20 nucleotides in length, such as 10, 11, 12, 13, 14, 15, 16, 17, 18, 19, 20 nucleotides. In some embodiments the parent and child oligonucleotide is an LNA oligomer. In some embodiments, the LNA oligomer comprises at least one stereoselective phosphorothioate linkage between a LNA nucleoside and a subsequent (3') nucleoside. In some embodiments, the LNA oligomer comprises at least one stereodefined phosphorothioate nucleotide pair wherein the internucleoside linkage between the nucleosides of the stereodefined phosphorothioate nucleotide pair is either in the Rp configuration or in the Rs configuration, and wherein at least one of the nucleosides of the nucleotide pair is a LNA nucleotide. In some embodiments, the other nucleotide of the nucleotide pair is other than DNA, such as nucleoside analogue, such as a further LNA nucleoside or a 2' substituted nucleoside.

In some embodiments, the oligomer is a stereodefined (stereoselective) phosphorothioate LNA oligonucleotide, comprising at least one stereoselective phosphorothioate linkage between a LNA nucleoside and a subsequent (3') nucleoside. Such an LNA oligonucleotide may for example be a LNA gapmer as described herein.

In some embodiment the oligonucleotide comprising a central region (Y') of at least 5 or more contiguous nucleosides, and a 5' wing region (X') comprising of 1-6 LNA nucleosides and a 3' wing region (Z') comprising of LNA 1-6 nucleosides, wherein at least one of the internucleoside linkages of central region are stereodefined, and wherein the central region comprises both Rp and Sp internucleoside linkages.

Parent Oligonucleotide

In some embodiments, the parent oligonucleotide may be a non-stereodefined phosphorothioate oligonucleotide, i.e. an oligonucleotide which comprises a mixture of individual molecules where the chirality of the phosphorothioate linkages are not defined, for example a racemic mixture. In other words, in some embodiments, the parent oligonucleotide may have only stereo unspecified phosphorothioate internucleoside linkages (i.e. a stereo-unspecified oligonucleotide).

In some embodiments the parent oligonucleotide comprises non-stereodefined phosphorothioate internucleoside linkages. In some embodiments, all of the internucleoside linkages present in the parent oligonucleotide are non-stereodefined internucleoside linkages, such as non-stereodefined internucleoside phosphorothioate linkages.

In some embodiments, the parent oligonucleotide may comprise one or more stereodefined phosphorothioate internucleoside linkages. In some embodiments, all of the phosphorothioate internucleoside linkages of the parent oligonucleotide are stereodefined phosphorothioate internucleoside linkages. In some embodiments, the parent oligonucleotide is identified by an earlier reiteration of the method of the invention.

Library of Variants

The method of the invention involves the step of creating a library of variants of the parent oligonucleotide, wherein the variants have at least one stereodefined phosphorothioate internucleoside linkage which differs from the parent oligonucleotide. Suitably, each member of the library of variants has a distinct pattern of defined stereodefined phosphorothioate internucleoside linkages which differ from the parent.

In some embodiments, each member of the library of child oligonucleotides (stereodefined defined oligonucleotide variants) comprises at least 2, such as at least 3, such as at least 4 stereodefined phosphorothioate linkages, wherein the remaining linkages may optionally be non-stereodefined defined phosphorothioate linkages. Suitably, the said at least 2, at least 3 or at least 4 stereospecified phosphorothioate linkages present in the child oligonucleotides differ from the parent (e.g. the parent does not comprise stereodefined phosphorothioate internucleoside linkages, or the parent comprises a different stereodefined phosphorothioate linkage, or a different pattern or stereodefined phosphorothioate linkage).

In some embodiments 5%, 10%, 15%, 20%, 25%, 30%, 35%, 40%, 45%, 50%, 55%, 60%, 65%, 70%, 75%, 80%, 85%, 90%, or 95% of the linkages in the (e.g. child) oligomer(s) are stereodefined phosphorothioate linkages. In some embodiments all of the phosphorothioate linkages in the (e.g. child) oligomer(s) are stereodefined phosphorothioate linkages. In some embodiments the all the internucleoside linkages of the (e.g. child) oligomer(s) are stereodefined phosphorothioate linkages. It should be recognised that stereodefined (stereospecificity) refers to the incorporation of a high proportion, i.e. at least 75%, of either the Rp or the Sp internucleoside linkage at a defined internucleoside linkage.

In some embodiments, in step b) of the method of the invention each member of the library of stereodefined oligonucleotide variants may be created by inserting at least one stereodefined phosphorothioate internucleoside linkage into the gap-region of a parent gapmer. Suitably, either the inserted stereodefined phosphorothioate internucleoside linkage differs from the equivalent internucleoside linkage of the parent, or the parent does not comprise a stereodefined internucleoside linkage at the equivalent position.

In some embodiments, each member of the library of stereodefined oligonucleotide variants is created by inserting at least one stereodefined phosphorothioate internucleoside linkage into the gap-region of the gapmer.

In some embodiments, each member of the library of stereodefined oligonucleotide variants is created by inserting at least one stereodefined phosphorothioate internucleoside linkage into one or both wing-regions of the gapmer.

In some embodiments, each member of the library of stereodefined oligonucleotide variants is created by inserting at least one stereodefined phosphorothioate internucleoside linkage into one or both wing-regions of the gapmer and at least one stereodefined phosphorothioate internucleoside linkage into the gap-region of the gapmer.

It will be recognised that in some embodiments, the remaining internucleoside linkages of a child oligonucleotide, such as the remaining internucleoside linkages of the gap region or of the gapmer compound, may be the same as the parent, or may in some embodiments be different to the parent.

In some embodiments, the child oligonucleotides created in step b) comprise 1, 2, 3, 4, 5, 6, 7, 8, 9, 10, 11, 12, 13, 14, 15, 16, 17, 18, 19 or 20 independently stereodefined phosphorothioate internucleoside linkages. In some embodiments, all of the phosphorothioate internucleoside linkages of the child oligonucleotides created in step b) are stereodefined phosphorothioate internucleoside linkages. In some embodiments, all of the internucleoside linkages of the child oligonucleotides created in step b) are stereodefined phosphorothioate internucleoside linkages.

In some embodiments, each member of the library of stereodefined defined oligonucleotide variants comprises at least 2, such as at least 3, such as at least 4 stereodefined phosphorothioate linkages, wherein the remaining linkages may optionally be non-stereodefined defined phosphorothioate linkages.

In some embodiments, all phosphorothioate linkages present in each member of the library of stereodefined defined oligonucleotide variants are stereodefined defined phosphorothioate linkages.

In some embodiments, all internucleoside linkages present in each member of the library of child oligonucleotides, or gapmer region thereof, are stereodefined phosphorothioate linkages.

In some embodiments, each member of the library of stereodefined defined oligonucleotide variants retains the pattern of modified and unmodified nucleosides present in the parent oligonucleotide, such as antisense gapmer oligonucleotide. In some embodiments, the parent and child oligonucleotides share the same pattern of nucleoside modifications, e.g. the (for example) gapmer design of the parent oligonucleotide is retained in the child oligonucleotides, or at least a proportion of the child oligonucleotides. However, it is recognised that the library of variants may comprise child oligonucleotides that, whilst retaining the overall gapmer design of the parent oligonucleotide, may comprise a few, such as 1 or 2 or 3 or 4 nucleosides where the sugar chemistry of the parent has also been varied, for example by use of an alternative nucleoside in the wing e.g. use of an alternative high affinity nucleoside in the wing regions, or a increase or decrease or shift in the gap region.

In some embodiments the parent and child oligonucleotides are LNA gapmer oligonucleotides.

Retaining the Core Nucleobase Sequence

A library of child oligonucleotides comprises 2 or more stereodefined phosphorothioate oligonucleotides which retain the core nucleobase sequence of the parent compound.

In some embodiments, the child oligonucleotides may be the same length as the parent oligonucleotide and retain the same nucleobase sequence. However, it is envisaged that, in some embodiments, the child oligonucleotides may be truncated, such as by the removal of a 5' and/or 3' terminal nucleotide, or may in some embodiments, have an additional nucleotide at the 5' and/or 3' end. Removal of one or more terminal high affinity nucleosides, such as a LNA nucleoside allows for the affinity of the oligonucleotide to the RNA target to be maintained, as the insertion of one or more LNA nucleosides into the gap region will increase the affinity to the RNA target. It is envisaged that, in some embodiments, the library of child oligonucleotides may comprise variants which have different flank regions, some being truncated, some having additional nucleosides, some having a sequence shifted one or two nucleosides (as measured to the RNA target), some with additional high affinity nucleosides in the flanks, so the library is a complex library of stereodefined phosphorothioate oligonucleotides with heterogeneous phosphorothioate internucleoside linkages, thereby allowing for the concurrent selection of child oligonucleotides which have a decreased toxicity as compared to the parent.

The parent and child oligonucleotides share a common core nucleobase sequence. The common core nucleobase sequence is typically at least 10 nucleobases long, such as at least 11, at least 12, at least 13, at least 14, at least 15, or at least 16 nucleobases long, and in some embodiments may be the same nucleobase sequence of the parent oligonucleotide. In some embodiments the parent and (at least a proportion of) the child oligonucleotides have the same nucleobase sequence across the length of the oligonucleotides. It is however envisaged that a proportion of the child oligonucleotides may, in some embodiments, comprise additional 5' or 3' nucleotides, such as and additional 1, 2 or 3 5' or 3' nucleotides. In addition or alternatively in some embodiments, a proportion of the child oligonucleotides may be truncated with regards the parent, e.g. may comprise 1, 2 or 3 nt truncation at the 5' or 3' end. In some embodiments, additional nucleobase or truncations of the nucleobase sequence of the (proportion of) child oligonucleotide(s) is a single nucleobase addition or truncation. In some embodiments, the child oligonucleotides, or a proportion thereof, may be shifted by a single nucleobase, or by 2 or 3 nucleobases in comparison to the parent oligonucleotide when aligned to the target sequence (in effect a truncation at one end, and an addition at the other). Additional nucleotides retain complementarity with the target nucleic acid sequence.

Gapmer Oligonucleotide

In some embodiments, the parent oligonucleotide and child oligonucleotide(s) are gapmer oligonucleotides. Gapmer oligonucleotides are widely used to inhibit a target RNA in a cell, such as a mRNA or viral RNA, via an antisense mechanism (and may therefore also be called antisense gapmer oligonucleotides). Gapmer oligonucleotides comprise a region of at least 5 contiguous nucleotides which are capable or recruiting RNaseH (gap region), such as a region of DNA nucleotides, e.g. 6-14 DNA nucleotides, flanked 5' and 3' by regions which comprise affinity enhancing modified nucleosides, such as LNA or 2' substituted nucleotides. In some embodiments, the flanking regions may be 1-8 nucleotides in length.

In some embodiments, the parent and child oligonucleotides are gapmer oligonucleotides which comprise a central region (Y') of at least 5 or more contiguous nucleosides, such as at least 5 contiguous DNA nucleosides, and a 5' wing region (X') comprising of 1-6 high affinity nucleoside analogues, such as LNA nucleosides and a 3' wing region (Z') comprising of 1-6 high affinity nucleoside analogues, such as LNA 1-6 nucleosides. An LNA gapmer oligonucleotide is an oligonucleotide which comprises at least one LNA nucleoside in the wing regions, and may for example comprise at least one LNA in both the 5' and 3' wing regions.

In some embodiments, the child oligonucleotides are gapmers wherein at least one of the internucleoside linkages of central region are stereodefined, and wherein the central region comprises both Rp and Sp internucleoside linkages.

A gapmer oligonucleotide may comprise a central region (Y') of at least 5 or more contiguous nucleosides capable of recruiting RNaseH, and a 5' wing region (X') comprising of 1-6 LNA nucleosides and a 3' wing region (Z') comprising of LNA 1-6 nucleosides. Suitably region Y' may have 6, 7, 8, 9, 10, 11, 12, 13 or 14 (e.g. 6-12) contiguous nucleotides, such as DNA nucleotides, and the nucleotides of regions X' and Z' adjacent to region Y' are LNA nucleotides. In some embodiments regions X' and Z' have 1-6 nucleotides at least one of which in each flank (X' and Z') are an LNA. In some embodiments all the nucleotides in region X' and region Z' are LNA nucleotides. In some embodiments the oligonucleotide of the invention comprises LNA and DNA nucleosides. In some embodiments, the oligonucleotide of the invention may be a mixed wing LNA gapmer where at least one of the LNA nucleosides in one of the wing regions (or at least one LNA in each wing) is replaced with a 2' substituted nucleoside, such as a 2'MOE nucleoside. In some embodiments the LNA gapmer does not comprise 2' substituted nucleosides in the wing regions. The internucleoside linkages between the nucleotides in the contiguous sequence of nucleotides of regions X'-Y'-Z' may be all phosphorothioate internucleoside linkages.

In some embodiments, in the child oligonucleotide(s) (and optionally the parent), at least one of the internucleoside linkages of central region are stereodefined, and wherein the central region comprises both Rp and Sp internucleoside linkages.

In some embodiments, in the child oligonucleotide(s) (and optionally the parent), the internucleoside linkages within region Y' are all stereodefined phosphorothioate internucleoside linkages. In some embodiments, in the child oligonucleotide(s) (and optionally the parent), the internucleoside linkages within region X' and Y' are stereodefined phosphorothioate internucleoside linkages. In some embodiments in the child oligonucleotide(s) (and optionally the parent), the internucleoside linkages between region X' and Y' and between region Y' and Z' are stereodefined phosphorothioate internucleoside linkages. In some embodiments in the child oligonucleotide(s) (and optionally the parent), all the internucleoside linkages within the contiguous nucleosides of regions X'-Y'-Z' are stereodefined phosphorothioate internucleoside linkages.

The introduction of at least one stereodefined phosphorothioate linkages in the gap region of an oligonucleotide may be used to modulate the biological profile of the oligonucleotide, for example it may modulate the toxicity profile. In some embodiments, 2, 3, 4 or 5 of the phosphorothioate linkages in the gap region in the child oligonucleotide(s) (and optionally the parent), are stereodefined. In some embodiments the remaining internucleoside linkages in the gap region are not stereodefined: They exist as a racemic mixture of Rp and Sp in the population of oligonucleotide species. In some embodiments in the child oligonucleotide(s) (and optionally the parent), the remaining internucleoside linkage in the oligonucleotide are not stereodefined. In some embodiments in the child oligonucleotide(s) (and optionally the parent), all the internucleoside linkages in the gap region are stereodefined. The gap region (referred to as Y') herein, is a region of nucleotides which is capable of recruiting RNaseH, and may for example be a region of at least 5 contiguous DNA nucleosides.

In some embodiments 1, 2, 3, 4, 5, 6, 7, 8, 9, 10, 11, 12, 13, or 14 of the linkages in the gap region of the oligomer are stereoselective phosphorothioate linkages.

In some embodiments 5%, 10%, 15%, 20%, 25%, 30%, 35%, 40%, 45%, 50%, 55%, 60%, 65%, 70%, 75%, 80%, 85%, 90%, or 95% of the linkages in the oligomer (e.g. gapmer) are stereoselective phosphorothioate linkages. In some embodiments all of the phosphorothioate linkages in the oligomer are stereoselective phosphorothioate linkages. In some embodiments the all the internucleoside linkages of the oligomer are stereodefined phosphorothioate linkages.

Efficacy

The child oligonucleotide(s) identified by the method of the invention may be tested as part of the method of the invention to determine that they are effective antisense oligonucleotides, such as they are capable of inhibiting their target nucleic acid. The method of the invention may therefore comprise an additional step of screening the library of child oligonucleotides (e.g. prior to, during or subsequent to step b) for their efficacy in modulating, e.g. inhibiting, their target. Alternatively, the method of the invention may comprise an additional step of testing the selected stereodefined variants with a reduced toxicity to determine their efficacy as an antisense oligonucleotide. In some embodiments, efficacy is determined by the oligonucleotides ability to recruit RNaseH, or in some embodiments may be the ability to modulate the expression of the target in a cell, in vitro, or in some embodiments, in vivo.

It is recognized that it is not necessary that the selected child oligonucleotides with reduced toxicity maintain the in vitro or in vivo potency of the parent oligonucleotide, but it is preferred that they are effective antisense oligonucleotides which have a reduced toxicity. Suitably, when evaluated in vivo, the therapeutic index of the oligonucleotide may be enhanced. Therapeutic index is typically calculated as the maximum tolerated dose (MTD) (e.g. for hepatotoxicity three times upper limit of normal) divided by the $ED_{50}$. For experimental purposes, assuming the target sequence is present in mice, MTD and $ED_{50}$ may be determined in mice in a seven day mouse study. If sequence conservation in mice is unfavourable, other model species may be used, e.g. rat, monkey, dog or pig.

In some embodiments, the selected child oligonucleotide(s) identified in step c. retain at least 25% such as at least 50%, such as at least 75%, such as at least 90% of the in vitro (e.g. $IC_{50}$) or in vivo (e.g. $ED_{50}$ or $EC_{50}$) potency of that of the parent. In some embodiments, the selected child oligonucleotide(s) identified in step c. have a similar in vitro (e.g. $IC_{50}$) or in vivo (e.g. $ED_{50}$ or $EC_{50}$) potency of that of the parent (i.e. +/−10%), or have an enhanced in vitro (e.g. $IC_{50}$) or in vivo (e.g. $ED_{50}$ or $EC_{50}$) potency of that of the parent. The $IC_{50}$ or $ED_{50}$ should be evaluated in target cells which are expressing the intended target.

In some embodiments, the child oligonucleotide identified in step c. have an improved $EC_{50}$ value of the parent compound. In some embodiments, the child oligonucleotide identified in step c. retain a similar $EC_{50}$ value of the parent compound (i.e. +/−10%). In some embodiments, the child oligonucleotide identified in step c. have an improved $EC_{50}$ value of the parent compound.

In some embodiments, the child oligonucleotide identified in step c. have no greater that a two fold higher (2×), or in some embodiments a three fold higher (3×) $EC_{50}$ value of the parent compound (i.e. +/−10%). In some embodiments, the child oligonucleotide identified in step c. retain an $EC_{50}$ value of not larger than 3 to 10 times that of the parent compound.

LNA

In some embodiments the parent and child oligonucleotides are LNA oligonucleotides, they comprise at least one LNA nucleoside.

LNA monomers (also referred to as bicyclic nucleic acids, BNA) are nucleosides where there is a biradical between the 2' and 4' position of the ribose ring. The 2'-4' biradical is also referred to as a bridge. LNA monomers, when incorporated into a oligonucleotides are known to enhance the binding affinity of the oligonucleotide to a complementary DNA or RNA sequence, typically measured or calculated as an increase in the temperature required to melt the oligonucleotide/target duplex ($T_m$).

An LNA oligomer comprises at least one "Locked Nucleic Acid" (LNA) nucleoside, such as a nucleoside which comprises a covalent bridge (also referred to a radical) between the 2' and 4' position (a 2'-4' bridge). LNA nucleosides are also referred to as "bicyclic nucleosides". The LNA oligomer is typically a single stranded antisense oligonucleotide.

In some embodiments the LNA oligomer comprises or is a gapmer. In some embodiments, the nucleoside analogues present in the oligomer are all LNA.

In various embodiments, the compound of the invention does not comprise RNA (units). In some embodiments, the oligomer has a single contiguous sequence which is a linear molecule or is synthesized as a linear molecule. The oligomer may therefore be single stranded molecule. In some embodiments, the oligomer does not comprise short regions of, for example, at least 3, 4 or 5 contiguous nucleotides, which are complementary to equivalent regions within the same oligomer (i.e. duplexes). The oligomer, in some embodiments, may be not (essentially) double stranded. In some embodiments, the oligomer is essentially not double stranded, such as is not a siRNA. In some embodiments, the oligomeric compound is not in the form of a duplex with a (substantially) complementary oligonucleotide—e.g. is not an siRNA.

The Target

The target of an oligonucleotide is typically a selected nucleic acid to which the oligonucleotide is capable of hybridising under physiological conditions. For antisense therapy the target nucleic acid is indicated in a medical disorder. The target nucleic acid may be, for example a mRNA or a microRNA (encompassed by the term target gene). Such an oligonucleotide is referred to as an antisense oligonucleotide.

Suitably the oligonucleotide (oligomer) used in the method or produced by the method of the invention is capable of down-regulating (e.g. reducing or removing) expression of the a target nucleic acid (also referred to as a target gene). In this regards, they can affect the inhibition of the target gene, typically in a mammalian such as a human cell. In some embodiments, the oligomers bind to the target nucleic acid and affect inhibition of expression of at least 10% or 20% compared to the normal expression level, more preferably at least a 30%, 40%, 50%, 60%, 70%, 80%, 90% or 95% inhibition compared to the normal expression level (such as the expression level in the absence of the oligomer(s) or conjugate(s)). In some embodiments, such modulation is seen when using from 0.04 and 25 nM, such as from 0.8 and 20 nM concentration of the compound of the invention. In the same or a different embodiment, the inhibition of expression is less than 100%, such as less than 98% inhibition, less than 95% inhibition, less than 90% inhibition, less than 80% inhibition, such as less than 70% inhibition. Modulation of expression level may be determined by measuring protein levels, e.g. by the methods such as SDS-PAGE followed by western blotting using suitable antibodies raised against the target protein. Alternatively, modulation of expression levels can be determined by measuring levels of mRNA, e.g. by northern blotting or quantitative RT-PCR. When measuring via mRNA levels, the level of down-regulation when using an appropriate dosage, such as from 0.04 and 25 nM, such as from 0.8 and 20 nM concentration, is, In some embodiments, typically to a level of from 10-20% the normal levels in the absence of the compound, conjugate or composition of the invention.

The oligonucleotides may therefore be used to down-regulate or inhibiting the expression of a target protein and/or target RNA in a cell which is expressing the target protein and/or RNA, said method comprising administering the oligomer or conjugate according to the invention to said cell to down-regulating or inhibiting the expression of the target protein or RNA in said cell. Suitably the cell is a mammalian cell such as a human cell. The administration may occur, in some embodiments, in vitro. The administration may occur, in some embodiments, in vivo.

The oligomers may comprise or consist of a contiguous nucleotide sequence which corresponds to the reverse complement of a nucleotide sequence present in the target nucleic acid.

In determining the degree of "complementarity" between oligomers of the invention (or regions thereof) and the target region of the nucleic acid the degree of "complementarity" (also, "homology" or "identity") is expressed as the percentage identity (or percentage homology) between the sequence of the oligomer (or region thereof) and the sequence of the target region (or the reverse complement of the target region) that best aligns therewith. The percentage is calculated by counting the number of aligned bases that are identical between the 2 sequences, dividing by the total number of contiguous monomers in the oligomer, and multiplying by 100. In such a comparison, if gaps exist, it is preferable that such gaps are merely mismatches rather than areas where the number of monomers within the gap differs between the oligomer of the invention and the target region.

As used herein, the terms "homologous" and "homology" are interchangeable with the terms "identity" and "identical".

The terms "corresponding to" and "corresponds to" refer to the comparison between the nucleotide sequence of the oligomer (i.e. the nucleobase or base sequence) or contiguous nucleotide sequence (a first region) and the equivalent contiguous nucleotide sequence of a further sequence selected from either i) a sub-sequence of the reverse complement of the nucleic acid target, such as the mRNA which encodes the target protein. WO2014/118267 provides numerous target mRNAs which are of therapeutic relevance, as well as oligomer sequences which may be optimised using the present invention (see e.g. table 3, the NCBI Genbank references are as disclosed in WO2014/118257)

TABLE 3

| The oligonucleotide may target a nucleic acid (e.g. mRNA encoding, or miRNA) selected from the groups consisting of | For the treatment of a disease or disorder such as |
|---|---|
| AAT | AAT-LivD |
| ALDH2 | Alcohol dependence |
| HAMP pathway | Anemia or inflammation/CKD |
| Apo(a) | Atherosclerosis/high Lp(a) |
| Myc | Liver cancer |
| 5'UTR | HCV |
| 5'UTR & NS5B | HCV |
| NS3 | HCV |
| TMPRSS6 | Hemochromatosis |
| Antithrombin III | Hemophilia A, B |
| ApoCIII | Hypertriglyceridemia |
| ANGPLT3 | Hyperlipidaemia |
| MTP | Hyperlipidaemia |
| DGAT2 | NASH |
| ALAS1 | Porphyria |
| Antithrombin III | Rare Bleeding disorders |
| Serum amyloid A | SAA-amyloidosis |
| Factor VII | Thrombosis |
| Growth hormone receptor | Acromegaly |
| ApoB-100 | Hypercholesterolemia |
| ApoCIII | Hypertriglyceridemia |
| PCSK9 | Hypercholesterolemia |
| CRP | Inflammatory disorders |
| KSP or VEGF | Liver cancer |
| PLK1 | Liver cancer |
| FGFR4 | Obesity |
| Factor IXa | Thrombosis |
| Factor XI | Thrombosis |
| TTR | TTR amyloidosis |
| GCCR | Type 2 diabetes |
| PTP-1B | Type 2 diabetes |
| GCGR | Cushing's Syndrome |
| Hepatic Glucose 6-Phosphate Transporter-1 | glucose homeostasis, diabetes, type 2 diabetes |

The terms "corresponding nucleotide analogue" and "corresponding nucleotide" are intended to indicate that the nucleotide in the nucleotide analogue and the naturally occurring nucleotide are identical. For example, when the 2-deoxyribose unit of the nucleotide is linked to an adenine, the "corresponding nucleotide analogue" contains a pentose unit (different from 2-deoxyribose) linked to an adenine.

The terms "reverse complement", "reverse complementary" and "reverse complementarity" as used herein are interchangeable with the terms "complement", "complementary" and "complementarity".

Length

The oligomer may consists or comprises of a contiguous nucleotide sequence of from 7-30, such as 7-26 or 8-25, such as 9, 10, 11, 12, 13, 14, 15, 16, 17, 18, 19, 20, 21, 22, 23, 24, 25 nucleotides in length, such as 10-20 nucleotides in length. In some embodiments, the length of the LNA oligomer is 10-16 nucleotides, such as 12, 13 or 14 nucleosides.

In some embodiments, the oligomers comprise or consist of a contiguous nucleotide sequence of a total of from 10-22, such as 12-18, such as 13-17 or 12-16, such as 13, 14, 15, 16 contiguous nucleotides in length.

In some embodiments, the oligomers comprise or consist of a contiguous nucleotide sequence of a total of 10, 11, 12, 13, or 14 contiguous nucleotides in length.

In some embodiments, the oligomer according to the invention consists of no more than 22 nucleotides, such as no more than 20 nucleotides, such as no more than 18 nucleotides, such as 15, 16 or 17 nucleotides. In some embodiments the oligomer of the invention comprises less than 20 nucleotides. It should be understood that when a range is given for an oligomer, or contiguous nucleotide sequence length it includes the lower an upper lengths provided in the range, for example from (or between) 10-30, includes both 10 and 30.

In some embodiments, the oligomers has a length of less than 20, such as less than 18, such as 16 nts or less or 15 or 14 nts or less. LNA oligomers often have a length less than 20.

In some embodiments, the oligomers comprise or consist of a contiguous nucleotide sequence of a total of 10, 11, 12, 13, or 14 contiguous nucleotides in length.

In some embodiments, the oligomer according to the invention consists of no more than 22 nucleotides, such as no more than 20 nucleotides, such as no more than 18 nucleotides, such as 15, 16 or 17 nucleotides. In some embodiments the oligomer of the invention comprises less than 20 nucleotides. It should be understood that when a range is given for an oligomer, or contiguous nucleotide sequence length it includes the lower an upper lengths provided in the range, for example from (or between) 10-30, includes both 10 and 30.

Screening Method

The invention provides for a method of reducing the toxicity of a stereo unspecified phosphorothioate oligonucleotide sequence, comprising the steps of:
a. Providing a stereo unspecified phosphorothioate oligonucleotide (the parent) which has a toxicity phenotype in vivo or in vitro
b. Creating a library of stereo specified phosphorothioate oligonucleotides (the children), retaining the core nucleobase sequence of the parent gapmer oligonucleotide
c. Screening the library created in step b. in an in vivo or in vitro toxicity assay to
d. Identify one or more stereo specified phosphorothioate oligonucleotides which have a reduced toxicity as compared to the stereo unspecified phosphorothioate oligonucleotide.

The stereo specified phosphorothioate oligonucleotides may be as according to the oligonucleotides of the invention, as disclosed herein. In some embodiments, the parent oligonucleotide is a gapmer oligonucleotide, such as a LNA gapmer oligonucleotide as disclosed herein. In some embodiments, the library of stereo specified phosphorothioate oligonucleotides comprises of at least 2, such as at least 5 or at least 10 or at least 15 or at least 20 stereospecified phosphorothioate oligonucleotides.

The screening method may further comprise a step of screening the children oligonucleotides for at least one other functional parameter, for example one or more of RNaseH recruitment activity, RNase H cleavage specificity, target specificity, target binding affinity, and/or in vivo or in vitro potency.

The method of the invention may therefore be used to reduce the toxicity associated with the parent oligonucleotide. Toxicity of oligonucleotides may be evaluated in vitro or in vivo. In vitro assays include the caspase assay (see e.g. the caspase assays disclosed in WO2005/023995) or hepatocyte toxicity assays (see e.g. Soldatow et al., Toxicol Res (Camb). 2013 Jan. 1; 2(1): 23-39.). In vivo toxicities are often identified in the pre-clinical screening, for example in mouse or rat. In vivo toxicity be for hepatotoxicity, which is typically measured by analysing liver transaminase levels in blood serum, e.g. ALT and/or AST, or may for example be nephrotoxicity, which may be assayed by measuring a molecular marker for kidney toxicity, for example blood serum creatinine levels, or levels of the kidney injury marker mRNA, kim-1.

The selected child oligonucleotides identified by the screening method are therefore safer effective antisense oligonucleotides.

Gap Regions with Stereodefined Phosphorothioate Linkages

As reported in Wan et al., there is little benefit is introducing fully Rp or fully Sp gap regions in a gapmer, as compared to a random racemic mixture of phosphorothioate linkages. The present invention is based upon the surprising benefit that the introduction of at least one stereodefined phosphorothioate linkage may substantially improve the biological properties of an oligonucleotide, e.g. reduced toxicity. This may be achieved by either introducing one or a number, e.g. 2, 3, 4, 5, 6, 7, 8, 9, 10, 11, 12, 13 or 14 stereodefined phosphorothioate linkages, or by stereo specifying all the phosphorothioate linkages in the gap region.

In some embodiments, only 1, 2, 3, 4 or 5 of the internucleoside linkages of the central region (Y') are stereoselective phosphorothioate linkages, and the remaining internucleoside linkages are randomly Rp or Sp.

In some embodiments, all of the internucleoside linkages of the central region (Y') are stereoselective phosphorothioate linkages.

In some embodiments, the central region (Y') comprises at least 5 contiguous phosphorothioate linked DNA nucleoside. In some embodiments, the central region is at least 8 or 9 DNA nucleosides in length. In some embodiments, the central region is at least 10 or 11 DNA nucleosides in length. In some embodiments, the central region is at least 12 or 13 DNA nucleosides in length. In some embodiments, the central region is at least 14 or 15 DNA nucleosides in length.

Stereo-Selective DNA Motifs

We have previously identified that certain DNA dinucleotides may contribute to the toxicity profile of antisense oligonucleotides (Hagedorn et al., Nucleic Acid Therapeutics 2013, 23; 302-310). In some embodiments of the invention, the toxicity of the DNA dinucleotides in antisense oligonucleotides, such as the LNA gapmer oligonucleotides described herein, may be modulated via introducing stereoselective phosphorothioate internucleoside linkages between the DNA nucleosides of DNA dinucleotides, particularly dinucleotides which are known to contribute to toxicity, e.g. hepatotoxicity. In some embodiments the oligonucleotide identified by the method of the invention comprises a DNA dinucleotide motif selected from the group consisting of cc, tg, tc, ac, tt, gt, ca and gc, wherein the internucleoside linkage between the DNA nucleosides of the dinucleotide is a stereodefined phosphorothioate linkage such as either a Sp or a Rp phosphorothioate internucleoside linkage. Typically such dinucleotides may be within the gap region of a gapmer oligonucleotide, such as a LNA gapmer oligonucleotide. In some embodiments the oligonucleotide identified by the method comprises at least 2, such as at least 3 dinucleotides dependently or independently selected from the above list of DNA dinucleotide motifs.

RNAse Recruitment

It is recognised that an oligomeric compound may function via non RNAse mediated degradation of target mRNA, such as by steric hindrance of translation, or other methods, In some embodiments, the oligomers of the invention are capable of recruiting an endoribonuclease (RNase), such as RNase H.

It is preferable such oligomers, comprise a contiguous nucleotide sequence (region Y'), comprises of a region of at least 6, such as at least 7 consecutive nucleotide units, such as at least 8 or at least 9 consecutive nucleotide units (residues), including 7, 8, 9, 10, 11, 12, 13, 14, 15 or 16 consecutive nucleotides, which, when formed in a duplex with the complementary target RNA is capable of recruiting RNase. The contiguous sequence which is capable of recruiting RNAse may be region Y' as referred to in the context of a gapmer as described herein. In some embodiments the size of the contiguous sequence which is capable of recruiting RNAse, such as region Y', may be higher, such as 10, 11, 12, 13, 14, 15, 16, 17, 18, 19 or 20 nucleotide units.

EP 1 222 309 provides in vitro methods for determining RNaseH activity, which may be used to determine the ability to recruit RNaseH. A oligomer is deemed capable of recruiting RNase H if, when provided with the complementary RNA target, it has an initial rate, as measured in pmol/l/min, of at least 1%, such as at least 5%, such as at least 10% or, more than 20% of the of the initial rate determined using DNA only oligonucleotide, having the same base sequence but containing only DNA monomers, with no 2' substitutions, with phosphorothioate linkage groups between all monomers in the oligonucleotide, using the methodology provided by Example 91-95 of EP 1 222 309.

In some embodiments, an oligomer is deemed essentially incapable of recruiting RNaseH if, when provided with the complementary RNA target, and RNaseH, the RNaseH initial rate, as measured in pmol/l/min, is less than 1%, such as less than 5%, such as less than 10% or less than 20% of the initial rate determined using the equivalent DNA only oligonucleotide, with no 2' substitutions, with phosphorothioate linkage groups between all nucleotides in the oligonucleotide, using the methodology provided by Example 91-95 of EP 1 222 309.

In other embodiments, an oligomer is deemed capable of recruiting RNaseH if, when provided with the complementary RNA target, and RNaseH, the RNaseH initial rate, as measured in pmol/l/min, is at least 20%, such as at least 40%, such as at least 60%, such as at least 80% of the initial rate determined using the equivalent DNA only oligonucleotide, with no 2' substitutions, with phosphorothioate linkage groups between all nucleotides in the oligonucleotide, using the methodology provided by Example 91-95 of EP 1 222 309.

Typically the region of the oligomer which forms the consecutive nucleotide units which, when formed in a duplex with the complementary target RNA is capable of recruiting RNase consists of nucleotide units which form a DNA/RNA like duplex with the RNA target. The oligomer of the invention, such as the first region, may comprise a nucleotide sequence which comprises both nucleotides and nucleotide analogues, and may be e.g. in the form of a gapmer, a headmer or a tailmer.

A "headmer" is defined as an oligomer that comprises a region X' and a region Y' that is contiguous thereto, with the 5'-most monomer of region Y' linked to the 3'-most monomer of region X'. Region X' comprises a contiguous stretch of non-RNase recruiting nucleoside analogues and region Y' comprises a contiguous stretch (such as at least 7 contiguous monomers) of DNA monomers or nucleoside analogue monomers recognizable and cleavable by the RNase.

A "tailmer" is defined as an oligomer that comprises a region X' and a region Y' that is contiguous thereto, with the 5'-most monomer of region Y linked to the 3'-most monomer of the region X'. Region X' comprises a contiguous stretch (such as at least 7 contiguous monomers) of DNA monomers or nucleoside analogue monomers recognizable and cleavable by the RNase, and region X' comprises a contiguous stretch of non-RNase recruiting nucleoside analogues.

In some embodiments, in addition to enhancing affinity of the oligomer for the target region, some nucleoside analogues also mediate RNase (e.g., RNaseH) binding and cleavage. Since α-L-LNA (BNA) monomers recruit RNaseH activity to a certain extent, in some embodiments, gap regions (e.g., region Y' as referred to herein) of oligomers containing α-L-LNA monomers consist of fewer monomers recognizable and cleavable by the RNaseH, and more flexibility in the mixmer construction is introduced.

Gapmer Design

In some embodiments, the oligomer of the invention, comprises or is a LNA gapmer. A gapmer oligomer is an oligomer which comprises a contiguous stretch of nucleotides which is capable of recruiting an RNAse, such as RNAseH, such as a region of at least 5, 6 or 7 DNA nucleotides, referred to herein in as region Y' (Y'), wherein region Y' is flanked both 5' and 3' by regions of affinity enhancing nucleotide analogues, such as from 1-6 affinity enhancing nucleotide analogues 5' and 3' to the contiguous stretch of nucleotides which is capable of recruiting RNAse—these regions are referred to as regions X' (X') and Z' (Z') respectively. Examples of gapmers are disclosed in WO2004/046160, WO2008/113832, and WO2007/146511. The LNA gapmer oligomers of the invention comprise at least one LNA nucleoside in region X' or Z', such as at least one LNA nucleoside in region X' and at least one LNA nucleotide in region Z'.

In some embodiments, the monomers which are capable of recruiting RNAse are selected from the group consisting of DNA monomers, alpha-L-LNA monomers, C4' alkylated DNA monomers (see PCT/EP2009/050349 and Vester et al., Bioorg. Med. Chem. Lett. 18 (2008) 2296-2300, hereby incorporated by reference), and UNA (unlinked nucleic acid) nucleotides (see Fluiter et al., Mol. Biosyst., 2009, 10, 1039 hereby incorporated by reference). UNA is unlocked nucleic acid, typically where the C2-C3 C—C bond of the ribose has been removed, forming an unlocked "sugar" residue. Preferably the gapmer comprises a (poly)nucleotide sequence of formula (5' to 3'), X'-Y'-Z', wherein; region X' (X') (5' region) consists or comprises of at least one high affinity nucleotide analogue, such as at least one LNA unit, such as from 1-6 affinity enhancing nucleotide analogues, such as LNA units, and; region Y' (Y') consists or comprises of at least five consecutive nucleotides which are capable of recruiting RNAse (when formed in a duplex with a complementary RNA molecule, such as the mRNA target), such as DNA nucleotides, and; region Z' (Z') (3' region) consists or comprises of at least one high affinity nucleotide analogue, such as at least one LNA unit, such as from 1-6 affinity enhancing nucleotide analogues, such as LNA units.

In some embodiments, region X' comprises or consists of 1, 2, 3, 4, 5 or 6 LNA units, such as 2-5 LNA units, such as 3 or 4 LNA units; and/or region Z' consists or comprises of 1, 2, 3, 4, 5 or 6 LNA units, such as from 2-5 LNA units, such as 3 or 4 LNA units.

In some embodiments, region X' may comprises of 1, 2, 3, 4, 5 or 6 2' substituted nucleotide analogues, such as 2'MOE; and/or region Z' comprises of 1, 2, 3, 4, 5 or 6 2'substituted nucleotide analogues, such as 2'MOE units.

In some embodiments, the substituent at the 2' position is selected from the group consisting of: F; $CF_3$, CN, $N_3$, NO, $NO_2$, O-, S-, or N-alkyl; O-, S-, or N-alkenyl; O-, S- or N-alkynyl; or O-alkyl-O-alkyl, O-alkyl-N-alkyl or N-alkyl-O-alkyl wherein the alkyl, alkenyl and alkynyl may be substituted or unsubstituted $C_1$-$C_{10}$ alkyl or $C_2$-$C_{10}$ alkenyl and alkynyl. Examples of 2' substituents include, and are not limited to, $O(CH_2)$ $OCH_3$, and $O(CH_2)$ $NH_2$, wherein n is from 1 to about 10, e.g. MOE, DMAOE, DMAEOE.

In some embodiments Y' consists or comprises of 5, 6, 7, 8, 9, 10, 11 or 12 consecutive nucleotides which are capable of recruiting RNAse, or from 6-10, or from 7-9, such as 8 consecutive nucleotides which are capable of recruiting RNAse. In some embodiments region Y' consists or comprises at least one DNA nucleotide unit, such as 1-12 DNA units, preferably from 4-12 DNA units, more preferably from 6-10 DNA units, such as from 7-10 DNA units, such as 8, 9 or 10 DNA units.

In some embodiments region X' consist of 3 or 4 nucleotide analogues, such as LNA, region X' consists of 7, 8, 9 or 10 DNA units, and region Z' consists of 3 or 4 nucleotide analogues, such as LNA. Such designs include (X'-Y'-Z') 3-10-3, 3-10-4, 4-10-3, 3-9-3, 3-9-4, 4-9-3, 3-8-3, 3-8-4, 4-8-3, 3-7-3, 3-7-4, 4-7-3.

Further gapmer designs are disclosed in WO2004/046160, which is hereby incorporated by reference. WO2008/113832, which claims priority from U.S. provisional application 60/977,409 hereby incorporated by reference, refers to 'shortmer' gapmer oligomers. In some embodiments, oligomers presented here may be such shortmer gapmers.

In some embodiments the oligomer, e.g. region X', is consisting of a contiguous nucleotide sequence of a total of 10, 11, 12, 13 or 14 nucleotide units, wherein the contiguous nucleotide sequence comprises or is of formula (5'-3'), X'-Y'-Z' wherein; X' consists of 1, 2 or 3 affinity enhancing nucleotide analogue units, such as LNA units; Y' consists of 7, 8 or 9 contiguous nucleotide units which are capable of recruiting RNAse when formed in a duplex with a complementary RNA molecule (such as a mRNA target); and Z' consists of 1, 2 or 3 affinity enhancing nucleotide analogue units, such as LNA units.

In some embodiments the oligomer, comprises of a contiguous nucleotide sequence of a total of 10, 11, 12, 13, 14, 15 or 16 nucleotide units, wherein the contiguous nucleotide sequence comprises or is of formula (5'-3'), X'-Y'-Z' wherein; X' comprises of 1, 2, 3 or 4 LNA units; Y' consists of 7, 8, 9 or 10 contiguous nucleotide units which are capable of recruiting RNAse when formed in a duplex with a complementary RNA molecule (such as a mRNA target) e.g. DNA nucleotides; and Z' comprises of 1, 2, 3 or 4 LNA units.

In some embodiments X' consists of 1 LNA unit. In some embodiments X' consists of 2 LNA units. In some embodiments X' consists of 3 LNA units. In some embodiments Z' consists of 1 LNA units. In some embodiments Z' consists of 2 LNA units. In some embodiments Z' consists of 3 LNA units. In some embodiments Y' consists of 7 nucleotide units. In some embodiments Y' consists of 8 nucleotide units. In some embodiments Y' consists of 9 nucleotide units. In certain embodiments, region Y' consists of 10 nucleoside monomers. In certain embodiments, region Y' consists or comprises 1-10 DNA monomers. In some embodiments Y' comprises of from 1-9 DNA units, such as 2, 3, 4, 5, 6, 7, 8 or 9 DNA units. In some embodiments Y' consists of DNA units. In some embodiments Y' comprises of at least one LNA unit which is in the alpha-L configuration, such as 2, 3, 4, 5, 6, 7, 8 or 9 LNA units in the alpha-L-configuration. In some embodiments Y' comprises of at least one alpha-L-oxy LNA unit or wherein all the LNA units in the alpha-L-configuration are alpha-L-oxy LNA units. In some embodiments the number of nucleotides present in X'-Y'-Z' are selected from the group consisting of (nucleotide analogue units—region Y'—nucleotide analogue units): 1-8-1, 1-8-2, 2-8-1, 2-8-2, 3-8-3, 2-8-3, 3-8-2, 4-8-1, 4-8-2, 1-8-4, 2-8-4, or; 1-9-1, 1-9-2, 2-9-1, 2-9-2, 2-9-3, 3-9-2, 1-9-3, 3-9-1, 4-9-1, 1-9-4, or; 1-10-1, 1-10-2, 2-10-1, 2-10-2, 1-10-3, 3-10-1. In some embodiments the number of nucleotides in X'-Y'-Z' are selected from the group consisting of: 2-7-1, 1-7-2, 2-7-2, 3-7-3, 2-7-3, 3-7-2, 3-7-4, and 4-7-3. In certain embodiments, each of regions X' and Y' consists of three LNA monomers, and region Y' consists of 8 or 9 or 10 nucleoside monomers, preferably DNA monomers. In some embodiments both X' and Z' consists of two LNA units each, and Y' consists of 8 or 9 nucleotide units, preferably DNA units. In various embodiments, other gapmer designs include those where regions X' and/or Z' consists of 3, 4, 5 or 6 nucleoside analogues, such as monomers containing a 2'-O-methoxyethyl-ribose sugar (2'-MOE) or monomers containing a 2'-fluoro-deoxyribose sugar, and region Y' consists of 8, 9, 10, 11 or 12 nucleosides, such as DNA monomers, where regions X'-Y'-Z' have 3-9-3, 3-10-3, 5-10-5 or 4-12-4 monomers. Further gapmer designs are disclosed in WO 2007/146511A2, hereby incorporated by reference.

In the gapmer designs reported herein the gap region (Y') may comprise one or more stereodefined phosphorothaiote linkage, and the remaining internucleoside linkages of the gap region may e.g. be non-stereodefined internucleoside linkages, or may also be stereodefined phosphorothioate linkages.

Internucleotide Linkages

The oligomer identified by the method of the invention comprises at least one stereodefined phosphorothioate linkage. Whilst the majority of compounds used for therapeutic use phosphorothioate internucleotide linkages, it is possible to use other internucleoside linkages. However, in some embodiments all the internucleoside linkages of the oligomer of the invention are phosphorothioate internucleoside linkages. In some embodiments the linkages in the gap region are all phosphorothioate and the internucleoside linkages of the wing regions may be either phosphorothioate or phosphodiester linkages.

The nucleoside monomers of the oligomer described herein are coupled together via [internucleoside] linkage groups. Suitably, each monomer is linked to the 3' adjacent monomer via a linkage group.

The person having ordinary skill in the art would understand that, in the context of the present invention, the 5' monomer at the end of an oligomer does not comprise a 5' linkage group, although it may or may not comprise a 5' terminal group.

The terms "linkage group" or "internucleotide linkage" are intended to mean a group capable of covalently coupling together two nucleotides. Specific and preferred examples include phosphate groups and phosphorothioate groups.

The nucleotides of the oligomer of the invention or contiguous nucleotides sequence thereof are coupled together via linkage groups. Suitably each nucleotide is linked to the 3' adjacent nucleotide via a linkage group.

Suitable internucleotide linkages include those listed within WO2007/031091, for example the internucleotide linkages listed on the first paragraph of page 34 of WO2007/031091 (hereby incorporated by reference).

It is, in some embodiments, it is desirable to modify the internucleotide linkage from its normal phosphodiester to one that is more resistant to nuclease attack, such as phosphorothioate or boranophosphate—these two, being cleavable by RNase H, also allow that route of antisense inhibition in reducing the expression of the target gene.

Suitable sulphur (S) containing internucleotide linkages as provided herein may be preferred, such as phosphorothioate or phosphodithionate.

For gapmers, the internucleotide linkages in the oligomer may, for example be phosphorothioate or boranophosphate so as to allow RNase H cleavage of targeted RNA. Phosphorothioate is usually preferred, for improved nuclease resistance and other reasons, such as ease of manufacture.

WO09124238 refers to oligomeric compounds having at least one bicyclic nucleoside (LNA) attached to the 3' or 5' termini by a neutral internucleoside linkage. The oligomers of the invention may therefore have at least one bicyclic nucleoside attached to the 3' or 5' termini by a neutral internucleoside linkage, such as one or more phosphotriester, methylphosphonate, MMI, amide-3, formacetal or thioformacetal. The remaining linkages may be phosphorothioate.

Stereocontrolled Monomer

A stereocontrolled monomer is a monomer used in oligonucleotide synthesis which confers a stereodefined phosphorothioate internucleoside linkage in the oligonucleotide, i.e. either the Sp or Rp. In some embodiments the monomer may be a amidite such as a phosphoramidite. Therefore monomer may, in some embodiments be a stereocontrolling/controlled amidite, such as a stereocontrolling/controlled phosphoramidite. Suitable monomers are provided in the examples, or in the Oka et al., J. AM. CHEM. SOC. 2008, 130, 16031-16037 9 16031. See also WO10064146, WO 11005761, WO 13012758, WO 14010250, WO 14010718, WO 14012081, and WO 15107425. The term stereocontrolled/stereocontrolling are used interchangeably herein and may also be referred to stereospecific/stereospecified or stereodefined monomers.

As the stereocontrolled monomer may therefore be referred to as a stereocontrolled "phosphorothioate" monomer. The term stereocontrolled and stereocontrolling are used interchangeably herein. In some embodiments, a stereocontrolling monomer, when used with a sulfurizing agent during oligonucleotide synthesis, produces a stereodefined internucleoside linkage on the 3' side of the newly incorporated nucleoside (or 5'-side of the grown oligonucleotide chain).

Nucleosides and Nucleoside Analogues

In some embodiments, the terms "nucleoside analogue" and "nucleotide analogue" are used interchangeably.

The term "nucleotide" as used herein, refers to a glycoside comprising a sugar moiety, a base moiety and a covalently linked group (linkage group), such as a phosphate or phosphorothioate internucleotide linkage group, and covers both naturally occurring nucleotides, such as DNA or RNA, and non-naturally occurring nucleotides comprising modified sugar and/or base moieties, which are also referred to as "nucleotide analogues" herein. Herein, a single nucleotide (unit) may also be referred to as a monomer or nucleic acid unit.

In field of biochemistry, the term "nucleoside" is commonly used to refer to a glycoside comprising a sugar moiety and a base moiety, and may therefore be used when referring to the nucleotide units, which are covalently linked by the internucleotide linkages between the nucleotides of the oligomer. In the field of biotechnology, the term "nucleotide" is often used to refer to a nucleic acid monomer or unit, and as such in the context of an oligonucleotide may refer to the base—such as the "nucleotide sequence", typically refer to the nucleobase sequence (i.e. the presence of the sugar backbone and internucleoside linkages are implicit). Likewise, particularly in the case of oligonucleotides where one or more of the internucleoside linkage groups are modified, the term "nucleotide" may refer to a "nucleoside" for example the term "nucleotide" may be used, even when specifying the presence or nature of the linkages between the nucleosides.

As one of ordinary skill in the art would recognise, the 5' terminal nucleotide of an oligonucleotide does not comprise a 5' internucleotide linkage group, although may or may not comprise a 5' terminal group.

Non-naturally occurring nucleotides include nucleotides which have modified sugar moieties, such as bicyclic nucleotides or 2' modified nucleotides, such as 2' substituted nucleotides.

"Nucleotide analogues" are variants of natural nucleotides, such as DNA or RNA nucleotides, by virtue of modifications in the sugar and/or base moieties. Analogues could in principle be merely "silent" or "equivalent" to the natural nucleotides in the context of the oligonucleotide, i.e. have no functional effect on the way the oligonucleotide works to inhibit target gene expression. Such "equivalent" analogues may nevertheless be useful if, for example, they are easier or cheaper to manufacture, or are more stable to storage or manufacturing conditions, or represent a tag or label. Preferably, however, the analogues will have a functional effect on the way in which the oligomer works to inhibit expression; for example by producing increased binding affinity to the target and/or increased resistance to intracellular nucleases and/or increased ease of transport into the cell. Specific examples of nucleoside analogues are described by e.g. Freier & Altmann; *Nucl. Acid Res.,* 1997, 25, 4429-4443 and Uhlmann; *Curr. Opinion in Drug Development,* 2000, 3(2), 293-213, and in Scheme 1:

Scheme 1

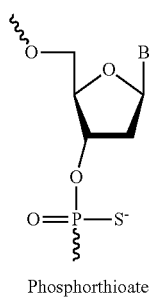

Phosphorthioate

-continued
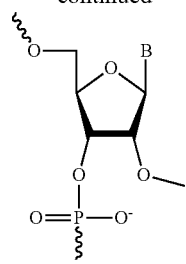
2'-O-Methyl
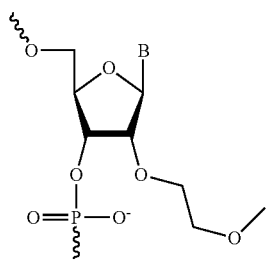
2'-MOE
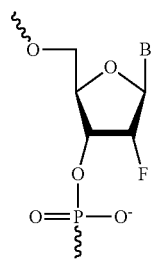
2'-Fluoro
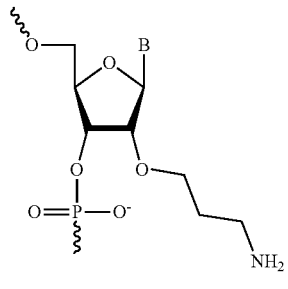
2'-AP
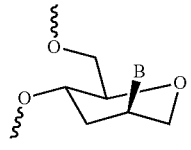
HNA
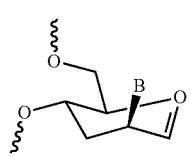
CeNA
-continued
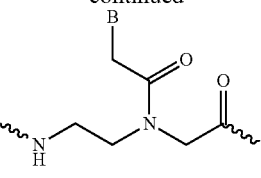
PNA
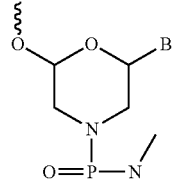
Morpholine
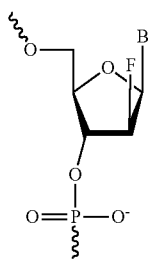
2'-F-ANA
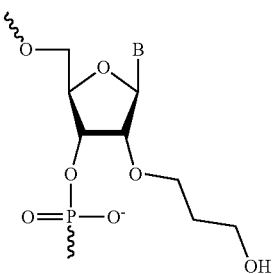
2'-(3-hydroxy)propyl
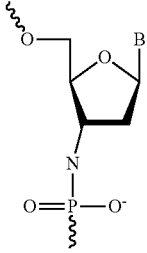
3'-Phosphoramidate
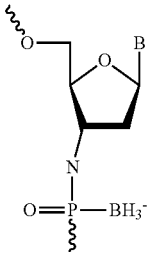
Boranophosphates The oligomer may thus comprise or consist of a simple sequence of natural occurring nucleotides—preferably 2'-deoxynucleotides (referred to here generally as "DNA"), but also possibly ribonucleotides (referred to here generally as "RNA"), or a combination of such naturally occurring nucleotides and one or more non-naturally occurring nucleotides, i.e. nucleotide analogues. Such nucleotide analogues may suitably enhance the affinity of the oligomer for the target sequence.

Examples of suitable and preferred nucleotide analogues are provided by WO2007/031091 or are referenced therein.

Incorporation of affinity-enhancing nucleotide analogues in the oligomer, such as LNA or 2'-substituted sugars, can allow the size of the specifically binding oligomer to be reduced, and may also reduce the upper limit to the size of the oligomer before non-specific or aberrant binding takes place. Oligomers of the method of the invention refer to the parent and child oligonucleotides.

In some embodiments, the parent and child oligonucleotides comprises at least 1 nucleotide analogue. In some embodiments the parent and child oligonucleotides comprises at least 2 nucleotide analogues. In some embodiments, the parent and child oligonucleotides comprises from 3-8 nucleotide analogues, e.g. 6 or 7 nucleotide analogues. In some embodiments, at least one of said nucleotide analogues is a locked nucleic acid (LNA); for example at least 3 or at least 4, or at least 5, or at least 6, or at least 7, or 8, of the nucleotide analogues may be LNA. In some embodiments all the nucleotides analogues may be LNA.

It will be recognised that when referring to a preferred nucleotide sequence motif or nucleotide sequence, which consists of only nucleotides, the oligomers which are defined by that sequence may comprise a corresponding nucleotide analogue in place of one or more of the nucleotides present in said sequence, such as LNA units or other nucleotide analogues, which raise the duplex stability/$T_m$ of the oligomer/target duplex (i.e. affinity enhancing nucleotide analogues).

Examples of such modification of the nucleotide include modifying the sugar moiety to provide a 2'-substituent group or to produce a bridged (locked nucleic acid) structure which enhances binding affinity and may also provide increased nuclease resistance.

A preferred nucleotide analogue is LNA, such as oxy-LNA (such as beta-D-oxy-LNA, and alpha-L-oxy-LNA), and/or amino-LNA (such as beta-D-amino-LNA and alpha-L-amino-LNA) and/or thio-LNA (such as beta-D-thio-LNA and alpha-L-thio-LNA) and/or ENA (such as beta-D-ENA and alpha-L-ENA). Most preferred is beta-D-oxy-LNA.

In some embodiments the nucleotide analogues present within the oligomer of the method of the invention (such as in regions X' and Y' mentioned herein) are independently selected from, for example: 2'-O-alkyl-RNA units, 2'-amino-DNA units, 2'-fluoro-DNA units, LNA units, arabino nucleic acid (ANA) units, 2'-fluoro-ANA units, HNA units, INA (intercalating nucleic acid—Christensen, 2002. Nucl. Acids. Res. 2002 30: 4918-4925, hereby incorporated by reference) units and 2'MOE units. In some embodiments there is only one of the above types of nucleotide analogues present in the oligomer of the method of the invention, or contiguous nucleotide sequence thereof.

In some embodiments the nucleotide analogues are 2'-O-methoxyethyl-RNA (2'MOE), 2'-fluoro-DNA monomers or LNA nucleotide analogues, and as such the oligonucleotide of the invention may comprise nucleotide analogues which are independently selected from these three types of analogue, or may comprise only one type of analogue selected from the three types. In some embodiments at least one of said nucleotide analogues is 2'-MOE-RNA, such as 2, 3, 4, 5, 6, 7, 8, 9 or 10 2'-MOE-RNA nucleotide units. In some embodiments at least one of said nucleotide analogues is 2'-fluoro DNA, such as 2, 3, 4, 5, 6, 7, 8, 9 or 10 2'-fluoro-DNA nucleotide units.

In some embodiments, the oligomer according to the method invention comprises at least one Locked Nucleic Acid (LNA) unit, such as 1, 2, 3, 4, 5, 6, 7, or 8 LNA units, such as from 3-7 or 4 to 8 LNA units, or 3, 4, 5, 6 or 7 LNA units. In some embodiments, all the nucleotide analogues are LNA. In some embodiments, the oligomer may comprise both beta-D-oxy-LNA, and one or more of the following LNA units: thio-LNA, amino-LNA, oxy-LNA, and/or ENA in either the beta-D or alpha-L configurations or combinations thereof. In some embodiments all LNA cytosine units are 5'methyl-Cytosine. In some embodiments of the invention, the oligomer may comprise both LNA and DNA units. Preferably the combined total of LNA and DNA units is 10-25, such as 10-24, preferably 10-20, such as 10-18, even more preferably 12-16. In some embodiments of the invention, the nucleotide sequence of the oligomer, such as the contiguous nucleotide sequence consists of at least one LNA and the remaining nucleotide units are DNA units. In some embodiments the oligomer comprises only LNA nucleotide analogues and naturally occurring nucleotides (such as RNA or DNA, most preferably DNA nucleotides), optionally with modified internucleotide linkages such as phosphorothioate.

The term "nucleobase" refers to the base moiety of a nucleotide and covers both naturally occurring a well as non-naturally occurring variants. Thus, "nucleobase" covers not only the known purine and pyrimidine heterocycles but also heterocyclic analogues and tautomers thereof.

Examples of nucleobases include, but are not limited to adenine, guanine, cytosine, thymidine, uracil, xanthine, hypoxanthine, 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

In some embodiments, at least one of the nucleobases present in the oligomer is a modified nucleobase selected from the group consisting of 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

LNA

The term "LNA" refers to a bicyclic nucleoside analogue, known as "Locked Nucleic Acid". It may refer to an LNA monomer, or, when used in the context of an "LNA oligonucleotide", LNA refers to an oligonucleotide containing one or more such bicyclic nucleotide analogues. LNA nucleotides are characterised by the presence of a linker group (such as a bridge) between C2' and C4' of the ribose sugar ring—for example as shown as the biradical $R^{4*}$—$R^{2*}$ as described below.

The LNA used in the oligonucleotide compounds of the invention preferably has the structure of the general formula I Formula 1

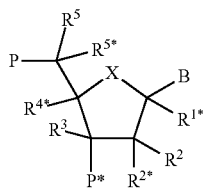

wherein for all chiral centers, asymmetric groups may be found in either R or S orientation;

wherein X is selected from —O—, —S—, —N($R^{N*}$)—, —C($R^6R^{6*}$)—, such as, in some embodiments —O—;

B is selected from hydrogen, optionally substituted $C_{1-4}$-alkoxy, optionally substituted $C_{1-4}$-alkyl, optionally substituted $C_{1-4}$-acyloxy, nucleobases including naturally occurring and nucleobase analogues, DNA intercalators, photochemically active groups, thermochemically active groups, chelating groups, reporter groups, and ligands; preferably, B is a nucleobase or nucleobase analogue;

P designates an internucleotide linkage to an adjacent monomer, or a 5'-terminal group, such internucleotide linkage or 5'-terminal group optionally including the substituent $R^5$ or equally applicable the substituent $R^{5*}$;

P* designates an internucleotide linkage to an adjacent monomer, or a 3'-terminal group;

$R^{4*}$ and $R^{2*}$ together designate a bivalent linker group consisting of 1-4 groups/atoms selected from —C($R^aR^b$)—, —C($R^a$)=C($R^b$)—, —C($R^a$)=N—, —O—, —Si($R^a$)$_2$—, —S—, —SO$_2$—, —N($R^a$)—, and >C=Z, wherein Z is selected from —O—, —S—, and —N($R^a$)—, and $R^a$ and $R^b$ each is independently selected from hydrogen, optionally substituted $C_{1-12}$-alkyl, optionally substituted $C_{2-12}$-alkenyl, optionally substituted $C_{2-12}$-alkynyl, hydroxy, optionally substituted $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (=CH$_2$), wherein for all chiral centers, asymmetric groups may be found in either R or S orientation, and;

each of the substituents $R^{1*}$, $R^2$, $R^3$, $R^5$, $R^{5*}$, $R^6$ and $R^{6*}$, which are present is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene; wherein $R^N$ is selected from hydrogen and $C_{1-4}$-alkyl, and where two adjacent (non-geminal) substituents may designate an additional bond resulting in a double bond; and $R^{N*}$, when present and not involved in a biradical, is selected from hydrogen and $C_{1-4}$-alkyl; and basic salts and acid addition salts thereof. For all chiral centers, asymmetric groups may be found in either R or S orientation.

In some embodiments, $R^{4*}$ and $R^{2*}$ together designate a biradical consisting of a groups selected from the group consisting of C($R^aR^b$)—C($R^aR^b$)—, C($R^aR^b$)—O—, C($R^aR^b$)—NR$^a$—, C($R^aR^b$)—S—, and C($R^aR^b$)—C($R^aR^b$)—O—, wherein each $R^a$ and $R^b$ may optionally be independently selected. In some embodiments, $R^a$ and $R^b$ may be, optionally independently selected from the group consisting of hydrogen and $C_{1-6}$ alkyl, such as methyl, such as hydrogen.

In some embodiments, $R^{4*}$ and $R^{2*}$ together designate the biradical —O—CH(CH$_2$OCH$_3$)— (2'O-methoxyethyl bicyclic nucleic acid—Seth at al., 2010, J. Org. Chem)—in either the R- or S-configuration.

In some embodiments, $R^{4*}$ and $R^{2*}$ together designate the biradical —O—CH(CH$_2$CH$_3$)— (2'O-ethyl bicyclic nucleic acid—Seth at al., 2010, J. Org. Chem).—in either the R- or S-configuration.

In some embodiments, $R^{4*}$ and $R^{2*}$ together designate the biradical —O—CH(CH$_3$)—.—in either the R- or S-configuration. In some embodiments, $R^{4*}$ and $R^{2*}$ together designate the biradical —O—CH$_2$—O—CH$_2$— —(Seth at al., 2010, J. Org. Chem).

In some embodiments, $R^{4*}$ and $R^{2*}$ together designate the biradical —O—NR—CH$_3$— (Seth at al., 2010, J. Org. Chem).

In some embodiments, the LNA units have a structure selected from the following group:

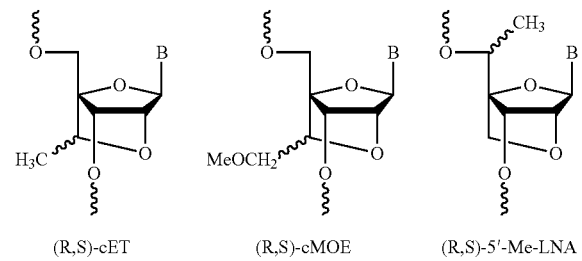

(R,S)-cET     (R,S)-cMOE     (R,S)-5'-Me-LNA

In some embodiments, $R^{1*}$, $R^2$, $R^3$, $R^5$, $R^{5*}$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$alkoxyl, substituted $C_{1-6}$alkoxyl, acyl, substituted acyl, $C_{1-6}$ aminoalkyl or substituted $C_{1-6}$ aminoalkyl. For all chiral centers, asymmetric groups may be found in either R or S orientation.

In some embodiments, $R^{1*}$, $R^2$, $R^3$, $R^5$, $R^{5*}$ are hydrogen.

In some embodiments, $R^{1*}$, $R^2$, $R^3$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$alkoxyl, substituted $C_{1-6}$alkoxyl, acyl, substituted acyl, $C_{1-6}$ aminoalkyl or substituted $C_{1-6}$ aminoalkyl. For all chiral centers, asymmetric groups may be found in either R or S orientation.

In some embodiments, $R^{1*}$, $R^2$, $R^3$ are hydrogen.

In some embodiments, $R^5$ and $R^{5*}$ are each independently selected from the group consisting of H, —CH$_3$, —CH$_2$—CH$_3$, —CH$_2$—O—CH$_3$, and —CH=CH$_2$. Suitably in some embodiments, either $R^5$ or $R^{5*}$ are hydrogen, where as the other group ($R^5$ or $R^{5*}$respectively) is selected from the group consisting of $C_{1-5}$ alkyl, $C_{2-6}$ alkenyl, $C_{2-6}$ alkynyl, substituted $C_{1-6}$ alkyl, substituted $C_{2-6}$ alkenyl, substituted $C_{2-6}$ alkynyl or substituted acyl (—C(=O)—); wherein each substituted group is mono or poly substituted with substituent groups independently selected from halogen, $C_{1-6}$ alkyl, substituted $C_{1-6}$ alkyl, $C_{2-6}$ alkenyl, substituted $C_{2-6}$ alkenyl, $C_{2-6}$alkynyl, substituted $C_{2-6}$alkynyl, $OJ_1$, $SJ_1$, $NJ_1J_2$, $N_3$, $COOJ_1$, CN, O—C(=O)$NJ_1J_2$, N(H)C(=NH)$NJ_1$, $J_2$ or N(H)C(=X)N(H)$J_2$ wherein X is O or S; and each $J_1$ and $J_2$ is, independently, H, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{1-6}$ aminoalkyl, substituted $C_{1-6}$ aminoalkyl or a protecting group. In some embodiments either $R^5$ or $R^{5*}$ is substituted $C_{1-6}$ alkyl. In some embodiments either $R^5$ or $R^{5*}$ is substituted methylene wherein preferred substituent groups include one or more groups independently selected from F, $NJ_1J_2$, $N_3$, CN, $OJ_1$, $SJ_1$, O—C(=O)$NJ_1J_2$, N(H)C(=NH)NJ, $J_2$ or N(H)C(O)N(H)$J_2$. In some embodiments each $J_1$ and $J_2$ is, independently H or $C_{1-6}$ alkyl. In some embodiments either $R^5$ or $R^{5*}$ is methyl, ethyl or methoxymethyl. In some embodiments either $R^5$ or $R^{5*}$ is methyl. In a further embodiment either $R^5$ or $R^{5*}$ is ethylenyl. In some embodiments either $R^5$ or $R^{5*}$ is substituted acyl. In some embodiments either $R^5$ or $R^{5*}$ is C(=O)$NJ_1J_2$. For all chiral centers, asymmetric groups may be found in either R or S orientation. Such 5' modified bicyclic nucleotides are disclosed in WO 2007/134181, which is hereby incorporated by reference in its entirety.

In some embodiments B is a nucleobase, including nucleobase analogues and naturally occurring nucleobases, such as a purine or pyrimidine, or a substituted purine or substituted pyrimidine, such as a nucleobase referred to herein, such as a nucleobase selected from the group consisting of adenine, cytosine, thymine, adenine, uracil, and/or a modified or substituted nucleobase, such as 5-thiazolo-uracil, 2-thio-uracil, 5-propynyl-uracil, 2'thio-thymine, 5-methyl cytosine, 5-thiazolo-cytosine, 5-propynyl-cytosine, and 2,6-diaminopurine.

In some embodiments, $R^{4*}$ and $R^{2*}$ together designate a biradical selected from —C($R^aR^b$)—O—, —C($R^aR^b$)—C($R^cR^d$)—O—, —C($R^aR^b$)—C($R^cR^d$)—C($R^eR^f$)—O—, —C($R^aR^b$)—O—C($R^cR^d$)—, —C($R^aR^b$)—O—C($R^cR^d$)—O—, —C($R^aR^b$)—C($R^cR^d$)—, —C($R^aR^b$)—C($R^cR^d$)—C($R^eR^f$)—, —C($R^a$)=C($R^b$)—C($R^cR^d$)—, —C($R^aR^b$)—N($R^c$)—, —C($R^aR^b$)—C($R^cR^d$)—N($R^e$)—, —C($R^aR^b$)—N($R^c$)—O—, and —C($R^aR^b$)—S—, —C($R^aR^b$)—C($R^cR^d$)—S—, wherein $R^a$, $R^b$, $R^c$, $R^d$, $R^e$, and $R^f$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (=$CH_2$). For all chiral centers, asymmetric groups may be found in either R or S orientation.

In a further embodiment $R^{4*}$ and $R^{2*}$ together designate a biradical (bivalent group) selected from —$CH_2$—O—, —$CH_2$—S—, —$CH_2$—NH—, —$CH_2$—N($CH_3$)—, —$CH_2$—$CH_2$—O—, —$CH_2$—CH($CH_3$)—, —$CH_2$—$CH_2$—S—, —$CH_2$—$CH_2$—NH—, —$CH_2$—$CH_2$—$CH_2$—, —$CH_2$—$CH_2$—$CH_2$—O—, —$CH_2$—$CH_2$—CH($CH_3$)—, —CH=CH—$CH_2$—, —$CH_2$—O—$CH_2$—O—, —$CH_2$—NH—O—, —$CH_2$—O—$CH_2$—, —CH($CH_3$)—O—, and —CH($CH_2$—O—$CH_3$)—O—, and/or, —$CH_2$—$CH_2$—, and —CH=CH— For all chiral centers, asymmetric groups may be found in either R or S orientation.

In some embodiments, $R^{4*}$ and $R^{2*}$ together designate the biradical C($R^aR^b$)—N($R^c$)—O—, wherein $R^a$ and $R^b$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl, such as hydrogen, and; wherein $R^c$ is selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl, such as hydrogen.

In some embodiments, $R^{4*}$ and $R^{2*}$ together designate the biradical C($R^aR^b$)—O—C($R^cR^d$)—O—, wherein $R^a$, $R^b$, $R^c$, and $R^d$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl, such as hydrogen.

In some embodiments, $R^{4*}$ and $R^{2*}$ form the biradical —CH(Z)—O—, wherein Z is selected from the group consisting of $C_{1-6}$ alkyl, $C_{2-6}$ alkenyl, $C_{2-6}$ alkynyl, substituted $C_{1-6}$ alkyl, substituted $C_{2-6}$ alkenyl, substituted $C_{2-6}$ alkynyl, acyl, substituted acyl, substituted amide, thiol or substituted thio; and wherein each of the substituted groups, is, independently, mono or poly substituted with optionally protected substituent groups independently selected from halogen, oxo, hydroxyl, $OJ_1$, $NJ_1J_2$, $SJ_1$, $N_3$, OC(=X)$J_1$, OC(=X)$NJ_1J_2$, $NJ^3$C(=X)$NJ_1J_2$ and CN, wherein each $J_1$, $J_2$ and $J_3$ is, independently, H or $C_{1-6}$ alkyl, and X is O, S or $NJ_1$. In some embodiments Z is $C_{1-6}$ alkyl or substituted $C_{1-6}$ alkyl. In some embodiments Z is methyl. In some embodiments Z is substituted $C_{1-6}$ alkyl. In some embodiments said substituent group is $C_{1-6}$ alkoxy. In some embodiments Z is $CH_3OCH_2$—. For all chiral centers, asymmetric groups may be found in either R or S orientation. Such bicyclic nucleotides are disclosed in U.S. Pat. No. 7,399,845 which is hereby incorporated by reference in its entirety. In some embodiments, $R^{1*}$, $R^2$, $R^3$, $R^5$, $R^{5*}$ are hydrogen. In some embodiments, $R^{1*}$, $R^2$, $R^{3*}$ are hydrogen, and one or both of $R^5$, $R^{5*}$ may be other than hydrogen as referred to above and in WO 2007/134181.

In some embodiments, $R^{4*}$ and $R^{2*}$ together designate a biradical which comprise a substituted amino group in the bridge such as consist or comprise of the biradical —$CH_2$—N($R^c$)—, wherein $R^c$ is $C_{1-12}$ alkyloxy. In some embodiments $R^{4*}$ and $R^{2*}$ together designate a biradical —$Cq_3q_4$—NOR—, wherein $q_3$ and $q_4$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$alkoxyl, substituted $C_{1-6}$alkoxyl, acyl, substituted acyl, $C_{1-6}$ aminoalkyl or substituted $C_{1-6}$ aminoalkyl; wherein each substituted group is, independently, mono or poly substituted with substituent groups independently selected from halogen, $OJ_1$, $SJ_1$, $NJ_1J_2$, $COOJ_1$, CN, O—C(=O)$NJ_1J_2$, N(H)C(=NH)N $J_1J_2$ or N(H)C(=X=N(H)$J_2$ wherein X is O or S; and each of $J_1$ and $J_2$ is, independently, H, $C_{1-6}$ alkyl, $C_{2-6}$ alkenyl, $C_{2-6}$ alkynyl, $C_{1-6}$ aminoalkyl or a protecting group. For all chiral centers, asymmetric groups may be found in either R or S orientation. Such bicyclic nucleotides are disclosed in WO2008/150729 which is hereby incorporated by reference in its entirety. In some embodiments, $R^{1*}$, $R^2$, $R^3$, $R^5$, $R^{5*}$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$alkoxyl, substituted $C_{1-6}$alkoxyl, acyl, substituted acyl, $C_{1-6}$ aminoalkyl or substituted $C_{1-6}$ aminoalkyl. In some embodiments, $R^{1*}$, $R^2$, $R^3$, $R^5$, $R^{5*}$ are hydrogen. In some embodiments, $R^{1*}$, $R^2$, $R^3$ are hydrogen and one or both of $R^5$, $R^{5*}$ may be other than hydrogen as referred to above and in WO 2007/134181. In some embodiments $R^{4*}$ and $R^{2*}$ together designate a biradical (bivalent group) $C(R^aR^b)$—O—, wherein $R^a$ and $R^b$ are each independently halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_1$, $SJ_1$, $SOJ_1$, $SO_2J_1$, $NJ_1J_2$, $N_3$, CN, C(=O)$OJ_1$, C(=O)$NJ_1J_2$, C(=O)$J_1$, O—C(=O)$NJ_1J_2$, N(H)C(=NH)$NJ_1J_2$, N(H)C(=O)$NJ_1J_2$ or N(H)C(=S)$NJ_1J_2$; or $R^a$ and $R^b$ together are =C(q3)(q4); $q_3$ and $q_4$ are each, independently, H, halogen, $C_1$-$C_{12}$alkyl or substituted $C_1$-$C_{12}$ alkyl; each substituted group is, independently, mono or poly substituted with substituent groups independently selected from halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ or N(H)C(=S)$NJ_1J_2$ and; each $J_1$ and $J_2$ is, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ aminoalkyl, substituted $C_1$-$C_6$ aminoalkyl or a protecting group. Such compounds are disclosed in WO2009006478A, hereby incorporated in its entirety by reference.

In some embodiments, $R^{4*}$ and $R^{2*}$ form the biradical -Q-, wherein Q is $C(q_1)(q_2)C(q_3)(q_4)$, $C(q_1)$=$C(q_3)$, C[=C($q_1$)($q_2$)]-C($q_3$)($q_4$) or C($q_1$)($q_2$)-C[=C($q_3$)($q_4$)]; $q_1$, $q_2$, $q_3$, $q_4$ are each independently. H, halogen, $C_{1-12}$ alkyl, substituted $C_{1-12}$ alkyl, $C_{2-12}$ alkenyl, substituted $C_{2-12}$alkoxy, $OJ_1$, $SJ_1$, $SOJ_1$, $SO_2J_1$, $NJ_1J_2$, $N_3$, CN, C(=O)$OJ_1$, C(=O)—$NJ_1J_2$, C(=O) $J_1$, —C(=O)$NJ_1J_2$, N(H)C(=NH)$NJ_1J_2$, N(H)C(=O)$NJ_1J_2$ or N(H)C(=S)$NJ_1J_2$; each $J_1$ and $J_2$ is, independently, H, $C_{1-6}$ alkyl, $C_{2-6}$ alkenyl, $C_{2-6}$ alkynyl, $C_{1-6}$ aminoalkyl or a protecting group; and, optionally wherein when Q is $C(q_1)(q_2)(q_3)(q_4)$ and one of $q_3$ or $q_4$ is $CH_3$ then at least one of the other of $q_3$ or $q_4$ or one of $q_1$ and $q_2$ is other than H. In some embodiments, $R^{1*}$, $R^2$, $R^3$, $R^5$, $R^{5*}$ are hydrogen. For all chiral centers, asymmetric groups may be found in either R or S orientation. Such bicyclic nucleotides are disclosed in WO2008/154401 which is hereby incorporated by reference in its entirety. In some embodiments, $R^{1*}$, $R^2$, $R^3$, $R^5$, $R^{5*}$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$alkoxyl, substituted $C_{1-6}$alkoxyl, acyl, substituted acyl, $C_{1-6}$ aminoalkyl or substituted $C_{1-6}$ aminoalkyl. In some embodiments, $R^{1*}$, $R^2$, $R^3$, $R^5$, $R^{5*}$ are hydrogen. In some embodiments, $R^{1*}$, $R^2$, $R^3$ are hydrogen and one or both of $R^5$, $R^{5*}$ may be other than hydrogen as referred to above and in WO 2007/134181 or WO2009/067647 (alpha-L-bicyclic nucleic acids analogs).

Further bicyclic nucleoside analogues and their use in antisense oligonucleotides are disclosed in WO2011 115818, WO2011/085102, WO2011/017521, WO09100320, WO10036698, WO09124295 & WO09006478. Such nucleoside analogues may in some aspects be useful in the compounds of present invention.

In some embodiments the LNA used in the oligonucleotide compounds of the invention preferably has the structure of the general formula II:

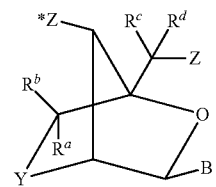

Formula II wherein Y is selected from the group consisting of —O—, —$CH_2$O—, —S—, —NH—, N($R^e$) and/or —$CH_2$—; Z and Z* are independently selected among an internucleotide linkage, $R^H$, a terminal group or a protecting group; B constitutes a natural or non-natural nucleotide base moiety (nucleobase), and $R^H$ is selected from hydrogen and $C_{1-4}$-alkyl; $R^a$, $R^b$, $R^c$, $R^d$ and $R^e$ are, optionally independently, selected from the group consisting of hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (=$CH_2$); and $R^H$ is selected from hydrogen and $C_{1-4}$-alkyl. In some embodiments $R^a$, $R^b$, $R^c$, $R^d$ and $R^e$ are, optionally independently, selected from the group consisting of hydrogen and $C_{1-6}$ alkyl, such as methyl. For all chiral centers, asymmetric groups may be found in either R or S orientation, for example, two exemplary stereochemical isomers include the beta-D and alpha-L isoforms, which may be illustrated as follows:

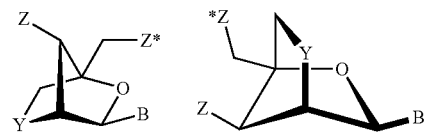

Specific exemplary LNA units are shown below:

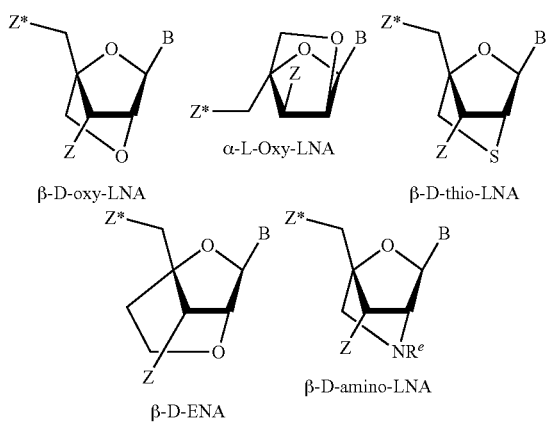

The term "thio-LNA" comprises a locked nucleotide in which Y in the general formula above is selected from S or —CH₂—S—. Thio-LNA can be in both beta-D and alpha-L-configuration.

The term "amino-LNA" comprises a locked nucleotide in which Y in the general formula above is selected from —N(H)—, N(R)—, CH₂—N(H)—, and —CH₂—N(R)— where R is selected from hydrogen and $C_{1-4}$-alkyl. Amino-LNA can be in both beta-D and alpha-L-configuration.

The term "oxy-LNA" comprises a locked nucleotide in which Y in the general formula above represents —O—. Oxy-LNA can be in both beta-D and alpha-L-configuration.

The term "ENA" comprises a locked nucleotide in which Y in the general formula above is —CH₂—O— (where the oxygen atom of —CH₂—O— is attached to the 2'-position relative to the base B). $R^e$ is hydrogen or methyl.

In some exemplary embodiments LNA is selected from beta-D-oxy-LNA, alpha-L-oxy-LNA, beta-D-amino-LNA and beta-D-thio-LNA, in particular beta-D-oxy-LNA.

Conjugates

In the context the term "conjugate" is intended to indicate a heterogenous molecule formed by the covalent attachment ("conjugation") of the oligomer as described herein to one or more non-nucleotide, or non-polynucleotide moieties. Examples of non-nucleotide or non-polynucleotide moieties include macromolecular agents such as proteins, fatty acid chains, sugar residues, glycoproteins, polymers, or combinations thereof. Typically proteins may be antibodies for a target protein. Typical polymers may be polyethylene glycol.

Therefore, in various embodiments, the oligomer of the invention may comprise both a polynucleotide region which typically consists of a contiguous sequence of nucleotides, and a further non-nucleotide region. When referring to the oligomer of the invention consisting of a contiguous nucleotide sequence, the compound may comprise non-nucleotide components, such as a conjugate component.

In various embodiments of the invention the oligomeric compound is linked to ligands/conjugates, which may be used, e.g. to increase the cellular uptake of oligomeric compounds. WO2007/031091 provides suitable ligands and conjugates, which are hereby incorporated by reference.

The invention also provides for a conjugate comprising the compound according to the invention as herein described, and at least one non-nucleotide or non-polynucleotide moiety covalently attached to said compound. Therefore, in various embodiments where the compound of the invention consists of a specified nucleic acid or nucleotide sequence, as herein disclosed, the compound may also comprise at least one non-nucleotide or non-polynucleotide moiety (e.g. not comprising one or more nucleotides or nucleotide analogues) covalently attached to said compound.

Conjugation (to a conjugate moiety) may enhance the activity, cellular distribution or cellular uptake of the oligomer of the invention. Such moieties include, but are not limited to, antibodies, polypeptides, lipid moieties such as a cholestereol moiety, cholic acid, a thioether, e.g. Hexyl-s-tritylthiol, a thiocholestereol, an aliphatic chain, e.g., dodecandiol or undecyl residues, a phospholipids, e.g., di-hexadecyl-rac-glycerol or triethylammonium 1,2-di-o-hexadecyl-rac-glycero-3-h-phosphonate, a polyamine or a polyethylene glycol chain, an adamantane acetic acid, a palmityl moiety, an octadecylamine or hexylamino-carbonyl-oxycholestereol moiety.

The oligomers of the invention may also be conjugated to active drug substances, for example, aspirin, ibuprofen, a sulfa drug, an antidiabetic, an antibacterial or an antibiotic.

In certain embodiments the conjugated moiety is a stereol, such as cholestereol.

In various embodiments, the conjugated moiety comprises or consists of a positively charged polymer, such as a positively charged peptides of, for example from 1-50, such as 2-20 such as 3-10 amino acid residues in length, and/or polyalkylene oxide such as polyethylglycol (PEG) or polypropylene glycol—see WO 2008/034123, hereby incorporated by reference. Suitably the positively charged polymer, such as a polyalkylene oxide may be attached to the oligomer of the invention via a linker such as the releasable inker described in WO 2008/034123.

By way of example, the following GalNAc conjugate moieties may be used in the conjugates of the invention:

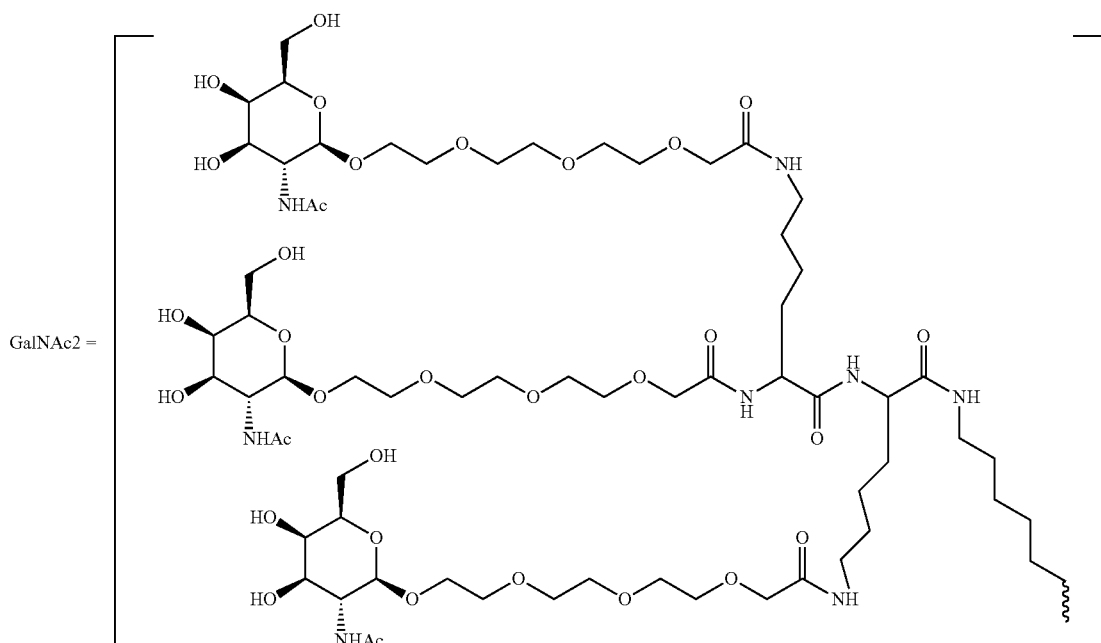

GalNAc2 =

The invention further provides a conjugate comprising the oligomer according to the invention, which comprises at least one non-nucleotide or non-polynucleotide moiety ("conjugated moiety") covalently attached to the oligomer of the invention. In some embodiments the conjugate of the invention is covalently attached to the oligomer via a biocleavable linker, which, for example may be a region of phosphodiester linked nucleotides, such as 1-5 PO linked DNA nucleosides (WO2014/076195, hereby incorporated by reference). Preferred conjugate groups include carbohydrate conjugates, such as GalNAc conjugates, such as trivalent GalNAc conjugates (e.g. see WO2014/118267, hereby incorporated by reference) or lipophilic conjugates, such as a stereol, e.g. cholestereol (WO2014/076195, hereby incorporated by reference)

Activated Oligomers

The term "activated oligomer," as used herein, refers to an oligomer of the invention that is covalently linked (i.e., functionalized) to at least one functional moiety that permits covalent linkage of the oligomer to one or more conjugated moieties, i.e., moieties that are not themselves nucleic acids or monomers, to form the conjugates herein described. Typically, a functional moiety will comprise a chemical group that is capable of covalently bonding to the oligomer via, e.g., a 3'-hydroxyl group or the exocyclic $NH_2$ group of the adenine base, a spacer that is preferably hydrophilic and a terminal group that is capable of binding to a conjugated moiety (e.g., an amino, sulfhydryl or hydroxyl group). In some embodiments, this terminal group is not protected, e.g., is an $NH_2$ group. In other embodiments, the terminal group is protected, for example, by any suitable protecting group such as those described in "Protective Groups in Organic Synthesis" by Theodora W Greene and Peter G M Wuts, 3rd edition (John Wiley & Sons, 1999). Examples of suitable hydroxyl protecting groups include esters such as acetate ester, aralkyl groups such as benzyl, diphenylmethyl, or triphenylmethyl, and tetrahydropyranyl. Examples of suitable amino protecting groups include benzyl, alpha-methylbenzyl, diphenylmethyl, triphenylmethyl, benzyloxycarbonyl, tert-butoxycarbonyl, and acyl groups such as trichloroacetyl or trifluoroacetyl. In some embodiments, the functional moiety is self-cleaving. In other embodiments, the functional moiety is biodegradable. See e.g., U.S. Pat. No. 7,087,229, which is incorporated by reference herein in its entirety.

In some embodiments, oligomers of the invention are functionalized at the 5' end in order to allow covalent attachment of the conjugated moiety to the 5' end of the oligomer. In other embodiments, oligomers of the invention can be functionalized at the 3' end. In still other embodiments, oligomers of the invention can be functionalized along the backbone or on the heterocyclic base moiety. In yet other embodiments, oligomers of the invention can be functionalized at more than one position independently selected from the 5' end, the 3' end, the backbone and the base.

In some embodiments, activated oligomers of the invention are synthesized by incorporating during the synthesis one or more monomers that is covalently attached to a functional moiety. In other embodiments, activated oligomers of the invention are synthesized with monomers that have not been functionalized, and the oligomer is functionalized upon completion of synthesis. In some embodiments, the oligomers are functionalized with a hindered ester containing an aminoalkyl linker, wherein the alkyl portion has the formula $(CH_2)_w$, wherein w is an integer ranging from 1 to 10, preferably about 6, wherein the alkyl portion of the alkylamino group can be straight chain or branched chain, and wherein the functional group is attached to the oligomer via an ester group (—O—C(O)—$(CH_2)_2NH$).

In other embodiments, the oligomers are functionalized with a hindered ester containing a $(CH_2)_2$-sulfhydryl (SH) linker, wherein w is an integer ranging from 1 to 10, preferably about 6, wherein the alkyl portion of the alkylamino group can be straight chain or branched chain, and wherein the functional group attached to the oligomer via an ester group (—O—C(O)—$(CH_2)_2SH$)

In some embodiments, sulfhydryl-activated oligonucleotides are conjugated with polymer moieties such as polyethylene glycol or peptides (via formation of a disulfide bond).

Activated oligomers containing hindered esters as described above can be synthesized by any method known in the art, and in particular by methods disclosed in PCT Publication No. WO 2008/034122 and the examples therein, which is incorporated herein by reference in its entirety.

In still other embodiments, the oligomers of the invention are functionalized by introducing sulfhydryl, amino or hydroxyl groups into the oligomer by means of a functionalizing reagent substantially as described in U.S. Pat. Nos. 4,962,029 and 4,914,210, i.e., a substantially linear reagent having a phosphoramidite at one end linked through a hydrophilic spacer chain to the opposing end which comprises a protected or unprotected sulfhydryl, amino or hydroxyl group. Such reagents primarily react with hydroxyl groups of the oligomer. In some embodiments, such activated oligomers have a functionalizing reagent coupled to a 5'-hydroxyl group of the oligomer. In other embodiments, the activated oligomers have a functionalizing reagent coupled to a 3'-hydroxyl group. In still other embodiments, the activated oligomers of the invention have a functionalizing reagent coupled to a hydroxyl group on the backbone of the oligomer. In yet further embodiments, the oligomer of the invention is functionalized with more than one of the functionalizing reagents as described in U.S. Pat. Nos. 4,962,029 and 4,914,210, incorporated herein by reference in their entirety. Methods of synthesizing such functionalizing reagents and incorporating them into monomers or oligomers are disclosed in U.S. Pat. Nos. 4,962,029 and 4,914,210.

In some embodiments, the 5'-terminus of a solid-phase bound oligomer is functionalized with a dienyl phosphoramidite derivative, followed by conjugation of the deprotected oligomer with, e.g., an amino acid or peptide via a Diels-Alder cycloaddition reaction.

In various embodiments, the incorporation of monomers containing 2'-sugar modifications, such as a 2'-carbamate substituted sugar or a 2'-(O-pentyl-N-phthalimido)-deoxyribose sugar into the oligomer facilitates covalent attachment of conjugated moieties to the sugars of the oligomer. In other embodiments, an oligomer with an amino-containing linker at the 2'-position of one or more monomers is prepared using a reagent such as, for example, 5'-dimethoxytrityl-2'-O-(e-phthalimidylaminopentyl)-2'-deoxyadenosine-3'-N,N-diisopropyl-cyanoethoxy phosphoramidite. See, e.g., Manoharan, et al., Tetrahedron Letters, 1991, 34, 7171.

In still further embodiments, the oligomers of the invention may have amine-containing functional moieties on the nucleobase, including on the N6 purine amino groups, on the exocyclic N2 of guanine, or on the N4 or 5 positions of cytosine. In various embodiments, such functionalization may be achieved by using a commercial reagent that is already functionalized in the oligomer synthesis.

Some functional moieties are commercially available, for example, heterobifunctional and homobifunctional linking moieties are available from the Pierce Co. (Rockford, Ill.). Other commercially available linking groups are 5'-Amino-Modifier C6 and 3'-Amino-Modifier reagents, both available from Glen Research Corporation (Sterling, Va.). 5'-Amino-Modifier C6 is also available from ABI (Applied Biosystems Inc., Foster City, Calif.) as Aminolink-2, and 3'-Amino-Modifier is also available from Clontech Laboratories Inc. (Palo Alto, Calif.). In some embodiments in some embodiments Compositions The oligomer of the invention may be used in pharmaceutical formulations and compositions. Suitably, such compositions comprise a pharmaceutically acceptable diluent, carrier, salt or adjuvant. PCT/DK2006/000512 provides suitable and preferred pharmaceutically acceptable diluent, carrier and adjuvants—which are hereby incorporated by reference. Suitable dosages, formulations, administration routes, compositions, dosage forms, combinations with other therapeutic agents, pro-drug formulations are also provided in PCT/DK2006/000512—which are also hereby incorporated by reference.

Applications

The oligomers of the invention may be utilized as research reagents for, for example, diagnostics, therapeutics and prophylaxis.

In research, such oligomers may be used to specifically inhibit the synthesis of a target protein (typically by degrading or inhibiting the mRNA and thereby prevent protein formation) in cells and experimental animals thereby facilitating functional analysis of the target or an appraisal of its usefulness as a target for therapeutic intervention.

In diagnostics the oligomers may be used to detect and quantitate a target expression in cell and tissues by northern blotting, in-situ hybridisation or similar techniques.

For therapeutics, an animal or a human, suspected of having a disease or disorder, which can be treated by modulating the expression of a target is treated by administering oligomeric compounds in accordance with this invention. Further provided are methods of treating a mammal, such as treating a human, suspected of having or being prone to a disease or condition, associated with expression of a target by administering a therapeutically or prophylactically effective amount of one or more of the oligomers or compositions of the invention. The oligomer, a conjugate or a pharmaceutical composition according to the invention is typically administered in an effective amount.

The invention also provides for the use of the compound or conjugate of the invention as described for the manufacture of a medicament for the treatment of a disorder as referred to herein, or for a method of the treatment of as a disorder as referred to herein.

The invention also provides for a method for treating a disorder as referred to herein said method comprising administering a compound according to the invention as herein described, and/or a conjugate according to the invention, and/or a pharmaceutical composition according to the invention to a patient in need thereof.

Medical Indications

The oligomers and other compositions according to the invention can be used for the treatment of conditions associated with over expression or expression of mutated version of the target.

The invention further provides use of a compound of the invention in the manufacture of a medicament for the treatment of a disease, disorder or condition as referred to herein.

Generally stated, one aspect of the invention is directed to a method of treating a mammal suffering from or susceptible to conditions associated with abnormal levels of the target, comprising administering to the mammal and therapeutically effective amount of an oligomer targeted to the target that comprises one or more LNA units. The oligomer, a conjugate or a pharmaceutical composition according to the invention is typically administered in an effective amount.

Examples

Sequences

The compounds used herein have the following nucleobase sequences:

| | |
|---|---|
| actgctttccactctg | SEQ ID NO 1 |
| tcatggctgcagct | SEQ ID NO 2 |
| gcattggtattca | SEQ ID NO 3 |
| cacattccttgctctg | SEQ ID NO 4 |
| gcaagcatcctgt | SEQ ID NO 5 |

Example 1

Synthesis of DNA 3'-O-oxazaphospholidine monomers was performed as previously described (Oka et al., J. Am. Chem. Soc. 2008 130: 16031-16037, and Wan et al., NAR 2014, November, online publication).

Synthesis of LNA 3'-O-oxazaphospholidine monomers

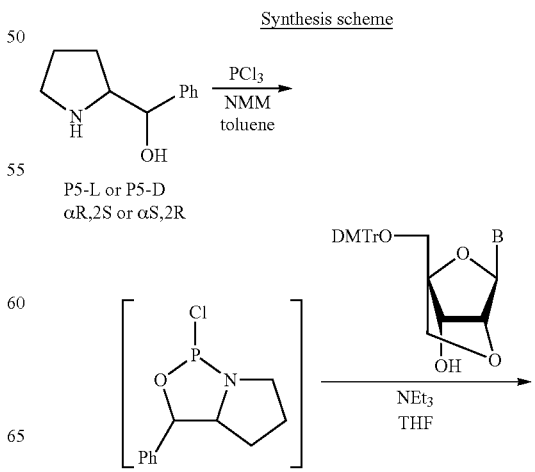

Synthesis scheme

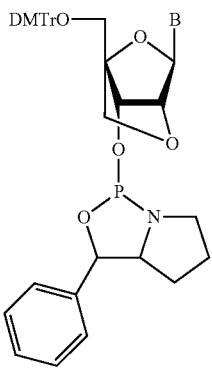

α-Phenyl-2-pyrrolidinemethanol (P5-L and P5-D) was synthesized as described in the literature (Oka et al., *JACS*, 2008, 16031-16037.)

3-OAP-LNA T

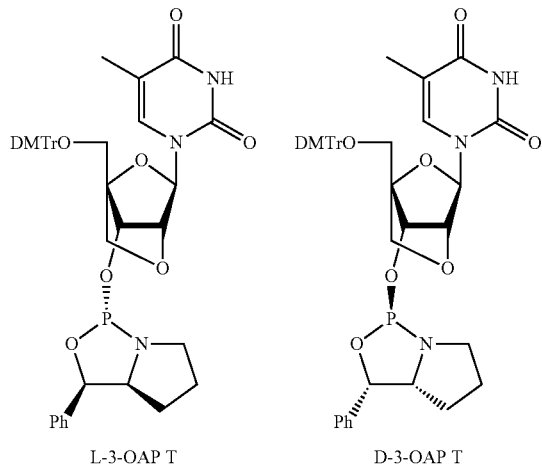

L-3-OAP T  D-3-OAP T

Synthesis of L-3-OAP-LNA T

PCl$_3$ (735 µL, 6.30 mmol) was dissolved in toluene (7 mL), cooled to 0° C. (ice bath) and a solution of P5-L (1.12 g, 6.30 mmol) and NMM (1.38 mL, 12.6 mmol) in toluene (7 mL) was added dropwise. The reaction mixture was stirred at room temperature for 1 h, and then cooled to −72° C. Precipitates were filtered under argon, washed with toluene (4 mL) and filtrate was concentrated at 40° C. and reduced pressure (Schlenk technique). The residue was dissolved in THF (8 mL) and used in the next step.

To a solution of 5'-ODMT-LNA-T (2.40 g, 4.20 mmol) in THF (16 mL), NEt$_3$ (4.10 mL, 29.4 mmol) was added. The reaction mixture was cooled to −74° C. and the solution of 2-chloro-1,3,2-oxazaphospholidine in THF was added dropwise. The reaction mixture was stirred for 4 h at room temperature. EtOAc was added and the reaction mixture was extracted with sat. NaHCO$_3$ (2 times), brine, dried over Na$_2$SO$_4$ and evaporated. The residue was purified by column chromatography (eluent hexanes/EtOAc 30/70+NEt$_3$ 6%). Product was isolated as white foam 1.00 g (yield 30%). $^1$H-NMR spectrum (400 MHz): (DMSO-d$_6$) δ: 11.53 (1H, s), 7.64 (1H, m), 7.46-7.41 (2H, m), 7.40-7.19 (12H, m), 6.92-6.83 (4H, m), 5.51 (1H, d, J=6.3 Hz), 5.49 (1H, s), 4.78 (1H, d, J=7.4 Hz), 4.37 (1H, s), 3.91 (1H, m), 3.76-3.67 (2H, m), 3.72 (3H, s), 3.71 (3H, s), 3.50 (1H, m), 3.41 (2H, s), 2.90 (1H, m), 1.60-1.46 (2H, m), 1.51 (3H, s), 1.15 (1H, m), 0.82 (1H, m). $^{31}$P-NMR spectrum (160 MHz): (DMSO-d$_6$) δ: 151.3. LCMS ESI (m/z): 776.2 [M−H]$^-$.

Synthesis of D-3-OAP-LNA T

PCl$_3$ (1.05 mL, 9.0 mmol) was dissolved in toluene (12 mL), cooled to 0° C. (ice bath) and a solution of P5-D (1.13 g, 12 mmol) and NMM (2.06 mL, 24 mmol) in toluene (12 mL) was added dropwise. The reaction mixture was stirred at room temperature for 1 h, and then cooled to −72° C. Precipitates were filtered under argon, washed with toluene and filtrate was concentrated at 40° C. and reduced pressure (Schlenk technique). The residue was dissolved in THF (18 mL) and used in the next step.

To a solution of 5'-ODMT-LNA-T (3.44 g, 6.0 mmol) in THF (30 mL), NEt$_3$ (5.82 mL, 42 mmol) was added. The reaction mixture was cooled to −74° C. and the solution of 2-chloro-1,3,2-oxazaphospholidine in THF was added dropwise. The reaction mixture was stirred for 4 h at room temperature. EtOAc was added and the reaction mixture was extracted with sat. NaHCO$_3$ (2 times), brine, dried over Na$_2$SO$_4$ and evaporated. The residue was purified by column chromatography (eluent hexanes/EtOAc 30/70+NEt$_3$ 6%). Product was isolated as a white foam 1.86 g (yield 36%), $^1$H-NMR spectrum (400 MHz): (DMSO-d$_6$) δ: 11.55 (1H, s), 7.60 (1H, m), 7.46-7.41 (2H, m), 7.39-7.22 (12H, m), 6.91-6.84 (4H, m), 5.66 (1H, d, J=6.3 Hz), 5.51 (1H, s), 4.60 (1H, d, J=7.4 Hz), 4.41 (1H, s), 3.80-3.70 (3H, m), 3.72 (3H, s), 3.71 (3H, s), 3.48-3.37 (3H, m), 2.96 (1H, m), 1.61-1.43 (2H m), 1.51 (3H, s) 1.10 (1H, m), 0.80 (1H, m). $^{31}$P-NMR spectrum (160 MHz): (DMSO-d$_6$) δ: 152.5. LCMS ESI (m/z): 776.2 [M−H]$^-$.

3-OAP-LNA MeC

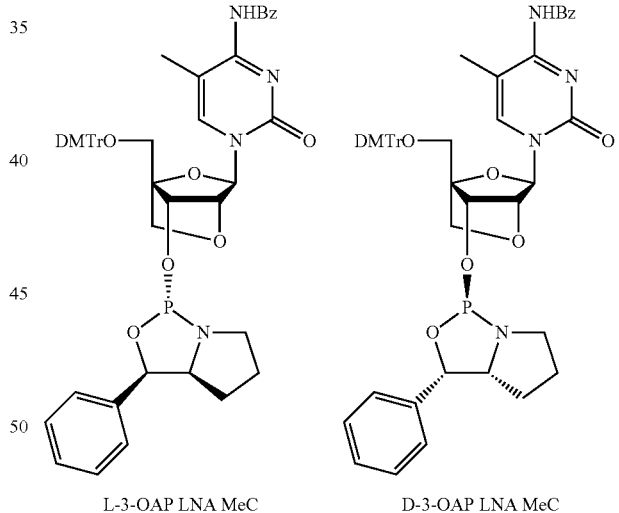

L-3-OAP LNA MeC  D-3-OAP LNA MeC

Synthesis of L-3-OAP-LNA MeC

PCl$_3$ (110 µL, 1.25 mmol) was dissolved in toluene (3 mL), cooled to 0° C. (ice bath) and solution of P5-L (222 mg, 1.25 mmol) and NMM (275 µL, 2.5 mmol) in toluene (3 mL) was added dropwise. The reaction mixture was stirred at room temperature 45 min, and then cooled to −72° C. Precipitates were filtered under argon, washed with toluene and filtrate was concentrated at 40° C. at reduced pressure (Schlenk technique). The residue was dissolved in THF (5 mL) and used in the next step.

To solution of 5'-ODMT-LNA-C (338 mg, 0.50 mmol) in THF (2.5 mL) NEt$_3$ (485 µL, 3.6 mmol) was added. The reaction mixture cooled to −70° C. and the solution of phosphor 2-chloro-1,3,2-oxazaphospholidine was added dropwise. The reaction mixture was stirred for 1.45 h at room temperature. EtOAc (30 mL) was added and the reaction mixture was extracted with sat. NaHCO$_3$ (2×20 mL), brine (20 mL), dried over Na$_2$SO$_4$ and evaporated. The residue was purified by column chromatography (eluent EtOAc in hexanes from 20% to 30%+toluene 10%+NEt$_3$ 7%). Product isolated as white foam 228 mg (yield 47%). $^1$H-NMR spectrum (400 MHz): (CD$_3$CN) δ: 13.3 (1H, br s), 8.41-8.25 (2H, m), 7.88 (1H, m), 7.59 (1H, m), 7.54-7.47 (4H, m), 7.41-7.19 (12H, m), 6.90-6.79 (4H, m), 5.62 (1H, m), 5.58 (1H, s), 4.79 (1H, d, J=7.5 Hz), 4.47 (1H, s), 3.93 (1H, m), 3.86 (1H, m), 3.75 (1H, m), 3.76 (3H, s), 3.75 (3H, s), 3.60-3.47 (3H, m), 2.99 (1H, m), 1.83 (3H, d, J=1.2 Hz), 1.65-1.51 (2H, m), 1.17 (1H, m), 0.89 (1H, m). $^{31}$P-NMR spectrum (160 MHz): (CD$_3$CN) δ: 153.4. LCMS ESI (m/z): 881.2 [M+H]$^+$.

Synthesis of D-3-OAP-LNA MeC

PCl$_3$ (1.10 mL, 12.3 mmol) was dissolved in toluene (10 mL), cooled to 0° C. (ice bath) and solution of P5-D (2.17 g, 12.3 mmol) and NMM (2.70 mL, 2.5 mmol) in toluene (10 mL) was added dropwise. The reaction mixture was stirred at room temperature 45 min, and then cooled to −72° C. Precipitates were filtered under argon, washed with toluene and filtrate was concentrated at 40° C. at reduced pressure (Schlenk technique). The residue was dissolved in THF (10 mL) and used in the next step.

To solution of 5'-ODMT-LNA-C (3.38 g, 5 mmol) in THF (20 mL) NEt$_3$ (4.85 mL, 35 mmol) was added. The reaction mixture cooled to −70° C. and the solution of phosphor 2-chloro-1,3,2-oxazaphospholidine was added dropwise. The reaction mixture was stirred for 1.45 h at room temperature. EtOAc was added and the reaction mixture was extracted with sat. NaHCO$_3$ (2×times), brine, dried over Na$_2$SO$_4$, and evaporated. The residue was purified by column chromatography (eluent EtOAc in hexanes from 20% to 30%+toluene 10%+NEt$_3$ 7%). Product was isolated as white foam 1.09 g (yield 23%). $^1$H-NMR spectrum (400 MHz): (CD$_3$CN) δ: 12.8 (1H, br s), 8.34-8.24 (2H, m), 7.85 (1H, d, J=1.2 Hz), 7.57 (1H, m), 7.53-7.45 (4H, m), 7.41-7.22 (12H, m), 6.89-6.84 (4H, m), 5.72 (1H, d, J=6.5 Hz), 5.59 (1H, s), 4.62 (1H, d, J=8.0 Hz), 4.52 (1H, s), 3.82 (2H, dd, J=24.4 8.2 Hz), 3.77 (1H, m), 3.76 (3H, s), 3.75 (3H, s), 3.51 (2H, s), 3.46 (1H, m), 3.05 (1H, m), 1.81 (3H, s), 1.65-1.47 (2H, m), 1.12 (1H, m), 0.85 (1H, m). $^{31}$P-NMR spectrum (160 MHz): (CD$_3$CN) δ: 153.5. LCMS ESI (m/z): 881.2 [M+H]$^+$.

3-OAP-LNA A

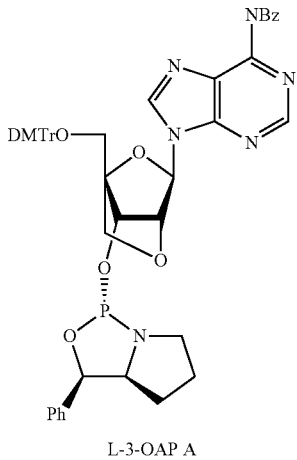

L-3-OAP A

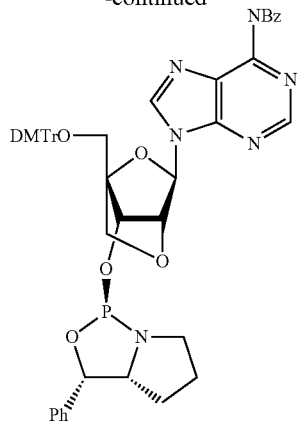

D-3-OAP A

Synthesis of L-3-OAP-LNA A

PCl$_3$ (184 µL, 2.1 mmol) was dissolved in toluene (5 mL), cooled to 0° C. (ice bath) and a solution of P5-L (373 mg, 2.10 mmol) and NMM (463 µL, 4.20 mmol) in toluene (5 mL) was added dropwise. The reaction mixture was stirred at room temperature for 45 min, and then cooled to −72° C. Precipitates was filtered under argon, washed with toluene (4 mL) and filtrate was concentrated at 40° C. at reduce pressure (Schlenk technique). The residue was dissolved in THF (5 mL) and used in the next step.

To a solution of 5'-ODMT-LNA-A (960 mg, 1.40 mmol) in THF (7 mL) NEt$_3$ (1.36 mL, 9.80 mmol) was added. The reaction mixture cooled to −70° C. and the solution of phosphor 2-chloro-1,3,2-oxazaphospholidine was added dropwise. The reaction mixture was stirred for 4 h at room temperature. EtOAc (50 mL) was added and the reaction mixture was extracted with sat. NaHCO$_3$ (2×30 mL), brine (30 mL), dried over Na$_2$SO$_4$ and evaporated. The residue was purified by column chromatography (eluent hexanes/EtOAc 30/70+NEt$_3$ 6-7%).

Product isolated as white foam 455 mg (yield 35%). $^1$H-NMR spectrum (400 MHz): (DMSO-d$_6$) δ: 11.33 (1H, s), 8.76 (1H, s), 8.53 (1H, s), 8.11-8.02 (2H, m), 7.66 (1H, m), 7.60-7.53 (2H, m), 7.44-7.38 (2H, m), 7.35-7.18 (10H, m), 7.05-6.99 (2H, m), 6.89-6.82 (4H, m), 6.21 (1H, s), 5.27 (1H, d, J=6.6 Hz), 5.19 (1H, d, J=7.9 Hz), 4.81 (1H, s), 3.93 (2H, dd, J=29.0 8.2 Hz), 3.77 (1H, m), 3.71 (6H, s), 3.51-3.35 (3H, m), 2.70 (1H, m), 1.56-1.34 (2H, m), 1.10 (1H, m), 0.73 (1H, m). $^{31}$P-NMR spectrum (160 MHz): (DMSO-d$_6$) δ: 149.9. LCMS ESI (m/z): 891.1 [M+H]$^+$.

Synthesis of D-3-OAP-LNA A

PCl$_3$ 0.84 mL, 9.63 mmol) was dissolved in toluene (12 mL), cooled to 0° C. (ice bath) and a solution of P5-D (1.70 g, 9.63 mmol) and NMM (2.12 mL, 19.3 mmol) in toluene (12 mL) was added dropwise. The reaction mixture was stirred at room temperature for 45 min, and then cooled to −72° C. Precipitates was filtered under argon, washed with toluene and filtrate was concentrated at 40° C. at reduce pressure (Schlenk technique). The residue was dissolved in THF (12 mL) and used in the next step.

To a solution of 5'-ODMT-LNA-A (3.77, 5.50 mmol) in THF (20 mL) NEt$_3$ (5.30 mL, 38.5 mmol) was added. The reaction mixture cooled to −70° C. and the solution of phosphor 2-chloro-1,3,2-oxazaphospholidine was added dropwise. The reaction mixture was stirred for 4 h at room temperature. EtOAc was added and the reaction mixture was extracted with sat. NaHCO$_3$, brine, dried over Na$_2$SO$_4$ and evaporated. The residue was purified by column chromatography (eluent hexanes/EtOAc 30/70+NEt$_3$ 6-7%). Product was isolated as a white foam 1.86 g (yield 36%). $^1$H-NMR spectrum (400 MHz): (DMSO-d$_6$) δ: 11.28 (1H, s), 8.78 (1H, s), 8.54 (1H, s), 8.09-8.04 (2H, m), 7.67 (1H, m), 7.60-7.54 (2H, m), 7.42-7.15 (14H, m), 6.89-6.82 (4H, m), 6.21 (1H, s), 5.58 (1H, d, J=6.7 Hz), 5.02 (1H, d, J=8.1 Hz), 4.89 (1H, s), 3.96 (2H, dd, J=35.4 8.2 Hz), 3.71 (3H, s), 3.70 (3H, s), 3.53-3.33 (4H, m), 2.90 (1H, m), 1.54-1.37 (2H, m), 0.98 (1H, m), 0.71 (1H, m). $^{31}$P-NMR spectrum (160 MHz): (DMSO-d$_6$) δ: 150.6, 150.5 (2%), 150.4. LCMS ESI (m/z): 891.1 [M+H]$^+$.

3-OAP-LNA G

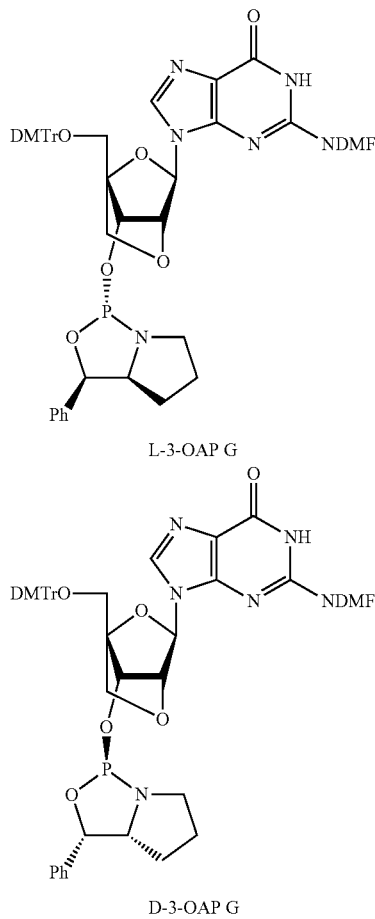

L-3-OAP G

D-3-OAP G

Synthesis of D-3-OAP-LNA G

PCl$_3$ (1.09 mL, 12.4 mmol) was dissolved in toluene (12.5 mL), cooled to 0° C. (ice bath) and a solution of P5-D (2.20 g, 12.4 mmol) and NMM (2.73 mL, 27.8 mmol) in toluene (12.5 mL) was added dropwise. The reaction mixture was stirred at room temperature for 45 min, and then cooled to −72° C. Precipitates was filtered under argon, washed with toluene and filtrate was concentrated at 40° C. at reduce pressure (Schlenk technique). The residue was dissolved in THF (19 mL) and used in the next step.

Before synthesis 5'-ODMT-LNA-G was co evaporated with toluene and then with pyridine (order is essential). To solution of 5'-ODMT-LNA-G (3.26 g, 5.0 mmol) in THF (15 mL) and Pyridine (8 mL), NEt$_3$ (4.85 mL, 35.0 mmol) was added. The reaction mixture cooled to −70° C. and the solution of phosphor 2-chloro-1,3,2-oxazaphospholidine was added dropwise. The reaction mixture was stirred for 2.5 h at room temperature. EtOAc was added and the reaction mixture was extracted with sat. NaHCO$_3$, brine, dried over Na$_2$SO$_4$ and evaporated. The residue was purified by column chromatography (eluent THF in EtOAc from 10% to 20%+NEt$_3$ 6%). Product isolated as white foam 1.49 g (yield 33%). $^1$H-NMR spectrum (400 MHz): (DMSO-d$_6$) δ: 11.42 (1H, s), 8.56 (1H, s), 7.95 (1H, s), 7.49-7.38 (2H, m), 7.36-7.16 (12H, m), 6.90-6.83 (4H, m), 5.96 (1H, s), 5.58 (1H, d, J=6.7 Hz), 4.99 (1H, d, J=8.2 Hz), 4.76 (1H, s), 3.96-3.85 (2H, m), 3.72 (6H, s), 3.62-3.54 (1H, m), 3.45 (2H, s), 3.40-3.33 (1H, m), 3.08 (3H, s), 2.99 (3H, s), 2.93-2.84 (1H, m), 1.53-1.39 (2H, m), 1.06-0.97 (1H, m), 0.79-0.63 (1H, m). $^{31}$P-NMR spectrum (160 MHz): (DMSO-d$_6$) δ: 151.6. LCMS ESI (m/z): 858.2 [M+H]$^+$.

Synthesis of L-3-OAP-LNA G

PCl$_3$ (1.00 mL, 11.4 mmol) was dissolved in toluene (10 mL), cooled to 0° C. (ice bath) and a solution of P5-L (2.02 g, 11.4 mmol) and NMM (2.50 mL, 22.7 mmol) in toluene (10 mL) was added dropwise. The reaction mixture was stirred at room temperature for 45 min, and then cooled to −72° C. Precipitates was filtered under argon, washed with toluene and filtrate was concentrated at 40° C. at reduce pressure (Schlenk technique). The residue was dissolved in THF (7 mL) and used in the next step.

Before synthesis 5'-ODMT-LNA-G was co evaporated with toluene and then with pyridine (order is essential). To a solution of 5'-ODMT-LNA-G (2.86 g, 4.54 mmol) in THF (20 mL) and Pyridine (12 mL), NEt$_3$ (4.40 mL, 31.8 mmol) was added. The reaction mixture cooled to −70° C. and the solution of phosphor 2-chloro-1,3,2-oxazaphospholidine was added dropwise. The reaction mixture was stirred for 2.5 h at room temperature. EtOAc was added and the reaction mixture was extracted with sat. NaHCO$_3$, brine, dried over Na$_2$SO$_4$ and evaporated. The residue was purified by column chromatography (eluent THF in EtOAc from 10% to 20%+NEt$_3$ 6%). Product isolated as white foam 1.44 g (yield 34%). $^1$H-NMR (400 mHz, DMSO-d$_6$): δ: 11.44 (1H, s), 8.42 (1H, s), 7.94 (1H, s), 7.44-7.38 (2H, m), 7.34-7.23 (10H, m), 7.03-6.98 (2H, m), 5.94 (1H, s), 5.17 (1H, d, J=6.5 Hz), 5.07 (1H, d, J=7.8 Hz), 4.68 (1H, s), 3.88 (1H, d, J=8.2 Hz), 3.84 (1H, d, J=8.2 Hz), 3.73 (3H, s), 3.72 (3H, s), 3.68 (1H, m), 3.46-3.36 (3H, m), 3.05 (3H, s), 2.95 (3H, s), 2.77 (1H, m), 1.55-1.38 (2H, m), 1.07 (1H, m), 0.75 (1H, m). $^{31}$P-NMR (160 MHz, DMSO-d$_6$): δ:148.4. LCMS ESI(m/z): 858.5 [M+H]$^+$; 856.5 [M−H]$^−$ Generic Synthesis Description Synthesis of phosphor 2-chloro-1,3,2-oxazaphospholidine: PCl$_3$ (1 eq) was dissolved in toluene, cooled to 0° C. (ice bath) and a solution of P5-L (1 eq) and NMM (2.1 eq) in toluene was added dropwise. The reaction mixture was stirred at room temperature, and then cooled to −72° C. Precipitates was filtered under argon, washed with toluene and filtrate was concentrated at 40° C. at reduce pressure (Schlenk technique). The residue was dissolved in THF and used in the next step.

To a solution of 5'-ODMT-LNA nucleoside (1 eq) in THF (and Pyridine in case of G nucleoside), NEt$_3$ (7 eq) was added. The reaction mixture cooled to −70° C. and the solution of phosphor 2-chloro-1,3,2-oxazaphospholidine (2.5 eq) was added dropwise. The reaction mixture was stirred for at room temperature. EtOAc was added and the reaction mixture was extracted with sat. NaHCO$_3$, brine, dried over Na$_2$SO$_4$ and evaporated. The residue was purified by column chromatography.
Structure Figures of the LNA Monomers
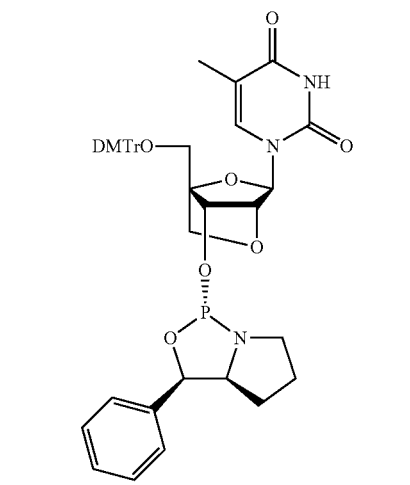
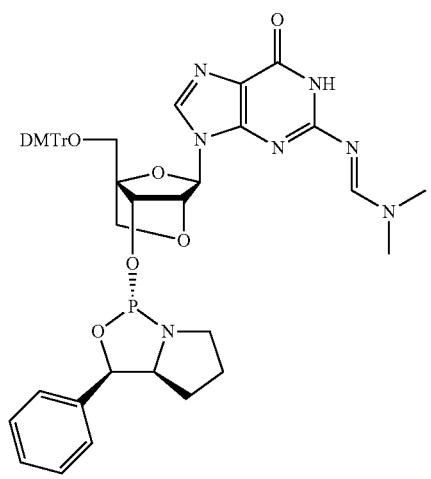
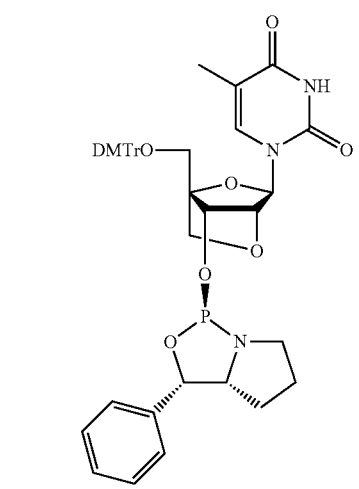
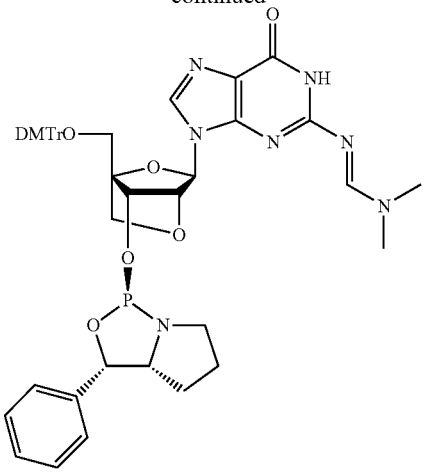
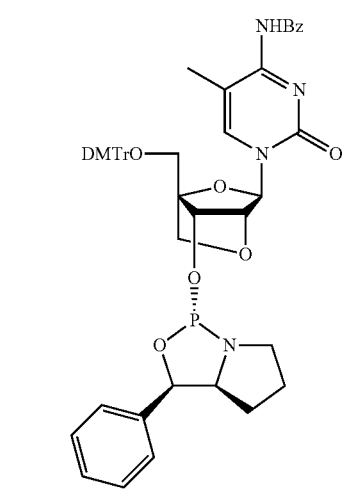
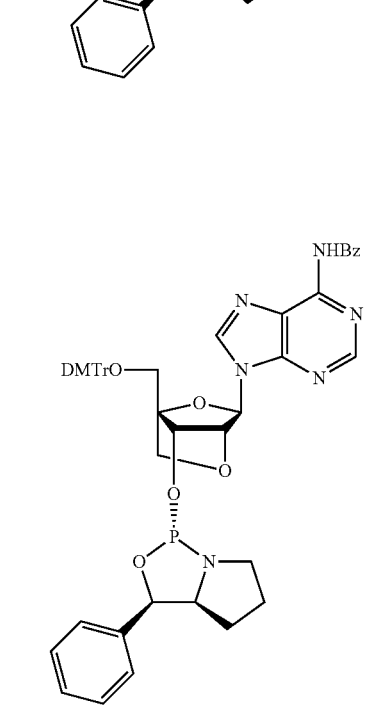

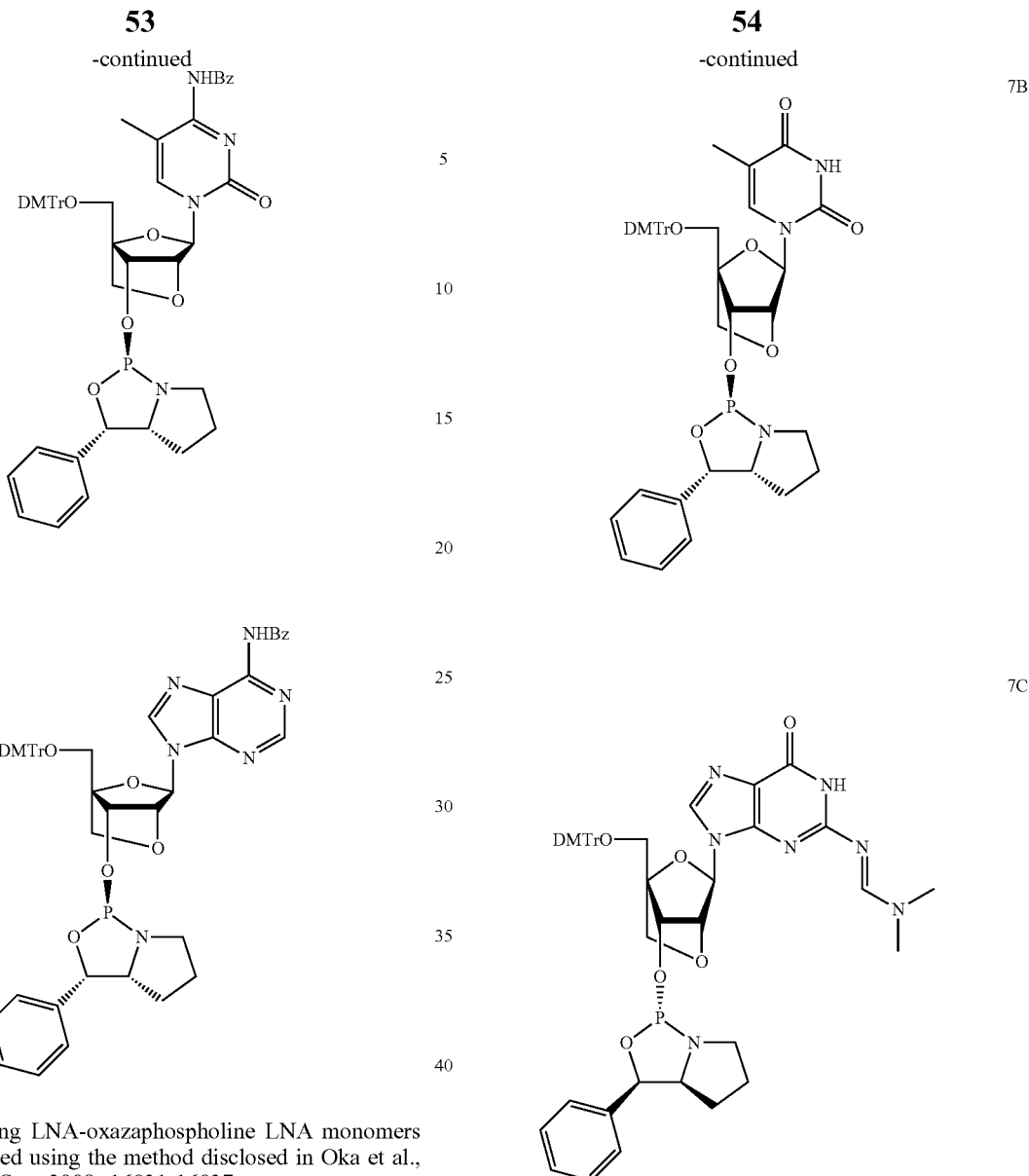
The following LNA-oxazaphospholine LNA monomers were synthesized using the method disclosed in Oka et al., J. Am. Chem. Soc. 2008; 16031-16037:
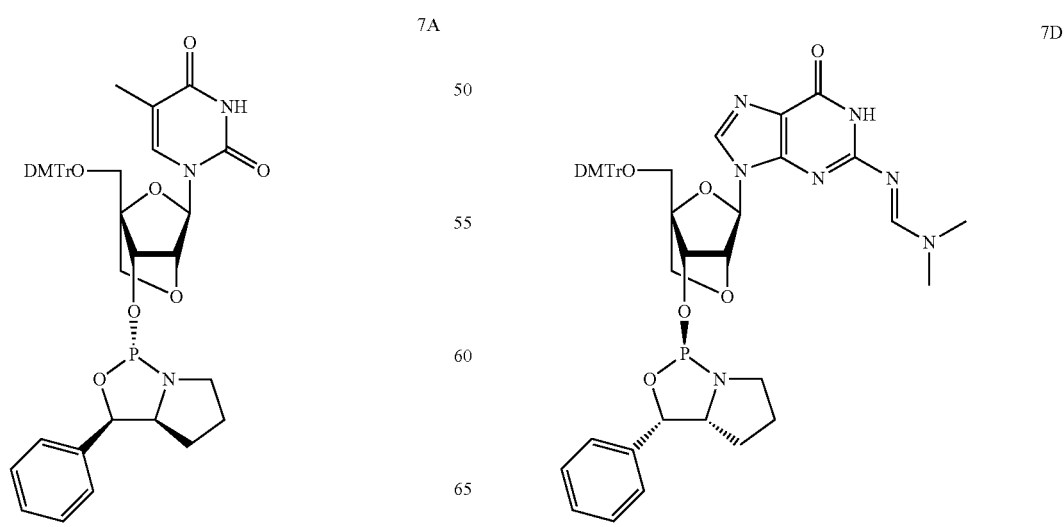

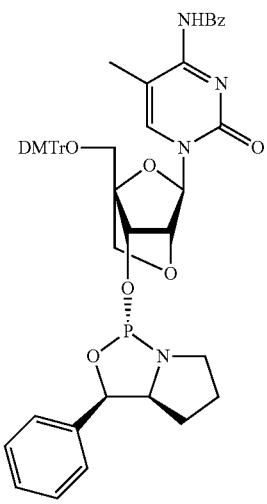

7E

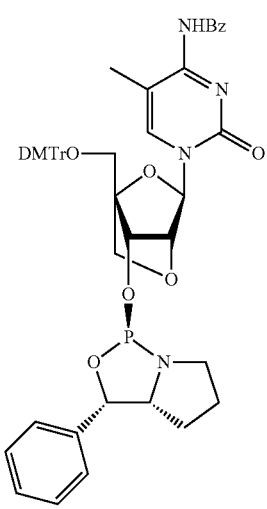

7F

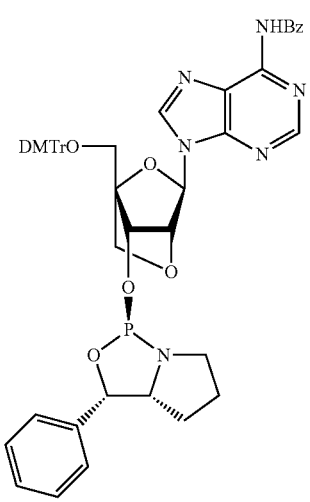

7G

-continued

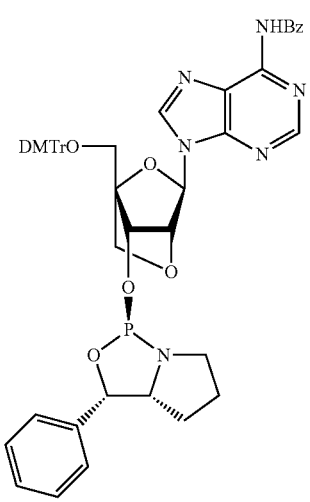

7H

The above LNA monomers were used in oligonucleotide synthesis and shown to give stereocontrolled phosphoramidite LNA oligonucleotides as determined by HPLC.

Example 2

The following LNA oligonucleotides targeting Myd88 are synthesized.

```
                                                    (SEQ ID NO 1)
A_x^m C_x T_x g_x c_x t_x t_x t_x c_x c_x a_x c_x t_x^m C_x T_x G  (Parent #1)

A_x^m C_x T_x g_x c_x t_x t_x t_x c_x c_x a_x c_x t_x^m C_x T_x G  (Parent #1)

A_x^m C_x T_x g_x c_s t_x t_x t_x c_x c_x a_x c_x t_x^m C_x T_x G  (Comp #2)

A_x^m C_x T_x g_x c_x t_x t_x t_x c_s c_x a_x c_x t_x^m C_x T_x G  (Comp #3)

A_x^m C_x T_x g_x c_s t_x t_x t_x c_x c_x a_x c_x t_x^m C_x T_x G  (Comp #4)

A_x^m C_x T_x g_x c_r t_x t_x t_x c_x c_x a_x c_x t_x^m C_x T_x G  (Comp #5)

A_x^m C_x T_x g_x c_x t_x t_x t_x c_x c_x a_x c_x t_x^m C_x T_x G  (Comp #6)

A_x^m C_x T_x g_x c_x t_x t_x t_x c_x c_x a_x c_r t_x^m C_x T_x G  (Comp #7)

A_x^m C_x T_x g_x c_s t_x t_x t_x c_s c_x a_x c_x t_x^m C_x T_x G  (Comp #8)

A_x^m C_x T_x g_x c_s t_x t_x t_x c_x c_x a_x c_s t_x^m C_x T_x G  (Comp #9)

A_x^m C_x T_x g_x c_s t_x t_x t_x c_s c_x a_x c_x t_x^m C_x T_x G  (Comp #10)

A_x^m C_x T_x g_x c_r t_x t_x t_x c_s c_x a_x c_s t_x^m C_x T_x G  (Comp #11)

A_x^m C_x T_x g_x c_r t_x t_x t_x c_x c_x a_x c_x t_x^m C_x T_x G  (Comp #12)

A_x^m C_x T_x g_x c_r t_x t_x t_x c_x c_x a_x c_r t_x^m C_x T_x G  (Comp #13)

A_x^m C_x T_x g_x c_r t_x t_x t_x c_x c_x a_x c_r t_x^m C_x T_x G  (Comp #14)

A_x^m C_x T_x g_x c_x t_x t_x t_x c_x c_x a_x c_r t_x^m C_x T_x G  (Comp #15)

A_x^m C_x T_x g_x c_x t_x t_x t_x c_x c_x a_x c_s t_x^m C_x T_x G  (Comp #16)

A_x^m C_x T_x g_x c_x t_x t_x t_x c_s c_x a_x c_r t_x^m C_x T_x G  (Comp #17)

A_x^m C_x T_x g_x c_x t_x t_x t_x c_x c_x a_x c_x t_x^m C_x T_x G  (Comp #18)

A_x^m C_x T_x g_x c_x t_x t_x t_x c_x c_x a_x c_r t_x^m C_x T_x G  (Comp #19)

A_x^m C_x T_x g_x c_x t_x t_x t_x c_x c_x a_x c_x t_x^m C_x T_x G  (Comp #20)
```

-continued $A_x{}^mC_xT_xg_xc_st_xt_xt_xc_xc_xa_xc_st_x{}^mC_xT_xG$ (Comp #21)

$A_x{}^mC_xT_xg_xc_rt_xt_xt_xc_xc_xa_xc_rt_x{}^mC_xT_xG$ (Comp #22)

$A_x{}^mC_xT_xg_xc_rt_xt_xt_xc_xc_xa_xc_t_x{}^mC_xT_xG$ (Comp #23)

$A_x{}^mC_xT_xg_xc_rt_xt_xt_xc_xc_xa_xc_st_x{}^mC_xT_xG$ (Comp #24)

$A_x{}^mC_xT_xg_xc_rt_xt_xt_xc_xc_xa_xc_st_x{}^mC_xT_xG$ (Comp #25)

$A_x{}^mC_xT_xg_xc_t_xt_xt_xc_xc_xa_xc_t_x{}^mC_xT_xG$ (Comp #26)

$A_x{}^mC_xT_xg_xc_rt_xt_xt_xc_rc_xa_xc_t_x{}^mC_xT_xG$ (Comp #27)

Capital letters are beta-D-oxy LNA nucleosides, small letters are DNA nucleosides Subscript x=randomly incorporated phosphorothioate linkage from a racemic mixture of Rp and Sp monomers.

Subscript s=stereocontrolled phosphoramidite linkage from a Sp monomer

Subscript r=stereocontrolled phosphoramidite linkage from a Rp monomer

Superscript m preceding a capital C represents 5-methyl cytosine LNA nucleoside

Example 3

Parent compound #1 has been determined as a hepatotoxic in mice. Compounds #1-27# are evaluated for their hepatotoxicity in an in vivo assay: 5 NMRI female mice per group are used, 15 mg/kg of compound are administered to each mouse on days 0, 3, 7, 10 and 14, and sacrificed on day 16. Serum ALT is measured. Hepatotoxicity may also be measured as described in EP 1 984 381, example 41 with the exception that NMRI mice are used, or using an in vitro hepatocyte toxicity assay.

Example 4

The following LNA oligonucleotides identified as toxic in Seth et al J. Med. Chem 2009, 52, 10-13 are synthesized.

(SEQ ID NO 2)
$T_x{}^mC_xa_xt_xg_xg_xc_xt_xg_xc_xa_xg_x{}^mC_xT$ (Parent #28)

$T_x{}^mC_xa_xt_sg_xg_xc_xt_xg_xc_xa_xg_x{}^mC_xT$ (Camp #29)

$T_x{}^mC_xa_xt_rg_xg_xc_xt_xg_xc_xa_xg_x{}^mC_xT$ (Camp #31)

$T_x{}^mC_xa_xt_xg_sg_xc_xt_xg_xc_xa_xg_x{}^mC_xT$ (Camp #32)

$T_x{}^mC_xa_xt_sg_xg_xc_xtxg_xc_xa_xg_x{}^mC_xT$ (Comp #33)

$T_x{}^mC_xa_xt_xg_xg_xc_xt_xg_xc_xa_xg_x{}^mC_xT$ (Camp #34)

$T_x{}^mC_xa_xt_sg_xg_xc_xt_xg_xc_xa_xg_x{}^mC_xT$ (Comp #35)

$T_x{}^mC_xa_xt_xg_sg_xc_xt_xg_xc_xa_xg_x{}^mC_xT$ (Camp #36)

$T_x{}^mC_xa_xt_rg_xg_xc_xt_xg_xc_xa_xg_x{}^mC_xT$ (Camp #37)

$T_x{}^mC_xa_xt_sg_xg_xc_xt_xg_xc_ra_xg_x{}^mC_xT$ (Comp #38)

$T_x{}^mC_xa_xt_sg_xg_rc_xt_xg_xc_ra_xg_x{}^mC_xT$ (Comp #39)

$T_x{}^mC_xa_xt_xg_xg_xc_xt_xg_xc_ra_xg_x{}^mC_xT$ (Camp #40)

$T_x{}^mC_xa_xt_sg_xg_rc_xt_xg_xc_sa_xg_x{}^mC_xT$ (Comp #41)

$T_x{}^mC_xa_xt_sg_xg_xc_xt_xg_xc_ra_xg_x{}^mC_xT$ (Comp #42)

$T_x{}^mC_xa_xt_rg_xg_xc_xt_xg_xc_xa_xg_x{}^mC_xT$ (Comp #43)

$T_x{}^mC_xa_xt_xg_xg_xc_xt_xg_xc_xa_xg_x{}^mC_xT$ (Comp #44)

$T_x{}^mC_xa_xt_xg_xg_xc_xt_xg_xc_xa_xg_x{}^mC_xT$ (Comp #45)

$T_x{}^mC_xa_xt_rg_xg_xc_xt_xg_xc_xa_xg_x{}^mC_xT$ (Comp #46)

$T_x{}^mC_xa_xt_rg_xg_xc_xt_xg_xc_xa_xg_x{}^mC_xT$ (Comp #47)

$T_x{}^mC_xa_xt_rg_xg_xc_xt_xg_xc_ra_xg_x{}^mC_xT$ (Comp #48)

$T_x{}^mC_xa_xt_xg_xg_xc_xt_xg_xc_xa_xg_x{}^mC_xT$ (Comp #49)

$T_x{}^mC_xa_xt_rg_sg_xc_xt_xg_xc_xa_xg_x{}^mC_xT$ (Comp #50)

$T_x{}^mC_xa_xt_rg_xg_xc_xt_xg_xc_sa_xg_x{}^mC_xT$ (Comp #51)

$T_x{}^mC_xa_xt_rg_xg_sc_xt_xg_xc_sa_xg_x{}^mC_xT$ (Comp #52)

$T_x{}^mC_xa_xt_xg_xg_xc_xt_xg_xc_sa_xg_x{}^mC_xT$ (Comp #53)

$T_x{}^mC_xa_xt_rg_sg_xc_xt_xg_xc_sa_xg_x{}^mC_xT$ (Comp #54)

$T_x{}^mC_xa_xt_rg_xg_xc_xt_xg_xc_sa_xg_x{}^mC_xT$ (Comp #55)

Capital letters are beta-D-oxy LNA nucleosides, small letters are DNA nucleosides Subscript x=randomly incorporated phosphorothioate linkage from a racemic mixture of Rp and Sp monomers.

Subscript s=stereocontrolled phosphoramidite linkage from a Sp monomer

Subscript r=stereocontrolled phosphoramidite linkage from a Rp monomer

Superscript m preceding a capital C represents 5-methyl cytosine LNA nucleoside

Example 5

Parent compound #28 has been determined as a hepatotoxic in mice. Compounds #28-27# are evaluated for their hepatotoxicity in an in vivo assay: 5 NMRI female mice per group are used, 15 mg/kg of compound are administered to each mouse on days 0, 3, 7, 10 and 14, and sacrificed on day 16. Serum ALT is measured. Hepatotoxicity may also be measured as described in EP 1 984 381, example 41 with the exception that NMRI mice are used, or using an in vitro hepatocyte toxicity assay.

Example 6. Tolerance and Tissue Content of Compound Libraries with 3 Fixed PS Internucleoside Linkages In Vivo C57BL6/J mice (5 animals/gr) were injected iv on day 0 with a single dose saline or 30 mg/kg LNA-antisense oligonucleotide in saline (seq ID #1, 10, or 14) and sacrificed on day 8. Serum was collected and ALT was measured for all groups. The oligonucleotide content was measured in the LNA dosed groups using ELISA method.

Conclusions:

The hepatotoxic potential (ALT) for the subgroups of LNA oligonucleotides where 3 phosphorothioate internucleoside linkages are fixed in either S (Comp #10) or R (Comp #14) configuration was compared to the ALT for parent mixture of diastereoisomers (Comp #1) with all internucleoside linkages as mixtures of R and S configuration. It is seen (FIG. 3) that for one subgroup (Comp #14) the ALT readout is significantly lower than for the parent mixture (Comp #1) and for the other subgroup of compounds (Comp #10) ALT reading is similar to parent. Moreover, the liver uptake profile (FIG. 4a) show that the subgroup of LNA oligonucleotides with low ALT readout (Comp #14) is taken up into the liver to the same extend as the parent LNA mixture (Comp #1) whereas the other subgroup (Comp #10) with ALT comparable to the parent mixture (Comp #1) is taken up less into the liver. Kidney uptake (FIG. 4b) is similar for parent LNA (Comp #1) and one subgroup (Comp #10) and higher for the other subgroup of LNA oligonucleotides (Comp #14). Uptake into the spleen is similar for all 3 groups of compounds (FIG. 4c). Generally it is seen that fixing the stereochemistry in some positions and thereby generating a subgroup of LNA oligonucleotides induces differences for properties such as uptake and hepatotoxic potential compared to the parent mixture of LNA oligonucleotides.

Materials and Methods:
Experimental Design:

TABLE 2

| Groups | Compounds | Day 1 | Day 2 | Day 3 | Day 5 | Day 8 |
|---|---|---|---|---|---|---|
| 1 | Saline | Body weight Dosing | Body weight | Body weight | Body weight | Blood Body weight Termination |
| 2 | Comp #1 30 mg/kg | Body weight Dosing | Body weight | Body weight | Body weight | Blood Body weight Termination |
| 3 | Comp #10 30 mg/kg | Body weight Dosing | Body weight | Body weight | Body weight | Blood Body weight Termination |
| 4 | Comp #14 30 mg/kg | Body weight Dosing | Body weight | Body weight | Body weight | Blood Body weight Termination |

Dose Administration.

C57BL/6JBom female animals, app. 20 g at arrival, were dosed with 10 ml per kg BW (according to day 0 bodyweight) i.v. of the compound formulated in saline or saline alone according to Table 2.

Sampling of Liver and Kidney Tissue.

The animals were anaesthetised with 70% $CO_2$-30% $O_2$ and sacrificed by cervical dislocation according to Table 2. One half of liver and one kidney was frozen and used for tissue analysis.

Oligonucleotide content in liver and kidney was measured by sandwich ELISA method.

ALT Levels were Measured

Example 7 RNase H Activity of Chirally Defined Phosphorothioate LNA Gapmers

The parent compound used, 3833 was used:

(SEQ ID NO 3)
5'-$G_s{}^mC_sa_st_st_sg_sg_st_sa_st_sT_s{}^mC_sA$-3'

Wherein capital letters represent beta-D-oxy-LNA nucleosides, lower case letters represent DNA nucleosides, subscript s represents random s or r phosphorothioate linkages (not chirally defined during oligonucleotide synthesis), and superscript m prior to C represents 5-methyl cytosine LNA nucleoside.

A range of fully chirally defined variants of 3833 were designed with unique patterns of R and S at each of the 12 internucleoside positions, as illustrated by either an S or an R. The RNaseH recruitment activity and cleavage pattern was determined using human RNase H, and compared to the parent compound 3833 (chirality mix) as well as a fully phosphodiester linked variant of 3833 (full PO), and a 3833 compound which comprises of phosphodiester linkages within the central DNA gap region and random PS linkages in the LNA flank (PO gap).

Compounds:

| Oligo no. | Chirality of nucleo base linkages | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| 16614 | S | R | S | R | R | S | R | S | S | S | R | R |
| 16615 | S | R | S | S | R | S | R | S | R | S | S | S |
| 16617 | S | R | S | R | S | S | R | R | R | S | R | R |
| 16618 | S | R | R | S | S | S | R | S | S | S | R | R |
| 16620 | S | R | R | S | R | R | R | R | S | S | S | R |
| 16621 | S | R | R | S | S | R | R | S | R | S | S | S |
| 16622 | S | R | R | R | R | R | S | S | R | S | S | R |
| 16623 | S | S | R | R | S | S | S | R | S | R | S | S |
| 16625 | S | R | S | S | S | S | S | R | S | R | R | S |
| 16626 | S | S | S | S | S | R | S | R | S | R | S | S |
| 16627 | S | R | S | S | S | S | R | R | R | R | R | S |
| 16629 | S | R | R | R | S | S | R | S | S | S | S | S |
| 16631 | S | R | R | S | R | S | R | S | R | S | S | R |
| 16633 | R | S | R | S | R | R | R | R | R | S | S | S |
| 16635 | R | S | S | R | S | R | S | R | R | R | R | R |
| 16636 | S | R | R | S | R | R | R | R | S | R | S | S |
| 16639 | S | S | S | R | R | S | S | R | S | S | S | R |
| 16641 | S | S | S | S | R | R | R | S | R | R | R | R |
| 16645 | S | R | S | R | S | R | S | S | R | R | R | R |
| 16648 | S | S | S | R | R | R | S | S | S | S | S | S |
| 16649 | S | S | R | S | S | R | S | R | S | R | S | R |
| 16650 | S | R | S | R | S | R | S | R | S | R | S | R |
| 16652 | S | S | S | S | R | R | R | S | S | R | S | R |
| 16655 | S | R | S | R | S | S | R | S | R | R | S | S |
| 16657 | S | R | S | R | S | R | S | R | S | R | S | S |
| 16658 | S | S | R | R | S | R | R | S | S | R | S | S |
| 16660 | S | S | R | R | R | R | R | R | R | S | S | S |
| 16663 | S | R | S | R | S | S | R | R | S | S | S | S |
| 16666 | S | R | S | R | R | S | R | S | R | S | R | R |
| 16667 | S | R | S | R | S | R | S | R | S | R | S | R |
| 16668 | S | R | S | R | S | R | S | R | S | S | S | S |
| 16669 | S | R | R | S | S | R | S | R | S | R | S | S |
| 16671 | S | S | S | R | R | S | R | R | S | S | S | S |
| 16673 | R | S | S | S | R | R | S | R | R | S | S | S |
| 16674 | S | R | S | S | R | S | S | S | S | S | S | S |
| 16675 | S | S | R | R | S | S | R | R | S | S | S | R |
| 16676 | S | S | S | S | R | S | S | R | R | R | S | R |
| 16677 | S | R | S | R | S | S | R | S | R | S | S | R |
| 16683 | S | S | R | R | R | S | S | S | R | S | R | S |
| 16684 | S | R | R | S | S | S | R | S | R | S | S | S |
| 16685 | S | R | R | S | S | S | R | S | R | S | R | S |
| 16687 | S | R | R | S | R | S | S | S | R | R | R | S |
| 16688 | S | R | S | S | R | S | R | R | S | S | S | S |
| 16692 | R | S | S | S | R | R | R | R | R | S | S | R |
| 16693 | S | S | S | S | R | S | S | R | S | S | R | S |
| 16694 | S | R | R | R | R | R | R | S | R | S | S | R |
| 16697 | S | R | R | R | R | S | S | R | S | S | S | S |
| 16699 | S | R | S | S | R | S | S | R | S | S | R | S |
| 16701 | S | S | S | S | R | S | R | R | R | R | R | R |
| 16702 | S | S | S | S | R | R | R | S | R | S | S | R |
| 16704 | S | R | R | R | R | S | R | S | R | S | S | R |
| 16709 | S | S | R | S | S | R | S | R | S | R | S | S |
| 17298 | | R | | | R | R | | | R | | | |
| 17299 | | S | | | S | S | | | S | | | |
| 17300 | | R | | | S | S | | | R | | | |
| 17301 | | S | | | R | R | | | S | | | |
| 3833 | | | | | | Chirality mix | | | | | | |
| 3833 | | | | | | Chirality mix* | | | | | | |
| 18946 | | | | | | PO in the gap* | | | | | | |
| 18947 | | | | | | Full PO* | | | | | | |

All of the compounds were assessed in a single experiment except where marked * when a separate experiment was performed Experimental:
LNA Oligonucleotide Mediated Cleavage of RNA by RNase H1 (Recombinant Human).

LNA oligonucleotide 15 pmol and 5'fam labeled RNA 45 pmol was added to 13 μL of water. Annealing buffer 6 μL (200 mM KCl, 2 mM EDTA, pH 7.5) was added and the temperature was raised to 90° C. for 2 min. The sample was allowed to reach room temperature and added RNase H enzyme (0, 15 U) in 3 μL of 750 mM KCl, 500 mM Tris-HCl, 30 mM MgCl$_2$, 100 mM dithiothreitol, pH 8.3). The sample was kept at 37° C. for 30 min and the reaction was stopped by adding EDTA solution 4 μL (0.25 M).

AIE-HPLC of Cleaved RNA Samples

The sample 15 μL was added to 200 μL of buffer A (10 mM NaClO4, 1 mM EDTA, 20 mM TRIS-HCL pH 7.8). The sample was subjected to AIE-HPLC injection volume 50 μL (Column DNA pac 100 2×250, gradient 0 min. 0.25 mL/min. 100% A, 22 min. 22% B (1 mM NaClO4, 1 mM EDTA, 20 mM TRIS-HCL pH 7.8), 25 min. 0.25 mL/min. 100% B, 30 min. 0.25 mL/min. 100% B, 31 min. 0.5 mL/min. 0% B, 35 min. 0.25 mL/min. 0% B, 40 min. 0.25 mL/min. 0% B. Signal detention fluorescens emission at 518 nm excitation at 494 nm.

Results

LNA oligonucleotide with the sequence G$^m$CattggtatT-$^m$CA all phosphorus linkages thiolated. The specific chirality of the thiophosphate in the linkages are noted. Where nothing are noted the chirality are a mix of R and S. Under the AIE-HPLC retention time the percentage's the peaks areas of the sum the all peak areas are listed. The ranking number of the activity of the different LNA-oligonucleotides are calculated from the % of full length RNA left after the enzyme reaction the chirality mixed LNA oligonucleotide 3833 divided with what was left of the RNA for the other LNA oligonucleotides.

| Oligo no. | AIE HPLC retention time (% of total) | | | | | | Full length % | Full length 3833/chiral full length 3833 |
|---|---|---|---|---|---|---|---|---|
| | 11.05 | 11.367 | 11.742 | 12.3 | 12.75 | 12.942 | 15.017 | |
| 16614 | 1.9 | 19.3 | 3.5 | 63.4 | 0.0 | 0.0 | 11.9 | 4.4 |
| 16615 | | | | | | | | |
| 16617 | 0.7 | 18.6 | 4.1 | 44.4 | 5.8 | 7.0 | 19.5 | 2.7 |
| 16618 | 2.2 | 16.1 | 6.1 | 45.9 | 5.1 | 8.1 | 16.5 | 3.2 |
| 16620 | 1.1 | 8.8 | 14.5 | 26.4 | 4.0 | 31.4 | 13.9 | 3.8 |
| 16621 | 2.2 | 1.8 | 32.9 | 37.4 | 0.0 | 11.5 | 14.2 | 3.7 |
| 16622 | 2.3 | 57.1 | 15.5 | 16.7 | 1.6 | 2.1 | 4.7 | 11.2 |
| 16623 | 2.8 | 3.7 | 22.9 | 60.7 | 1.7 | 3.6 | 4.7 | 11.2 |
| 16625 | 2.7 | 3.2 | 20.7 | 28.9 | 2.8 | 20.6 | 21.1 | 2.5 |
| 16626 | 1.3 | 3.2 | 4.6 | 34.0 | 6.0 | 30.1 | 20.9 | 2.5 |
| 16627 | 1.8 | 3.8 | 26.4 | 19.0 | 4.2 | 29.8 | 15.0 | 3.5 |
| 16629 | 1.7 | 2.4 | 36.3 | 38.6 | 2.6 | 5.7 | 12.8 | 4.1 |
| 16631 | 2.6 | 55.3 | 7.8 | 6.5 | 14.9 | 3.8 | 9.2 | 5.7 |
| 16633 | 0.0 | 50.3 | 7.1 | 4.8 | 6.4 | 18.8 | 12.5 | 4.2 |
| 16635 | 1.8 | 7.2 | 64.9 | 7.1 | 11.1 | 4.0 | 3.9 | 13.5 |
| 16636 | 2.1 | 3.8 | 8.9 | 6.4 | 27.9 | 11.6 | 39.3 | 1.3 |
| 16639 | 3.8 | 17.9 | 71.3 | 5.3 | 0.0 | 0.0 | 1.7 | 30.6 |
| 16641 | 1.9 | 41.7 | 10.3 | 10.7 | 2.5 | 13.5 | 19.4 | 2.7 |
| 16645 | 2.2 | 14.1 | 39.8 | 8.6 | 0.0 | 19.2 | 16.0 | 3.3 |
| 16648 | 1.2 | 3.3 | 22.2 | 55.7 | 1.8 | 2.6 | 13.2 | 3.9 |
| 16649 | 2.4 | 37.4 | 3.7 | 28.2 | 7.6 | 0.0 | 20.8 | 2.5 |
| 16650 | 1.3 | 5.6 | 5.6 | 58.3 | 0.0 | 22.3 | 6.8 | 7.7 |
| 16652 | 2.8 | 3.3 | 10.4 | 5.1 | 9.7 | 43.0 | 25.8 | 2.0 |
| 16655 | 0.0 | 3.5 | 3.8 | 20.2 | 4.7 | 21.2 | 46.5 | 1.1 |
| 16657 | 0.0 | 12.2 | 73.4 | 3.5 | 7.8 | 0.0 | 3.1 | 16.8 |
| 16658 | 0.0 | 15.9 | 34.2 | 37.0 | 0.9 | 2.4 | 9.6 | 5.5 |
| 16660 | 0.0 | 0.0 | 0.0 | 0.0 | 0.0 | 0.0 | 100.0 | 0.5 |
| 16663 | 0.0 | 4.5 | 38.3 | 25.9 | 7.5 | 4.9 | 19.0 | 2.7 |
| 16666 | 0.0 | 2.0 | 76.0 | 3.7 | 0.0 | 0.0 | 18.3 | 2.9 |
| 16667 | 0.0 | 31.5 | 30.1 | 25.5 | 0.0 | 9.3 | 3.7 | 14.3 |
| 16668 | 0.0 | 4.7 | 4.7 | 61.3 | 0.0 | 21.9 | 7.5 | 7.0 |
| 16669 | 0.0 | 3.7 | 76.3 | 6.4 | 1.9 | 2.6 | 9.1 | 5.7 |
| 16671 | | | | | | | | |
| 16673 | 0.0 | 9.1 | 15.7 | 31.1 | 0.0 | 3.7 | 40.4 | 1.3 |
| 16674 | 0.0 | 0.0 | 0.0 | 7.8 | 0.0 | 0.0 | 92.2 | 0.6 |
| 16675 | 0.0 | 15.4 | 20.5 | 25.3 | 4.0 | 21.9 | 12.9 | 4.1 |
| 16676 | 0.0 | 1.6 | 29.2 | 33.1 | 0.0 | 17.2 | 18.9 | 2.8 |
| 16677 | 2.1 | 36.5 | 7.0 | 47.6 | 0.0 | 5.2 | 1.6 | 32.4 |
| 16683 | 1.5 | 17.8 | 34.3 | 20.2 | 2.8 | 2.3 | 20.9 | 2.5 |
| 16684 | 1.2 | 13.6 | 1.6 | 35.4 | 8.6 | 0.0 | 39.5 | 1.3 |
| 16685 | 0.0 | 3.4 | 78.6 | 7.4 | 2.1 | 2.2 | 6.3 | 8.3 |
| 16687 | 1.1 | 54.8 | 8.9 | 7.4 | 1.0 | 6.8 | 19.9 | 2.6 |
| 16688 | 1.1 | 16.8 | 55.1 | 3.4 | 6.3 | 12.1 | 5.2 | 10.1 |
| 16692 | 0.0 | 4.4 | 33.2 | 51.1 | 3.0 | 5.9 | 2.4 | 21.5 |
| 16693 | 0.0 | 4.4 | 30.4 | 28.7 | 0.0 | 28.9 | 7.6 | 6.8 |
| 16694 | 0.0 | 5.2 | 37.6 | 20.8 | 2.2 | 17.3 | 16.9 | 3.1 |
| 16697 | | | | | | | | |
| 16699 | 1.5 | 1.6 | 17.5 | 19.3 | 6.8 | 9.0 | 44.3 | 1.2 |
| 16701 | 0.0 | 4.2 | 6.4 | 44.2 | 0.0 | 29.4 | 15.7 | 3.3 |
| 16702 | 0.0 | 27.3 | 20.4 | 22.9 | 1.2 | 8.7 | 19.5 | 2.7 |
| 16704 | 0.0 | 3.2 | 52.4 | 3.3 | 1.4 | 2.8 | 36.9 | 1.4 |
| 16709 | 8.5 | 31.4 | 4.1 | 2.3 | 8.7 | 25.0 | 20.0 | 2.6 |

-continued

| | AIE HPLC retention time (% of total) | | | | | | Full length % | Full length 3833/chiral full length |
|---|---|---|---|---|---|---|---|---|
| Oligo no. | 11.05 | 11.367 | 11.742 | 12.3 | 12.75 | 12.942 | 15.017 | 3833 |
| 17298 | 0.0 | 12.0 | 25.1 | 44.4 | 4.1 | 11.7 | 2.7 | 19.2 |
| 17299 | | | | | | | | |
| 17300 | | | | | | | | |
| 17301 | 1.8 | 17.2 | 2.7 | 4.7 | 8.9 | 16.2 | 48.5 | 1.1 |
| 3833 | 1.0 | 6.8 | 13.7 | 11.1 | 3.9 | 11.2 | 52.3 | 1.0 |
| 3833 | | | | | | | 10 | 1 |
| 18946 | 2.4 | 8.3 | 29.9 | 18.3 | 10.9 | 10.6 | 19.6 | 0.5 |
| 18947 | 0.0 | 8.8 | 34.0 | 21.6 | 10.5 | 10.5 | 14.6 | 0.7 |

Conclusion

The chirality of the phosphorothioate linkages of the LNA oligonucleotide are randomly chosen except for the last 5"coupling where the S chirality were selected and the LNA oligonucleotides where spot chirality was chosen 17298-17301. The full diester and diester only in the gap version of the LNA oligonucleotide have less activity than the mixed chiral version 3833. The chiral sequence enhances the activation and cleavage of the RNA. For most of the specific chiral LNA oligonucleotides the activation of RNaseH1 worked better than for the chirality mixed 3833. The best of the specific sequences initiated substantial more cleavage of RNA than 3833 (98.4% versus 47.7% after 30 minutes). A characteristic of each of the specific LNA oligonucleotides are their unique cleavage pattern of the RNA varying form one to several cleavage points.

Example 8 In Vitro Toxicity Screening in Primary Hepatocytes

Mouse Liver Perfusion

Primary mouse hepatocytes were isolated from 10- to 13-week old male C57Bl6 mice by a retrograde two-step collagenase liver perfusion. Briefly, fed mice were anaesthetized with sodium pentobarbital (120 mg/kg, i.p.). Perfusion tubing was inserted via the right ventricle into the v. cava caudalis. Following ligation of the v. cava caudalis distal to the v. iliaca communis, the portal vein was cut and the two-step liver perfusion and cell isolation was performed. The liver was first perfused for 5 min with a pre-perfusing solution consisting of calcium-free, EGTA (0.5 mM)-supplemented, HEPES (20 mM)-buffered Hank's balanced salt solution, followed by a 12-min perfusion with NaHCO3 (25 mM)-supplemented Hank's solution containing CaCl2 (5 mM) and collagenase (0.2 U/ml; Collagenase Type II, Worthington). Flow rate was maintained at 7 ml/min and all solutions were kept at 37° C. After in situ perfusion, the liver was excised, the liver capsule was mechanically opened, the cells were suspended in William's Medium E (WME) without phenol red (Sigma W-1878), and filtered through a set of nylon cell straines (40- and 70-mesh). Dead cells were removed by a Percoll (Sigma P-4937) centrifugation step (percoll density: 1.06 g/ml, 50 g, 10 min) and an additional centrifugation in WME (50×g, 3 min).

Compounds Used

5'-$^m$C$_x$A$_x$$^m$C$_x$a$_x$t$_x$t$_x$c$_x$c$_x$t$_x$t$_x$g$_x$c$_x$t$_x$$^m$C$_x$T$_x$G-3' (Parent #56)
(SEQ ID NO: 4)

5'-$^m$C$_x$A$_x$$^m$C$_x$a$_x$t$_x$t$_s$c$_x$c$_x$t$_x$t$_s$g$_x$c$_x$t$_s$$^m$C$_x$T$_x$G-3' (Comp #57)
(SEQ ID NO: 4)

5'-$^m$C$_x$A$_x$$^m$C$_x$a$_x$txt$_r$c$_x$c$_x$t$_x$t$_r$g$_x$c$_x$t$_r$$^m$C$_x$T$_r$G-3' (Comp #58)
(SEQ ID NO: 4)

5'-$^m$C$_x$A$_x$$^m$C$_x$a$_x$t$_s$t$_s$c$_s$c$_x$t$_x$t$_s$g$_s$c$_x$t$_x$$^m$C$_x$T$_x$G-3' (Comp #59)
(SEQ ID NO: 4)

5'-$^m$C$_x$A$_x$$^m$C$_x$a$_x$t$_x$t$_r$c$_r$c$_x$t$_x$t$_r$g$_r$c$_x$t$_x$$^m$C$_x$T$_x$G-3' (Comp #60)
(SEQ ID NO: 4)

Capital letters are beta-D-oxy LNA nucleosides, small letters are DNA nucleosides Subscript x=randomly incorporated phosphorothioate linkage from a racemic mixture of Rp and Sp monomers.

Subscript s=stereocontrolled phosphoramidite linkage from a Sp monomer

Subscript r=stereocontrolled phosphoramidite linkage from a Rp monomer

Superscript m preceding a capital C represents 5-methyl cytosine LNA nucleoside.

Hepatocyte Culturing

For cell culture, primary mouse hepatocytes were suspended in WME supplemented with 10% fetal calf serum, penicillin (100 U/ml), streptomycin (0.1 mg/ml) at a density of approx. 5×10$^6$ cells/ml and seeded into collagen-coated 96-well plates (Becton Dickinson AG, Allschwil, Switzerland) at a density of 0.25×10$^6$ cells/well. Cells were precultured for 3 to 4 h allowing for attachment to cell culture plates before start of treatment with oligonucleotides. Oligonucleotides dissolved in PBS were added to the cell culture and left on the cells for 3 days. Cytotoxicity levels were determined by measuring the amount of Lactate dehydrogenase (LDH) released into the culture media using a Cytotoxicity Detection Kit (Roche 11644793001, Roche Diagnostics GmbH Roche Applied Science Mannheim, Germany) according to the manufacturers protocol. For the determination of cellular ATP levels we used the CellTiter-Glo® Luminescent Cell Viability Assay (G9242, Promega Corporation, Madison Wis., USA) according to the manufacturers protocol. Each sample was tested in triplicate.

Target Knock-Down Analysis mRNA purification from mouse hepatocytes RNeasy 96 Kit (Qiagen, Hombrechtikon, Switzerland) including an RNAse free DNAse I treatment according to the manufacturer's instructions. cDNA was synthesized using iScript single strand cDNA Synthesis Kit (Bio-Rad Laboratories AG, Reinach, Switzerland). Quantitative real-time PCR assays (qRT-PCR) were performed using the Roche SYBR Green I PCR Kit and the Light Cycler 480 (Roche Diagnostics, Rotkreuz, Switzerland) with specific DNA primers. Analysis was done by the ΔCt threshold method to determine expression relative to RPS12 mRNA. Each analysis reaction was performed in duplicate, with two samples per condition. The results are shown in FIGS. 5 & 6. Compounds #58 and #60 have significantly reduced toxicity whilst retaining effective antisense activity against the target (Myd88). These compounds comprise Rp stereodefined phosphorothioate linkages.

Example 9 Nephrotoxicity Screening Assay

The same compounds as used in example 6 and 8 were used in the following RPTEC-TERT1 culture, oligonucleotide treatment and viability assay:

RPTEC-TERT1 (Evercyte GmbH, Austria) were cultured according to the manufacturer's instructions in PTEC medium (DMEM/F12 containing 1% Pen/Strep, 10 mM Hepes, 5.0 μg/ml human insulin, 5.0 μg/ml human transferrin, 8.65 ng/ml sodium selenite, 0.1 μM hydrocortisone, 10 ng/ml human recombinant Epidermal Growth Factor, 3.5 μg/ml ascorbic acid, 25 ng/ml prostaglandin E1, 3.2 μg/ml Triiodo-L-thyronine and 100 μg/ml Geneticin). For viability assays, PTEC-TERT1 were seeded into 96-well plates (Falcon, 353219) at a density of $2 \times 10^4$ cells/well in PTEC medium and grown until confluent prior to treatment with oligonucleotides. Oligonucleotides were dissolved in PBS and added to the cell culture at a final concentration of 10 or 30 μM. Medium was changed and oligonucleotides were added fresh every 3 days. After 9 days of oligonucleotide treatment, cell viability was determined by measurement of cellular ATP levels using the CellTiter-Glo® Luminescent Cell Viability Assay (G7571, Promega Corporation, Madison Wis., USA) according to the manufacturer's protocol. The average ATP concentration and standard deviation of triplicate wells were calculated. PBS served as vehicle control.

The results are shown in FIG. 8. Compound #10 shows reduced nephrotoxicity as compared to the non-stereospecified compound #1 and compound #14. Stereospecified compounds #57, #58, #60 show significantly reduced nephrotoxicity as compared to the parent compound (#56).

Example 10 Mismatch Specificity of Chirally Defined Phosphorothioate LNA Gapmers The experimental procedure used was as described in example 7, with the exception that alternative RNA substrates were used which introduced a mismatch at various positions as compared to the parent 3833 compound. The RNaseH activity against the perfect match RNA substrate and the mismatch RNA substrates was determined.

TABLE 3

Effect of mismatches on RNaseH activity of 3833.

| RNA: SEQ ID | RNA Substrate | TM up | Tm down | % full length |
|---|---|---|---|---|
| 20 | ACAGAAUACCAAUGCACAGA | 59.5 | 59.4 | 39.1 |
| 6 | UGAGAAUACCAAUGCUAAGU | 57.8 | 59.8 | |
| 7 | CAGGAAUACCAAUGCAGAGA | 59.2 | 61.8 | 58.3 |
| 8 | AGUGGAUACCAAUGCUGCAG | 53.4 | 55.7 | 54.6 |
| 9 | UUUGGAUACCAAUGCAUAGG | 54.1 | 57.1 | 60.7 |
| 10 | UCUGAGUACCAAUGCCAUGA | 55.0 | 55.5 | 43.7 |

TABLE 3 -continued

Effect of mismatches on RNaseH activity of 3833.

| RNA: SEQ ID | RNA Substrate | TM up | Tm down | % full length |
|---|---|---|---|---|
| 11 | GCUGAAUGCCAAUGCUGAGU | 56.9 | 57.6 | 67.4 |
| 12 | UCUGAAUACCGAUGCUUUAA | 57.3 | 58.0 | 42.8 |
| 13 | UCUGAAUACCAGUGCUUUAA | 56.0 | 57.7 | 43.9 |
| 14 | CUUGUAAUACCAAUGCUAUAA | 51.9 | 52.5 | 48.5 |
| 15 | AAAGAAUACCAAUGUUCUCU | 49.2 | 49.8 | |
| 16 | UAUGAAUACCAUUGUCUUAU | 40.5 | 41.4 | 72.0 |
| 17 | CCGAAUGCCAAUGCAGAGUU | 57.1 | 58.0 | 75.2 |
| 18 | GAUGAAAUACCAAUGUUAACU | 39.6 | 40.8 | |
| 19 | CUGAAUACCAAUGCUGAACUU | 59.0 | 59.9 | 49.9 |

Mismatches are shown by use of a larger font size. RNaseH cleavage analysed after 30 minutes. The cleavage products changes with the position of the mismatch.

TABLE 4

Effect of mismatches on RNaseH activity of stereodefined variants of 3833.

| SEQ ID NO | RNA Substrate | LNA | % Full length | Relative activity of mismatch | Relative activity of full match |
|---|---|---|---|---|---|
| 9 | UUUGGAUACCAAU GCAUAGG | 3833 | 37.7 | 1 | 1 |
| | | 16639 | 25.5 | 1.5 | 30.6 |
| | | 16657 | 7.9 | .8 | 16.8 |
| | | 16685 | 32.8 | 1.2 | 8.3 |
| 12 | UCUGAAUACCGAU GCUUUAA | 3833 | 53.0 | 1 | 1 |
| | | 16650 | 71.7 | 0.7 | 7.7 |
| | | 16668 | 79.5 | 0.7 | 7.0 |
| 13 | UCUGAAUACCAGU GCUUUAA | 3833 | 46.4 | 1 | 1 |
| | | 16635 | 8.5 | 5.4 | 13.5 |
| | | 16639 | 2.6 | 18.0 | 30.6 |
| | | 16657 | 28.3 | 1.6 | 16.8 |
| | | 16685 | 33.8 | 1.4 | 8.3 |

To a perfect match RNA substrate, chirally defined phosphorothioate oligonucleotides tend to activate RNaseH mediated cleavage of RNA more profound than the ASO with mixed chirality. However, chirally defined oligonucleotides of a chosen phosphorothioate (ASO) configuration can be found that have a marked reduced RNaseH cleavage of a mismatch RNA, highlighting the ability to screen libraries of chirally defined variants of an oligonucleotide to identify individual stereodefined compounds which have improved mismatch selectivity.

Example 11

The parent compound used, 4358 was used:

(SEQ ID NO 5)
5'-$G_s mC_s a_s a_s g_s c_s a_s t_s c_s c_s t_s G_s T$ 3'

Wherein capital letters represent beta-D-oxy-LNA nucleosides, lower case letters represent DNA nucleosides, subscript s represents random s or r phosphorothioate linkages (not chirally defined during oligonucleotide synthesis), and superscript m prior to C represents 5-methyl cytosine LNA nucleoside.

A range of fully chirally defined variants of 4358 were designed with unique patterns of R and S at each of the 11 internucleoside positions, as illustrated by either an S or an R. The RNaseH recruitment activity and cleavage pattern was determined using human RNase H, and compared to the parent compound 4358 (chirality mix). The results obtained were as follows:

| Oligo no. | Chirality of nucleobase linkages | | | | | | | | | | | % full length | Full length 4358/full length chiral |
|---|---|---|---|---|---|---|---|---|---|---|---|---|---|
| | 1 | 2 | 3 | 4 | 5 | 6 | 7 | 8 | 9 | 10 | 11 | | |
| 4358 | Chirality mix | | | | | | | | | | | 4.34 | 1.0 |
| 24387 | S | S | S | S | S | S | S | S | S | S | S | 4.30 | 1.01 |
| 24388 | S | S | S | S | S | S | R | S | S | S | S | 2.64 | 1.64 |
| 24389 | S | S | S | R | S | S | S | S | S | S | S | 4.01 | 1.08 |
| 24390 | S | S | R | S | S | S | S | S | S | S | S | 4.14 | 1.05 |

The invention claimed is:

1. A method of reducing the toxicity of an LNA antisense oligonucleotide (parent oligonucleotide), wherein the antisense oligonucleotide is 10-20 nucleotides in length, comprising the steps of;
   a) creating a library of stereodefined oligonucleotide variants (child oligonucleotides) each retaining a nucleobase sequence of at least 10 contiguous nucleotides of the parent oligonucleotide, wherein each child oligonucleotide has a pattern of chiral phosphorothioate linkages that differs from the parent and other child oligonucleotides,
   b) screening the library created in step a) for their in vitro hepatotoxicity in a cell, and
   c) identifying one or more child oligonucleotides present in the library which has a reduced hepatotoxicity in the cell as compared to the parent oligonucleotide.

2. The method according to claim 1, wherein the parent oligonucleotide is an antisense gapmer oligonucleotide.

3. The method according to claim 2, wherein each member of the library of stereodefined oligonucleotide variants comprises at least one stereodefined phosphorothioate internucleoside linkage in the gap-region of the gapmer.

4. The method according to claim 2, wherein each member of the library of stereodefined oligonucleotide variants comprises at least one stereodefined phosphorothioate internucleoside linkage in one or both wing-regions of the gapmer.

5. The method according to claim 1 wherein each member of the library of stereodefined defined oligonucleotide variants comprises at least 2 stereodefined phosphorothioate linkages, wherein the remaining phosphorothioate linkages may optionally be non-stereodefined defined phosphorothioate linkages.

6. The method according to claim 1, wherein all phosphorothioate linkages present in each member of the library of stereodefined defined oligonucleotide variants are stereodefined phosphorothioate linkages.

7. The method according to claim 2, wherein all internucleoside linkages present in each member of the library of stereodefined defined oligonucleotide variants are stereodefined phosphorothioate linkages.

8. The method according to claim 1, wherein each member of the library of stereodefined oligonucleotide variants retains the pattern of modified and unmodified nucleosides present in the parent oligonucleotide.

9. The method according to claim 2, wherein the parent gapmer oligonucleotide is a LNA gapmer.

10. The method according to claim 1, wherein the method further comprises the step of determining the IC50 of the one or more of the child oligonucleotides identified in step c).

11. The method according to claim 10, wherein the child oligonucleotides identified in step c. retain at least 25% of the IC50 of the parent.

12. The method according to claim 10, wherein the stereodefined oligonucleotide variant(s) identified in step c. retain an EC50 value of not larger than 3 to 10 times that of the parent compound.

13. The method according to claim 1, wherein the parent oligonucleotide and the members of the library of stereodefined oligonucleotide variants comprise at least one LNA nucleoside selected from the group consisting of beta-D-oxy-LNA, 6'-methyl beta-D-oxy LNA nucleosides and S(cET).

14. The method according to claim 1, wherein the library screen performed in step b) comprises screening for hepatotoxicity in vitro in primary hepatocytes.

* * * * *